(12) United States Patent
Minkofski

(10) Patent No.: US 10,842,677 B2
(45) Date of Patent: Nov. 24, 2020

(54) SOUND BAFFLING DEVICE AND MATERIAL

(76) Inventor: Horst Burghardt Minkofski, Vancouver (CA)

( * ) Notice: Subject to any disclaimer, the term of this patent is extended or adjusted under 35 U.S.C. 154(b) by 4816 days.

(21) Appl. No.: 11/265,408

(22) Filed: Nov. 1, 2005

(65) Prior Publication Data

US 2018/0185195 A1   Jul. 5, 2018

Related U.S. Application Data

(60) Continuation-in-part of application No. 09/464,160, filed on Dec. 16, 1999, now abandoned, which is a division of application No. 08/613,685, filed on Mar. 11, 1996, now Pat. No. 6,091,825.

(51) Int. Cl.
*H04R 1/10* (2006.01)
*H04R 1/02* (2006.01)
*A61F 11/14* (2006.01)

(52) U.S. Cl.
CPC .................................. *A61F 11/14* (2013.01)

(58) Field of Classification Search
CPC ........ Y10T 29/49005; Y10T 29/49575; H04R 1/026; H04R 31/003; H04R 7/125; H04R 2207/00; A61F 11/14
USPC ................ 381/381, 384, 394, 399, 345–346, 381/370–371; 181/129, 135
See application file for complete search history.

(56) References Cited

U.S. PATENT DOCUMENTS

| | | | | |
|---|---|---|---|---|
| 3,828,461 A * | 8/1974 | Roberts | ............................ | 43/102 |
| 4,009,461 A * | 2/1977 | Usry | ............................ | 336/197 |
| 4,056,697 A * | 11/1977 | Heil | ............................. | 381/408 |
| 4,439,644 A * | 3/1984 | Bruney, III | ................... | 181/151 |
| 4,606,133 A * | 8/1986 | Mills | ........................ | 33/366.14 |
| 4,658,931 A * | 4/1987 | Curry | ............................ | 181/129 |
| 5,125,031 A * | 6/1992 | Ledonne | .................. | H04R 1/02 181/161 |
| 5,638,456 A * | 6/1997 | Conley et al. | ................. | 381/190 |
| 6,229,699 B1 * | 5/2001 | Kerrigan et al. | ........... | 361/679.6 |
| 2001/0005422 A1 * | 6/2001 | Nakamura | ............ | H04R 1/2819 381/349 |
| 2004/0012921 A1 * | 1/2004 | Hidaka et al. | ................. | 361/685 |
| 2004/0264725 A1 * | 12/2004 | Madsen et al. | ................ | 381/328 |
| 2005/0089184 A1 * | 4/2005 | Wang | ...................... | H04R 1/288 381/345 |
| 2005/0094837 A1 * | 5/2005 | Parker | ....................... | H04R 1/02 381/355 |

* cited by examiner

*Primary Examiner* — George C Monikang
*Assistant Examiner* — George Monikang

(57) ABSTRACT

A sound or thermal baffling device comprising an enclosure containing a variable density fluid and a force generating means for preserving and creating the structure and form of the enclosure, the shape and composition of the enclosure crafted to vary the baffling characteristics of the enclosure, and a further embodiment showing how a cellular material containing a variable density fluid may be created and used, and a still further embodiment showing improvements to ear protectors and head phone sets, including latching means for attaching these and other devices to the ears and head. Various applications involving previous as well as new uses are set out, including a description of how dynamic sound baffling may be implemented.

17 Claims, 10 Drawing Sheets

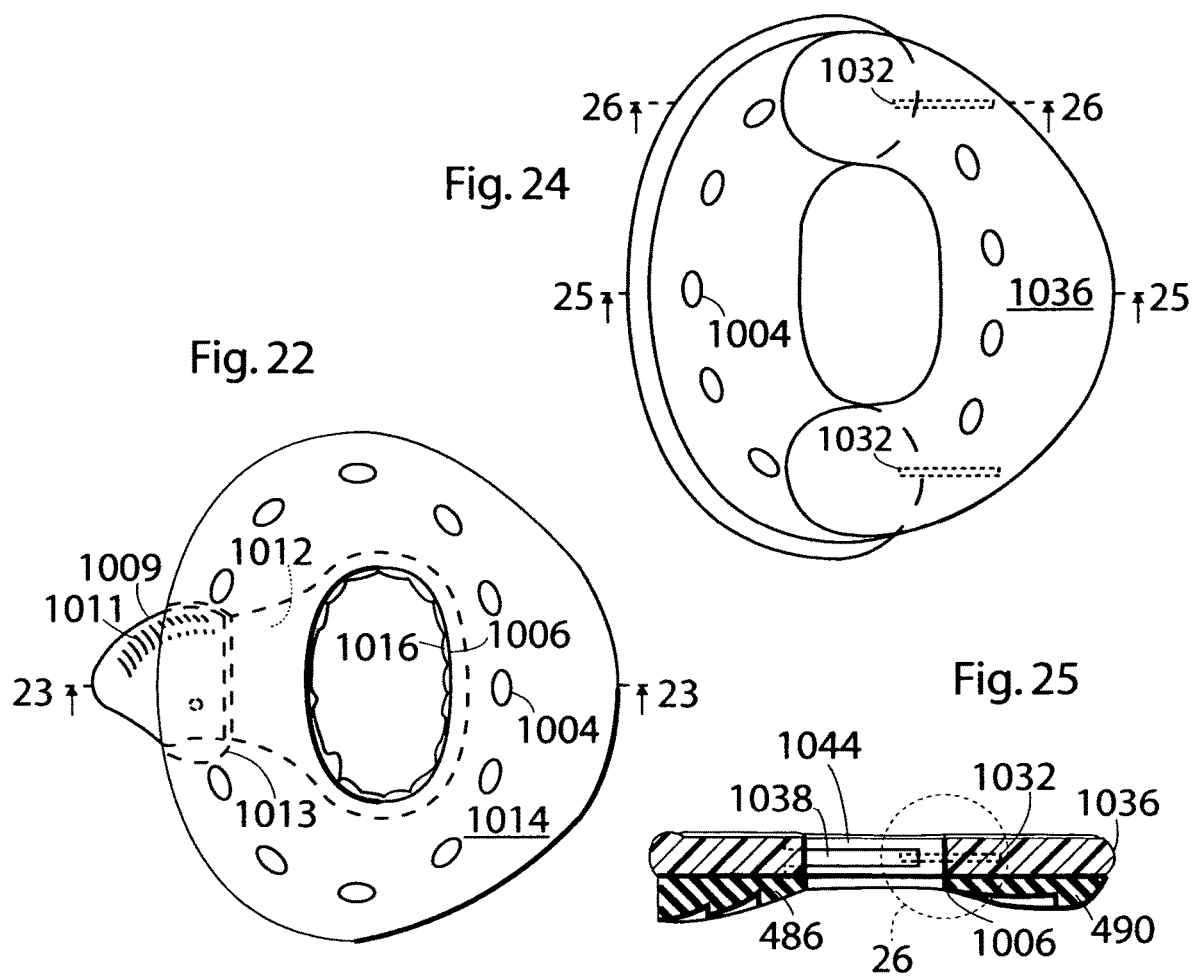
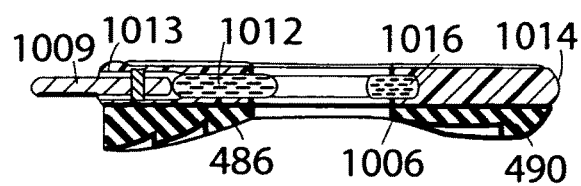
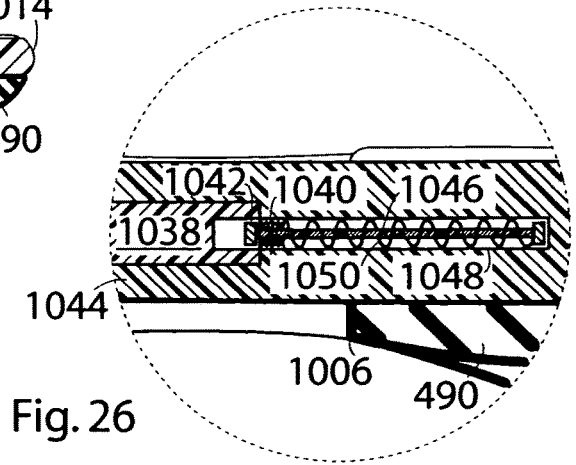

SOUND BAFFLING DEVICE AND MATERIAL

This is a continuation in part of application Ser. No. 09/464,160, which was a division of application Ser. No. 08/613,685 that was issued as U.S. Pat. No. 6,091,825, and the disclosure of the application Ser. No. 09/464,160 is accordingly incorporated herein in its entirety by reference. This invention relates to the field of sound baffling devices, and more particularly the use of an enclosure containing a vacuum to baffle sound, as well as the various practical uses to which this invention may be put. Some other improvements, which aid the invention in operation, are also shown.

BACKGROUND OF THE INVENTION

Many previous sound-baffling devices also may have had no facility for dynamically adjusting the ambient sound. If such facility was present, it may have involved a change in the spatial disposition of the sound baffling devices. The ability to dynamically alter the inherent sound baffling characteristics of sound baffling devices may not have been shown previously.

SUMMARY OF THE INVENTION

Although the theory of operation and/or functioning of the invention is not fully understood, according to one of its aspects the invention comprises the use of an enclosure containing a vacuum to baffle sound. Although the invention may baffle sound by means of sound deflection, sound reflection, and sound absorption like some previous devices, the use of a vacuum improves on this. A vacuum, being substantially opaque to sound, should function as a total barrier to sound, although peripheral transmission and absorption along the enclosure may still take place.

Since a perfect vacuum should be opaque to sound, a perfect vacuum should function as a complete barrier to sound. In practice, the vacuum may not always be perfect. Hence there may be a small amount of transmission through the vacuum. However, this amount should be so small as to be negligible.

BRIEF DESCRIPTION OF THE DRAWINGS

FIG. 10 (A, B, C, D, E) shows a transduction circuit.

FIG. 22 shows a pneumatic or hydraulic clip depending on whether the actuating fluid is a liquid or a gas.

FIG. 23 is a section of FIG. 22, and most auspiciously, shows a cross section of the expandible annular tube.

FIG. 24 shows a flat sliding clip.

FIG. 25 is a section of FIG. 24.

FIG. 26 is an enlarged section of FIG. 24 and, in particular shows one example of a holding means that may be used to connect the first and the second arc shaped flanges.

DESCRIPTION OF THE PREFERRED EMBODIMENT

Figure 1:
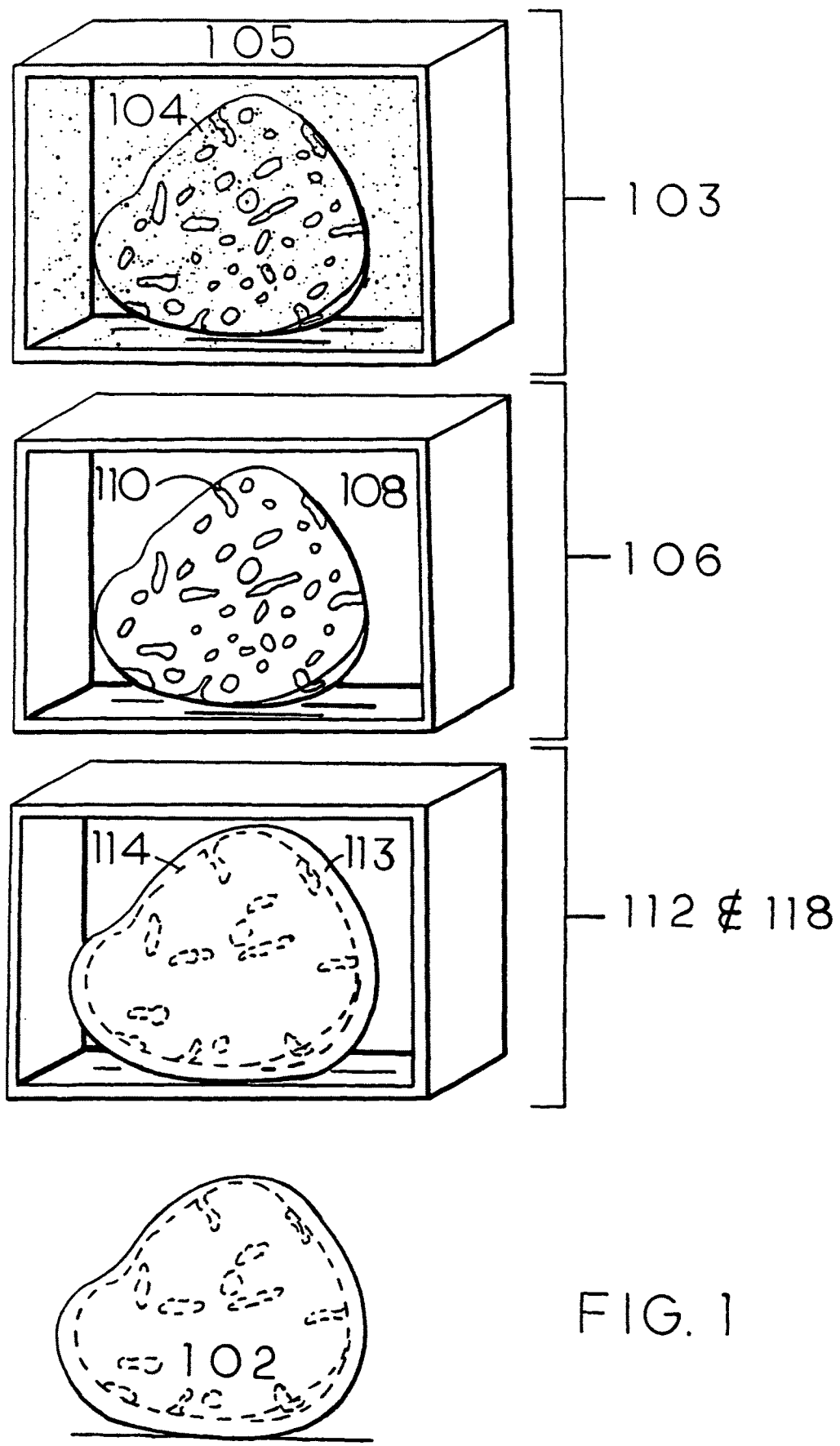
FIG. 1 shows the first process of manufacture that uses a material having a porous structure to create a cellular material.

Although the theory of operation and/or functioning of the invention is not fully understood, as shown in FIG. 1 according to one of its aspects the invention comprises a sound baffling device having at least one enclosure (52)

containing a vacuum (56), such that the transmission of sound through said sound baffling device is substantially barred by said vacuum.

Figure 2:
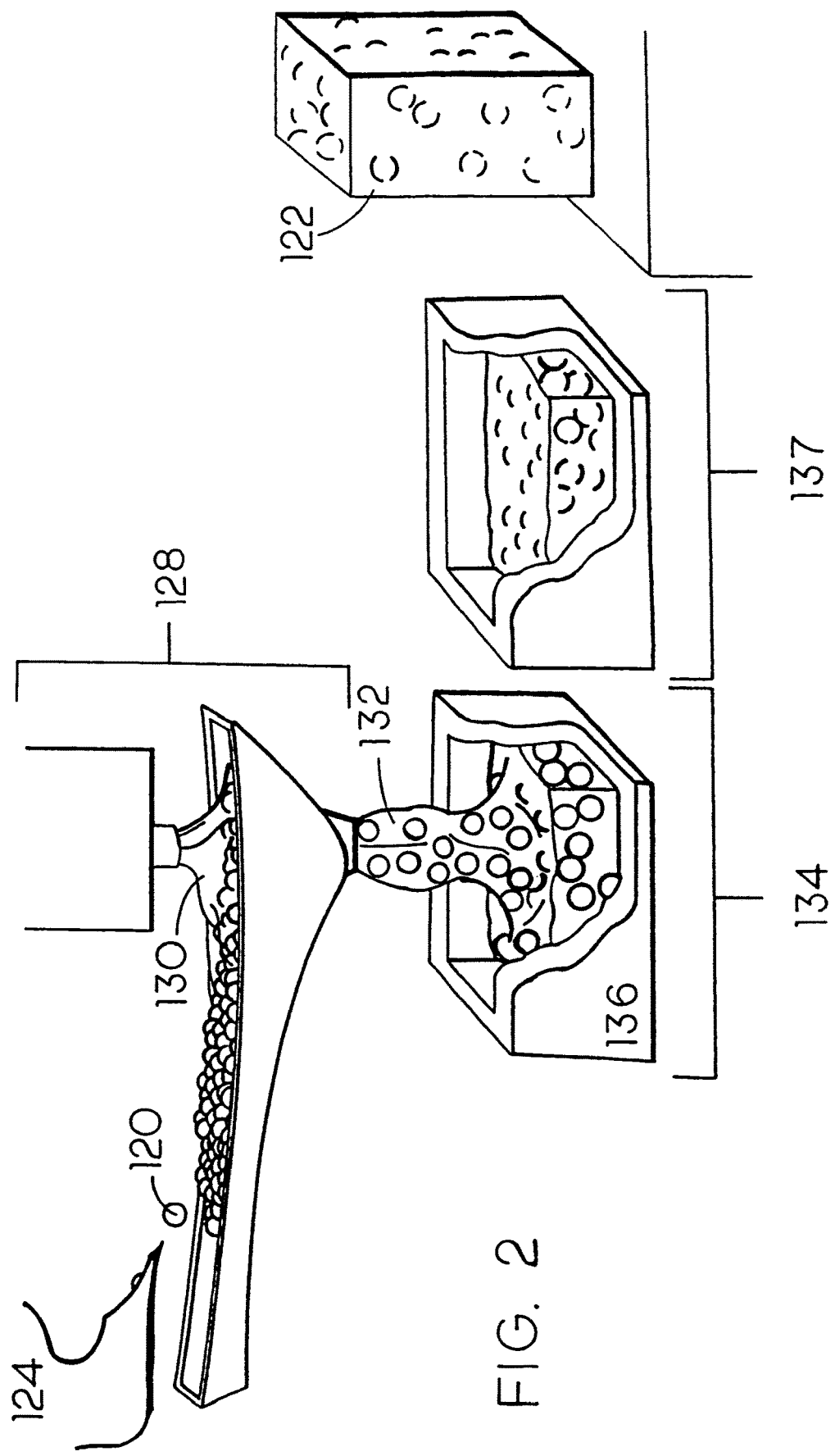
FIG. 2 shows the second process of manufacture that uses a pourable product to create a composite cellular material.
Figure 3:
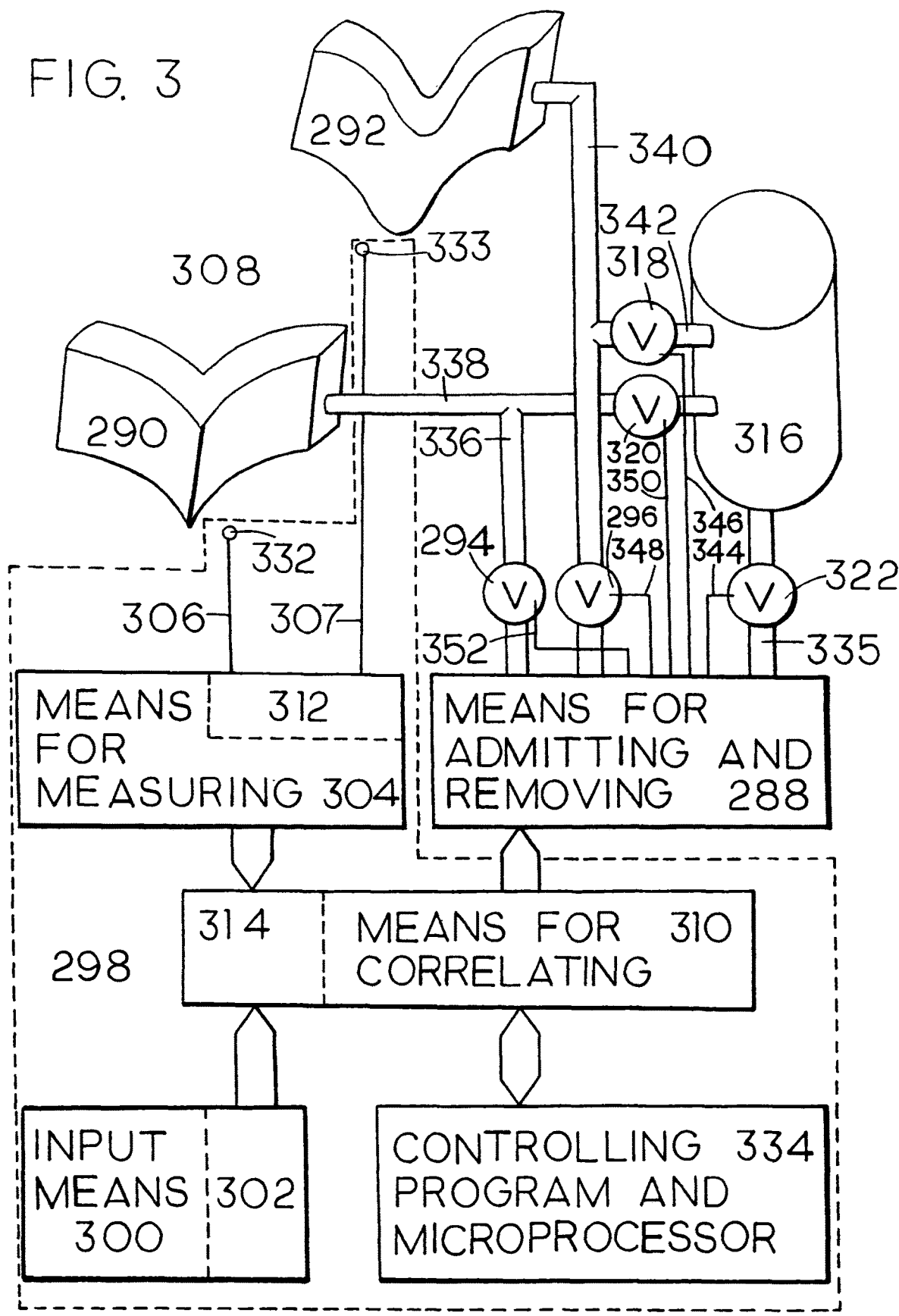
FIG. 3 shows the drawing of the preferred embodiment of the parent application. It illustrates how a large scale arrangement of enclosures may be combined to comprise an a sound baffling device and how this sound baffling device may be used in conjunction with a controlling means having a controlling program and a microprocessor. The sound-baffling device shown in this drawing should be capable of dynamically controlling the ambient sound.

The cutaway view of FIG. 2 expands on this. A cross section of the walls of the enclosure is shown as well as a glimpse of the interior. In operation, the vacuum is contained and preserved by the walls (54) of the enclosure. Initially the vacuum may be created by removing matter within the enclosure by means of a valve (FIG. 13) located in or attached to the walls of the enclosure. This procedure should be used when the enclosure is constructed for connection to a controlling means. It may allow not only the removal of the matter from within the enclosure but also allows the matter to be returned to the enclosure should this be desired, as may often be the case where a controlling means is connected to the enclosure. In most cases the matter will be a gas or air, or a mixture of gases. However it may sometimes be preferable to use a liquid or particulate or granular forms of matter to achieve specialized sound baffling characteristics.

Alternatively, the vacuum may be created within the enclosure by constructing and sealing an enclosure within a vacuum chamber. This assures that the vacuum within the enclosure will be maintained under ambient conditions. This type of construction maintains substantially constant sound baffling characteristics for the enclosure and is preferable when these types of characteristics are required. The method of construction may be substantially the same as that used for the creation of vacuum chambers and vacuum bottles or containers by previously used engineering methods such as pinch-off (A pipe or tube is connected to the enclosures and used as a conduit for creating the vacuum. Usually the pipe or tube is comprised of the same material as the enclosure. After the required pressure is reached within the enclosure, the pipe or tube is pinched off sealing the enclosure (This may be done by using special pinch-off pliers). Heat or a sealant may also be applied to seal the remnant pinched off section of the enclosure. Finally the excess section of the pipe or tube is removed, leaving a sealed enclosure). Or the enclosure may be constructed within the vacuum chamber by taking preformed walls or sides and joining them, preferably with interlocking joints, to comprise the enclosure. A suitable sealant is then applied to seal the joints so that the vacuum may be preserved against ambient matter. Such a sealant would preferably be a silicone or epoxy sealant.

A still further procedure may use a hollow stem attached to a sealing saddle or cup to remove the homogeneous fluid from the enclosure. The enclosure is created under atmospheric pressure. Then, a hole is created in the enclosure by using a drill, laser, or any other convenient tool having the requisite capacity. Next the enclosure is held fixedly within a vise or equivalent holding instrument while the sealing saddle or cup is hermetically attached above the hole in the enclosure. The hollow stem of the sealing saddle or cup is attached directly or indirectly to a vacuum pump, and the homogeneous fluid is removed from the enclosure until the desired internal pressure is achieved within the enclosure.

The sealing saddle or cup may also contain a tool for closing the hole in the enclosure. This could be a welding tool, for metal or glass enclosures, or a sealing tool that applies a sealant to the hole, for glass or plastic enclosures, or any other tool that has the capacity to hermetically seal the rarified homogeneous fluid within the enclosure. After the enclosure is sealed the sealing saddle should be removed from the enclosure prior to preparing a new enclosure.

The sealing saddle or cup may also contain a fluid transfer connection to a matter density reservoir. In this case, after substantially all fluid is removed from the enclosure, a preferred fluid from the matter density reservoir may be admitted to the enclosure prior to sealing. Such a preferred fluid may be any one of the noble gases, or any other fluid that lends novel results to the finished enclosure (e.g. the noble gases).

The advantage of this cellular material is that is allows the construction of a large sound baffling device that should require no internal supporting struts for the enclosures. Because of the external pressure that may act on the enclosure, for large enclosures internal supporting struts may be required. This requirement may depend on the strength and shape of the material of the enclosure as well as on the external pressure. However for a sufficiently small enclosure the inherent strength (the ability to resist external pressure) of the enclosures may show an increase proportional to the decrease in size, and the enclosures may therefore be able to resist the external pressure and maintain structural integrity without supporting struts.

Many materials may show this proportional increase in inherent strength with decreasing scale, among them the glasses and the plastics. It may therefore be preferable that the cellular material is formed from enclosures comprised of glass so that said material is a glass having a cellular structure. A way of constructing such a material may be found by placing a form filled with glass ellipsoids or other regular solids (e.g. a regular polyhedron), containing a vacuum inside a vacuum chamber that is evacuated. The ellipsoids other. regular solids may conceivably be any size attainable by existing art but it may be preferable that the size falls into a range of proportions varying from about one quarter inch to about four to five inches. And another preferable range of proportions may vary from about one inch to about five to six inches. Heat is then applied causing the walls of the glass ellipsoids or other regular geometric shapes to coalesce through partial melting, thereby forming common walls. In this way, upon cooling a cellular material comprised of glass and containing a vacuum may be created.

The same procedure may be applied to plastic globules or other regular geometric shapes containing a vacuum. Depending on the plastic used and the process desired, heat or a catalyst or an adhesive sealant may be applied to the plastic globules or other regular geometric shapes. This may cause the walls or boundaries of the plastic globules or other regular geometric shapes to coalesce through partial melting or bonding, thereby forming common walls. In this fashion a cellular material comprised of plastic and containing a vacuum may be created.

In general, when using simple ellipsoids or other regular geometric solid shapes (e.g. a regular polyhedron), the resultant material may be more effective when the ellipsoids or other regular geometric solid shapes are all the same size, or when their sizes fall into a geometrical progression that maximizes the filling capacity of the ellipsoids or other regular geometric shapes (Filling capacity is defined as the percentage of total material volume that is occupied by the ellipsoids or other regular geometric shapes after random mixing for some assemblage of the ellipsoids or other regular geometric shapes.) It has been found that for spheres that are of substantially the same size and shape the maximum filling capacity under random mixing is about 0.6400 or 64%.

One of the preferable features when creating a cellular material wherein substantially each cell contains a vacuum, is to use a packing that achieves the maximum amount of vacuum per volume possible. To this end an enclosure having an ellipsoid surface is capable of achieving even better results than an enclosure having a spherical surface.

For ellipsoids the maximum filling capacity under random mixing is higher than what is attainable by using spheres; ellipsoids can achieve about 0.6800 or 68%. Therefore another aspect of the invention comprises replacing the use of spherical enclosures in these embodiments of the invention with the use of ellipsoid enclosures all having substantially the same size, or falling into a geometrical progression that maximizes the filling capacity of the ellipsoids or other regular geometric shapes.

It has also been found that a preferable geometrical relationship among spheres, ellipsoids, and other regular geometric shapes (e.g. a regular octahedron) may be created by using two sizes proportioned in a ration of one to four; one of the smaller sized regular geometric solid shapes (e.g. a sphere or ellipsoid) to four of the larger sized geometric solid shapes. Assuming the size of the larger size regular solid to have a value of 1, the smaller size regular solid would then fall into a range from about 0.115 to 0.225, or preferably from 0.13 to 0.21, or more preferably from 0.15 to 0.19, proportionally. (e.g. If a sphere having a diameter of 1 inch is used for the larger size, then the smaller size will have a diameter falling between 0.115 to 0.225 inches, or preferably from 0.13 to 0.21 inches, or more preferably from 0.15 to 0.19 inches, proportionally. The appropriate proportion of larger spheres to smaller spheres would then call for the use of four large spheres for every small sphere used. Also, from a different perspective, given an ellipsoid having a volume of 1 cubic inch, where the ellipsoid is the lesser sized regular solid, the volume of the larger sized ellipsoid would be about 5.88 cubic inches)

It may therefore be preferable that according to one of its aspects the invention further comprises; A process of manufacture for creating a cellular material containing a vacuum for baffling sound, the first step in the process of manufacture comprising the creation of said vacuum within a plurality of disjointed enclosures having an ellipsoid surface, the second step in the process of manufacture comprising the creation of a binding mixture by mixing a binding agent with said plurality of disjointed enclosures containing said vacuum, the solidification of said binding mixture causing said plurality of disjointed enclosures to comprise a plurality of cells containing said vacuum, so that after completing the process of manufacture, said plurality of cells comprises said cellular material containing said vacuum.

A further way in which a cellular plastic may be created is by mixing a molten thermoplastic material with a gas or liquid which is volatile at normal atmospheric pressure and subjecting the mixture to elevated temperature or pressure in a closed chamber. The material is then released from the closed chamber through a suitable die opening, thereby releasing the pressure and causing the gas to expand. This results in a permanent porous or cellular plastic upon cooling.

If in addition thereto, the improvement comprises that the die opening is connected to a vacuum chamber, then when the vacuum chamber is evacuated concurrently with the expansion of the thermoplastic material, a vacuum may be incorporated into the cells of the material. This vacuum may be preserved against the action of ambient matter by incorporating a bitumen or other sealing agent into the thermoplastic material. Or the vacuum may be preserved by applying a suitable sealant to finished units of said thermoplastic material before removal from the vacuum chamber. For expandable polystyrene or polyurethane such a sealant may be a urethane or epoxy sealant. And this material may be used as a binding agent. A vacuum chamber may be filled with enclosures containing a vacuum. The vacuum chamber further has the die opening above and as the cellular plastic is expanded into the vacuum chamber through said die opening it should fill the voids between the enclosures. Upon solidifying the cellular plastic will therefore function as a binding agent for the enclosures containing a vacuum.

Figure 5:
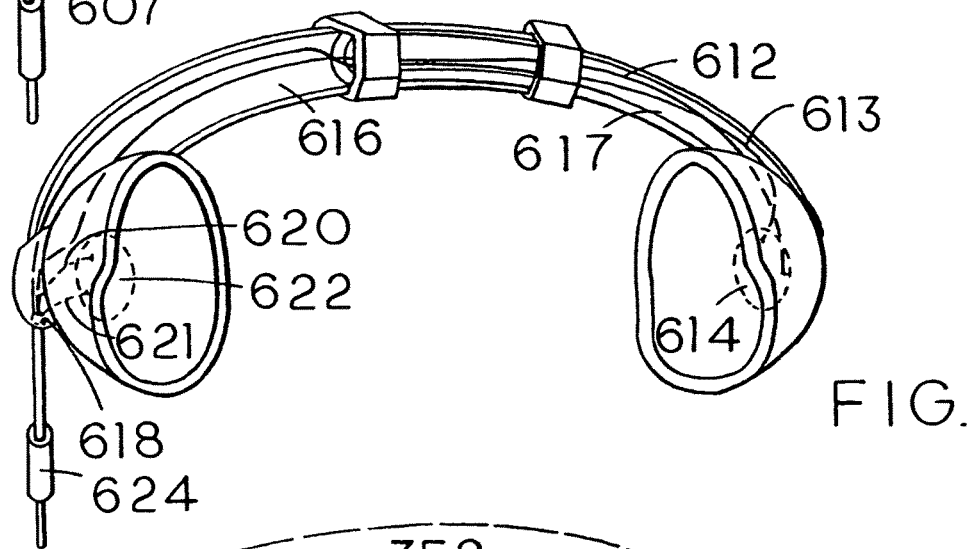
FIG. 5 shows how the single path connecting means may be carried within the grooves of a fitting means comprised of arc shaped bands.

A first process by which a material having a cellular structure can be created is shown in the sequential views of FIG. 5 which illustrates that the invention comprises a first process of manufacture that uses a material having a porous structure to create the material having a cellular structure (102), said first process having the following steps in the sequence set forth;

The first step (103) in the first process of manufacture comprising the placing of said material having a porous structure (104) within a vacuum chamber (105), The second step (106) in the first process of manufacture comprising the creation of a vacuum (108) within said vacuum chamber, so that after a suitable interval of time said vacuum extends substantially throughout the porous structure (110) of said material, The third step (112) in the first process of manufacture comprising the application of a sealant (113) to the surface (114) of said material such that the vacuum is incorporated within said porous structure and is preserved against contact with ambient matter, The fourth step (118) in the first process of manufacture comprising the application of a suitable curing process when necessary, so that after the completion of said first process of manufacture the material having a cellular structure (102) is created.

The porous structure of the material used in the first process may be comprised of tubular openings to the surface or microscopic transport apertures that allow the air to escape when the material is exposed to the vacuum within the vacuum chamber. (The vacuum chamber is represented by the cross-sectional view of the box in FIG. 5.) In step 2, the transport of the air (The air is indicated by stippling in the illustration of the first step (103) of FIG. 5) from the porous material and out of the vacuum chamber upon the creation of the vacuum does not have to be instantaneous. If it is not, a reasonable length of time is allowed for the air to transport out of the material upon application of the vacuum. When the transport is completed the surface of the material is sealed with a suitable sealant. For example, when the material is a porous plastic a suitable sealant may be a properly admixtured epoxy resin. Or a urethane sealant may also be used.

The sealing of the surface may also involve a suitable curing process as defined in step 4. But, especially when the sealant is fast setting and the surface is sealed more or less instantaneously; this may not always be necessary. For thermosetting plastics the curing process should involve the application of heat and may or may not involve a chemical catalyst. For some materials it may merely involve waiting for the sealant to harden and any excess vapor to be drawn off.

It follows that the porous material need not be plastic but may also be metal, glass, or any other suitable material. It may therefore be preferable that said material having a porous structure is a naturally occurring material having a porous structure. Such naturally occurring materials may be both organic and inorganic. Among the organics we find the sponges and among the inorganics we have materials such as pumice. It may therefore be preferable that said naturally occurring material having a porous structure is pumice. The pumice is brought into the vacuum chamber and then the chamber is evacuated. After the ambient matter has been substantially removed from the cells of the pumice the surface of the pumice is sealed in the presence of the vacuum. Although it appears at first glance that polysulfide sealants may be used, they are known to degrade somewhat when in contact with a vacuum due to out-gassing etc. This may, if the exposure of the polysulfide sealant to the vacuum is significant, compromise the sealing function. In general, sealants that are known to have a high risk for degradation upon contact with a vacuum, are the acrylics, polyamides, polysulfides, and neoprenes. It is therefore preferable that the sealant be selected from a group that may in general function reliably in contact with a vacuum, notably the epoxies, urethanes, and silicones. For the sealing of pumice a silicone caulking or sealant composition may therefore be preferable.

The objective, which is attained by the application of the sealant in the first process of manufacture for creating a cellular material, is the preservation of the incorporated vacuum against any influx of ambient matter. This ambient matter may be a particulate, a liquid, a gas, or the air of the atmosphere. It may therefore be preferable that the ambient matter be air.

Figure 6:
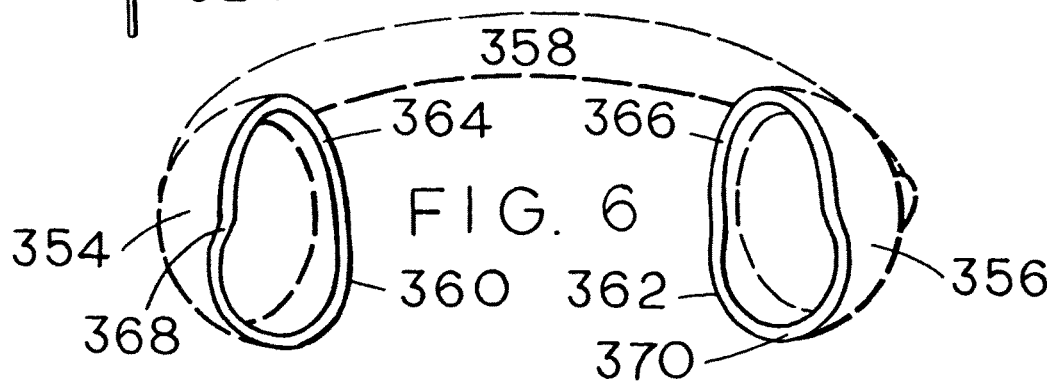
FIG. 6 shows the lip contour that may be applied to the lips of sound baffling cups and the medial side of some of the latching means.

According to a further aspect the invention comprises a plurality of enclosures containing a vacuum, or a plurality of the material having a cellular structure that has been created by the first process of manufacture for creating a material having a cellular structure, so that said enclosures or said cellular material are dimensioned to comprise a product having a size and shape suitable for pouring (FIG. 6, 120), such that said product may be poured into holes and cavities, so that the transmission of sound through said holes and cavities is substantially reduced. As also shown in FIG. 6, the product suitable for pouring should have a size and shape that is substantially uniform. Or putting it another way, the precursor enclosures or the cellular material that are used in the creation of a particular body of material or product that has been produced by the process shown in FIG. 6, should all be of substantially the same size and shape. (A precursor enclosure is an enclosure that is used as an element of a process or method.)

Equivalently sized and shaped enclosures may preferably be used in general, and the preferred order of size for disjointed enclosures to be formed into a cellular material would be from about the size of a small marble to the size of a ping-pong ball or golf ball. They could also be somewhat bigger, or about the size of a tennis ball or softball. This size would preferably fit into a range from about one quarter inch to about four to five inches. And the enclosures need not be globular spherical or ellipsoidal; rather they could have the shape of any regular or semi regular three dimensional geometric shape in the requisite size range. In particular they could have the shape of any of the regular polyhedrons.

One area of application for this embodiment should be the construction industry. Various kinds of buildings may have holes, gaps, spaces or voids that can admit ambient noise. These gaps may be filled by pouring the enclosures into them. Although it may be preferable that the enclosures are glass globules or comprise other regular geometric shapes (e.g. a regular polyhedron), the enclosures may also be made of plastic, metal, or any other material that can be fashioned to this purpose. Furthermore, in filling these voids within buildings, the enclosures should also aid materially in improving the insulating properties of the structures.

Inherent insulating properties may be a general advantage of any of the enclosures, whether part of a cellular structure or not. For a large autonomous enclosure, the addition of a suitable reflective coating to the inside walls of the enclosure should substantially reduce the transmission of heat by means of infrared radiation. Although reflective coatings may have been used previously to reduce the transmission of infrared radiation, their use in building blocks, bricks, or structural components containing a vacuum may be new. Hence, if the invention is used with this end in mind, both maximal soundproofing and insulating characteristics may accrue to materials or components that also incorporate the reflective coating.

When used in the construction industry, the enclosures may also be applied as a finish to surfaces. The surface (e.g. the exterior or interior wall of a building) is prepared to accept the enclosures by being sprayed with a binding agent or simply by preparing the surface with mortar or stucco etc. The enclosures are then applied to the binding agent, mortar, plaster, putty, or stucco etc., before setting takes place. For materials that have a moldable surface, such as mortar, plaster, putty, stucco, etc., it may be preferable that the enclosures have a polyhedral shape, and more preferably the shape of a prism, or the shape of a tetrahedron. The sharp vertices of these polyhedrons will then sink into and find anchor in the moldable material. And a decorative enamel or finish may also be applied to the enclosures in their manufacturing prior to their use in the finishing of surfaces.

Although the enclosures dimensioned to comprise a product suitable for pouring may be loosely poured into requisite holes, gaps or spaces it is also possible to add a suitable binding agent to fill in the air voids between the enclosures. For example, using a nylon filler in conjunction with glass globules or other regular geometric shapes (e.g. a regular polyhedron) containing a vacuum would allow the creation of a mixture for the elimination of air voids. Such a mixture may, after applying a suitable catalyst when necessary, set to form a material having a cellular structure. And this material should have a shape conforming to the holes, gaps, spaces, or voids within which the enclosures are poured, in effect functioning as a filler insulator and sound baffling material. Accordingly it may be preferable that the invention is comprised of a plurality of the product having a size and shape suitable for pouring and having a spatial distribution within a hole or cavity, said plurality further having a suitable binding agent added to form a mixture within said hole or cavity, so that said binding agent and said plurality form a cellular material within said hole or cavity.

As shown in FIG. 6 according to another of its aspects the invention is comprised of a second process of manufacture that uses the product having a size and shape suitable for pouring to create a composite cellular material, said second process having the following steps in the sequence set forth;

the first step (124) in the second process of manufacture comprising the creation of said product (120), the second step (128) in the second process of manufacture comprising the addition of a suitable binding agent (130) to said product, such that said binding agent and said product form a mixture (132), the third step (134) in the second process of manufacture comprising the application of a shaping means (136) to said mixture, such that said mixture assumes a preferred shape, the fourth step (137) in the second process of manufacture comprising the application of a suitable curing process when necessary, so that a composite cellular material (122) is created upon the completion of said second process of manufacture.

This second process of manufacture shows how to create a composite cellular material from independently created enclosures and/or how to create a composite cellular material from blocks of cellular material created by the first process of manufacture. The independent enclosures or the blocks of cellular material are first combined with a suitable binding agent. A suitable shaping means is then applied. When the product used is comprised of plastic, this may be any one of the known methods of centrifugal casting, injection molding, contact molding etc. A curing process may then follow when necessary. For example, when using an epoxy resin with a product comprised of plastic a fatty amine curing agent may be used.

The binding agent used may also be a plastic, which may or may not require a catalyst, retardant, accelerator, etc. It may therefore be preferable that the binding agent for said product is a plastic in combination with the catalyst required for said second process of manufacture. The catalyst is optional depending on the plastic. For thermosetting plastics it may simply be heat.

Alternatively, the product may simply be a plurality of glass globules or other regular geometric shapes (e.g. a regular polyhedron), to which is added a binding agent comprised of glass fibers. The glass globules or other regular geometric shapes and the fibers may fuse under the application of heat. It may therefore be preferable that the product used in said second process of manufacture is comprised of glass globules or other regular geometric shapes containing a vacuum. It is a simple matter to use a plastic resin in conjunction with the glass fibers. This may produce a cellular material comprised of fiberglass having the glass globules or other regular geometric shapes embedded within it.

Fibers comprised of the same material as the enclosure precursors may be used in general to aid in a fusing process. For metal enclosure precursors metal fibers may be used. These may not always be of the same metal as the enclosure precursors; it might be preferable to use nickel fibers with steel enclosure precursors or zinc fibers with brass enclosure precursors etc. On the other hand, a general process for facilitating fusion would of course comprise the use of the same material fibers with the same material enclosure precursors. ('Enclosure precursor' is simply a label for an enclosure that may be used as a precursor in a contemplated process.)

It would therefore be preferable, when fusing the enclosure precursors, that glass fibers are used with glass enclosure precursors, thermoplastic fibers are used with thermoplastic enclosure precursors, and metal fibers are uses with metal enclosure precursors.

Alternatively, it may often be preferable to use a glass with a metal or a plastic with a glass. This, as said before, could involve embedding a plurality of glass enclosure precursors in a binding matrix of nylon. But it may also be preferable to embed a plurality of metal enclosure precursors in a binding matrix of glass; the metal enclosures are simply mixed into the molten glass. Or the metal enclosure precursors can be mixed into a binding agent comprised of molten plastic. The operative principle here is to strive for a combination of binding agent and enclosure precursor materials that have a ratio of their characteristic impedances at about one to ten (where the enclosure precursors have at least ten times the characteristic impedance of the binding agent). This should increase internal acoustic reflectance in the resulting material.

A further process comprises the use of a binding agent in an environment of less than atmospheric pressure. The enclosures are mixed with the binding agent and then placed in a vacuum chamber. The pressure in the vacuum chamber is reduced until the binding agent begins to boil: this will happen at about the vapor pressure of the binding agent. When the binding agent solidifies it will contain bubbles containing binding agent vapor at about the vapor pressure of the binding agent. This process reduces the amount of binding agent needed and decreases the overall weight of the resulting cellular material. Any excess binding agent created by the boiling stage should be drawn off. Alternatively, the binding agent may be administered in an amount just sufficient to bind the enclosures into a cellular material upon boiling.

When fusion is used it may be preferable to use a form that fully encloses the glass ellipsoids or other regular geometric shapes (e.g. a regular polyhedron). The form will be capable of some contraction so that pressure may be applied to the glass spheres or other regular geometric shapes (e.g. A cube with a square cover; the cube is filled with the enclosure precursors and the cover applies the contracting force or pressure). As soon as heat is applied and the glass spheres or other regular geometric shapes reach a malleable state, pressure is applied by the form, and the spheres or other regular geometric shapes are squeezed together to eliminate voids between the spheres or other regular geometric shapes. When using fusion, this can be done with or without the catalytic aid of the material fibers in the fusing process. Of course the enclosures may have any shape, a spherical shape, an ellipsoidal shape, or the shape of any regular polyhedron.

This process may be applied to produce a cellular material in the shape of the enclosures detailed by reference numbers used in the interval from (138-279) in the specification below. The form would have the shape of the corresponding enclosures. Therefore the resulting material would also have the shape of the corresponding enclosures. Of course, any shaping means used in a process for forming a cellular material would be able to construct these shapes as well.

If glass globules or other regular geometric shapes (e.g. a regular polyhedron) are used an appropriate binding agent may also be nylon 6/6. For example, when contact molding is used, generally a gelatin coat resin is laid up against a polished and waxed mould. The nylon laminating resin and the glass globules or other regular geometric shapes are then laid on. Also heat may be used as a catalyst to accelerate this process. It may therefore be preferable that said binding agent is nylon and the enclosures are glass globules or other regular geometric shapes containing a vacuum.

Spheres or ellipsoids may also be used to construct a vacuum capacitor. A vacuum capacitor (760) should be designed to imitate the properties of a vacuum chamber, to function as a repository for a vacuum. But a vacuum capacitor is superior to a vacuum chamber in that it allows a large amount of vacuum to be created more quickly in the associated vacuum system and is also capable of sourcing more than one vacuum.

A vacuum capacitor may be constructed from spheres (762), ellipsoids, or regular polyhedrons, although any shape of enclosure may be used. When using spheres, the spheres are arranged in any well-known arrangement (e.g. a face centered cubic structure) and valves (764) and a piping network (766) are added, with at least one valve being added for each sphere. The valves may be located in the central space created within each tetrahedral packing of spheres. Each valve is subject to control from the controlling means and the controlling means has a logic map, which contains a record of the overall geometry of the vacuum capacitor as well as current information detailing the contents of the enclosures in the vacuum capacitor, and a description of the overall arrangement of spheres and valves and how they are connected by the piping network.

All spheres are kept at the same high level of evacuation by the means for admitting and removing. When vacuum is required in an enclosure one of the spheres is accessed by opening its valve and the enclosure is connected to that sphere by the controlling means and the piping network. (Connected here implies that the requisite valves are opened so that the fluid contained in the instant sphere and the enclosure can equilibrate. When the pressure between the enclosure and the instant sphere has equilibrated, the valve is closed isolating this sphere from the enclosure. Next a second sphere is connected to the enclosure and the process is repeated until the level of vacuum in the enclosure is the required level. And concurrently, previously accessed spheres can be evacuated to their highest vacuum state. Sensors (768) located within the spheres provide the means for measuring with current information on the instant pressure that is present within the spheres. This allows the controlling means to focus the means for admitting and removing to evacuate only those spheres that have a high internal pressure and to select spheres at the desired level of evacuation for reducing pressure within the enclosures Although the sensors may have a separate data bus, in practice it may be preferable to run the sensor wires through the piping network. When a piping network is available it is usually more convenient to run sensor cable or wire through or in conjunction with the piping network. This may also reduce the chance of leakage from the vacuum system.

The advantage of this embodiment lies in the fact that equilibration occurs more rapidly and efficiently and that more than one enclosure can be equilibrated at any one time. The spheres are constructed to approximately the average size of the enclosures. Therefore with each separate access of the vacuum capacitor the pressure in the enclosure is substantially halved so that on access to succeeding spheres the pressure varies as ½, ¼, ⅛, etc. In comparison a regular vacuum chamber having twice the size of an average enclosure could only create one-third the pressure in the enclosure before having to be reevacuated. The physical elements of a vacuum capacitor can also be used as a storage chamber, or a mixing chamber, or a matter density reservoir.

Another advantage of using a cellular material containing a vacuum is that for some embodiments the material may be milled to specification without loosing the ability to baffle sound. This is because only those cells which are at the surface being milled loose the ability to baffle sound, due to rupture being induced by the milling process. It may therefore be preferable that the invention is comprised of a cellular material or composite cellular material that is workable, so that it may be shaped to spatial specifications.

In practice, it may be desirable to create blocks or sizable solid aggregations of the cellular material and then reduce these aggregations into sheets by cutting or sawing or by any other suitable method. The thickness of the desired sheets then becomes relevant in determining the size of the enclosure or sphere or ellipsoid precursors. It has been found that to obtain substantial efficiency with regards to sound or thermal baffling of the ambient sound or thermal energy, it is preferable that the sheets be comprised of at least three layers of whole enclosures or ellipsoids. In this regard, it has also been found that the maximum cross-sectional distance through a sheet comprised of three layers of spheres is about 2.73 times the sphere diameter. Therefore, since there should be at least one cutting layer (the layer that is destroyed in making the cut) for every sheet, four layers of enclosures should be required for the making of one sheet of cellular material. It follows that the cuts through a block of cellular material should be made in increments of about 3.185 times the sphere diameter. The diameter of the requisite enclosures can then be obtained by dividing the desired thickness of the sheet by about 3.185; for a one-inch thick sheet one would therefore expect the spheres to be about 0.31 inch in diameter. And this calculation holds for regular polyhedrons as well. One merely inscribes a sphere within the polyhedron and proceeding as before calculates the diameter of the sphere and from that deduces the size of the polyhedron.

It is also possible to create the appropriate sheet thickness by creating one sheet at a time. A form is prepared and according to the size of the form and the size of the enclosures contemplated, the number of these enclosures required to fill the form is calculated. One enclosure contributes about 0.91 of its diameter to any linear distance in respect of which it comprises part of a spherical packing. So for a five by five or twenty five square feet form, when using enclosures having one inch diameters we obtain 60/0.91=65.93 enclosures in either direction; the total number of enclosures for one layer is then about 4347 enclosures and for the full sheet we have three times that or approximately 13040 enclosures for the whole sheet.

The requisite number of enclosures (13040) can then simply be poured into the form. Next the form is subjected to an adjustable shaking or vibrating so that the enclosures assume a three-layer packing. When the three-layer packing is achieved the binding agent is poured on to saturate the voids within the three-layer packing, and upon solidification the sheet is created. Of course this procedure could also be used in combination with fusion. And as discussed above, the two sizes should be proportioned in a ration of one to four. One of the smaller sized regular solids (e.g. a sphere or ellipsoid) to four of the larger sized solids may then be used when constructing these sheets as well.

If economical construction of a cellular material is desired it may be possible to use waste products such as discarded light bulbs. When light bulbs are used, care must be taken to use only light bulbs containing a vacuum. The light bulbs are then mixed with an appropriate binding agent to eliminate air voids and create a mixture. Next a suitable catalyst and shaping means may then be applied. After the mixture has set a cellar material wherein each enclosure is comprised of a light bulb containing a vacuum is created. Therefore according to a further aspect, the invention is comprised of a plurality of light bulbs containing a vacuum for baffling sound, said light bulbs mixed with a suitable catalyst to create a mixture, so that the solidification of said mixture comprises a cellular material. And a preferred shape may be formed though the application of a shaping means to said mixture.

An inexpensive material that can be applied to good effect is corrugated cardboard, suitably sealed by an encasing plastic film or other sealing agent. Each tube (corrugation) of the corrugated cardboard in effect comprises a supporting strut. The sealing agent may be a plastic envelope, which is evacuated to vacuum seal the corrugated cardboard such that the vacuum is incorporated inside the tubes of the corrugated cardboard. The plastic sheet used to vacuum seal the corrugated card board will then prevent the entry of ambient matter while the tubular cells of the corrugated card board will counteract the external pressure.

Effectively this comprises a very low cost embodiment suitable for use in building construction, And sheets of this specially prepared corrugated card board may further be modified for use in construction by including flat nailing strips for attaching the corrugated cardboard to two by fours and other timber or structural components used in the construction industry. Vacuum-sealed corrugated cardboard could therefore replace the use of acoustic wool and other building materials in some applications.

If a material having a cellular structure created from pumice is used, then the appropriate binding agent may be more of the sealant used to seal the pumice. This may comprise adding more of a silicone based caulking or sealant composition. Or it may be comprised of a further binding agent and/or filler which may also be mixed with a suitable catalyst.

And, to guarantee the highest quality for high and ultra high vacuum applications, it may be preferable to produce the ellipsoids or other regular geometric shapes (e.g. a regular polyhedron) by using pinch off for glass, plastic, and metal applications. This involves creating the initial ellipsoids or other regular geometric shapes with a tubular stem and then hermetically attaching the stem to a vacuum system capable of preparing a high or ultra high vacuum. Subsequent to evacuation the stem is pinched off to close the tube and seal the high or ultra high vacuum within the ellipsoids. In practice, for those embodiments that are not variable and are designed to prevent the transmission of sound or to function as a thermal insulator, the vacuum may be chosen to have a pressure less than $10^{-5}$ Torr, or a pressure less than $10^{-8}$ Torr. Alternatively, for purposes of the present discourse we define the gradations of a vacuum here as; an ultra high vacuum as having a pressure less than $10^{-5}$ Pascal, a high vacuum as having a pressure between $10^{-5}$ Pascal and $10^{-1}$ Pascal, a medium vacuum as having a pressure between $10^{-1}$ Pascal and 10 Pascal, and a low vacuum as having a pressure between 10 Pascal and $10^5$ Pascal.

Figure 7:
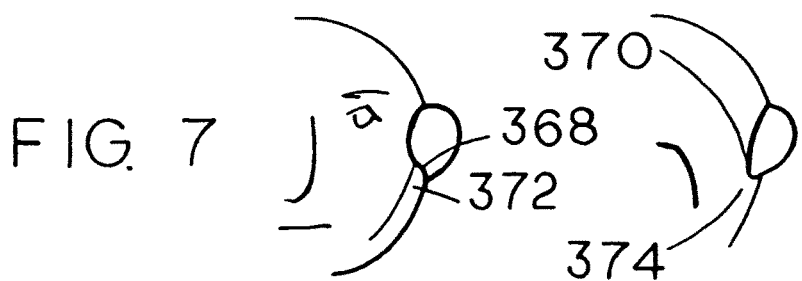
FIG. 7 shows how the lip contour fits the human body surface in the region of the head and neck.

As shown in FIG. 7 (A, B, C), according to another embodiment it may be preferable that the shape of the enclosure is selected from the group consisting of a sphere (138), a hemisphere (140), a zone and segment of one base (142), a zone and segment of two bases (144), a spherical sector (146), a lune (148), a cylinder (150), a cone (152), an elliptic paraboloid (154), a hyperboloid of one sheet (156), a hyperbolic paraboloid (158), an ellipsoid (160), a torus (162), a pyramid (164), a moebius strip (166), a klein bottle (168), a handle (170), a concave polyhedron (172), or a convex polyhedron.

Figure 8:
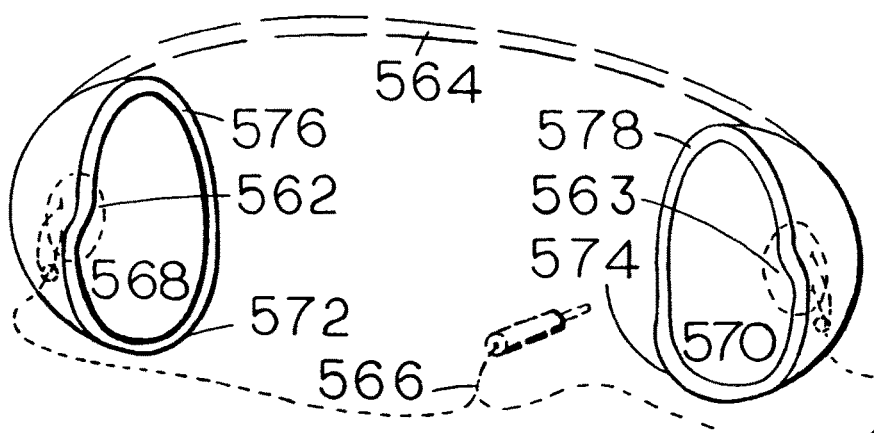
FIG. 8 shows the combination of sound baffling cups having a lip contour with headphone sets.

It may therefore also be preferable that the invention comprises an enclosure shaped like a convex polyhedron selected from the group consisting of a tetrahedron (174), a hexahedron (176), an octahedron (178), a dodecahedron (180), or an icosahedron (182). These regular polyhedrons are shown in FIG. 8, which also includes a drawing of the prism (184) and the antiprism (186).

Figure 9:
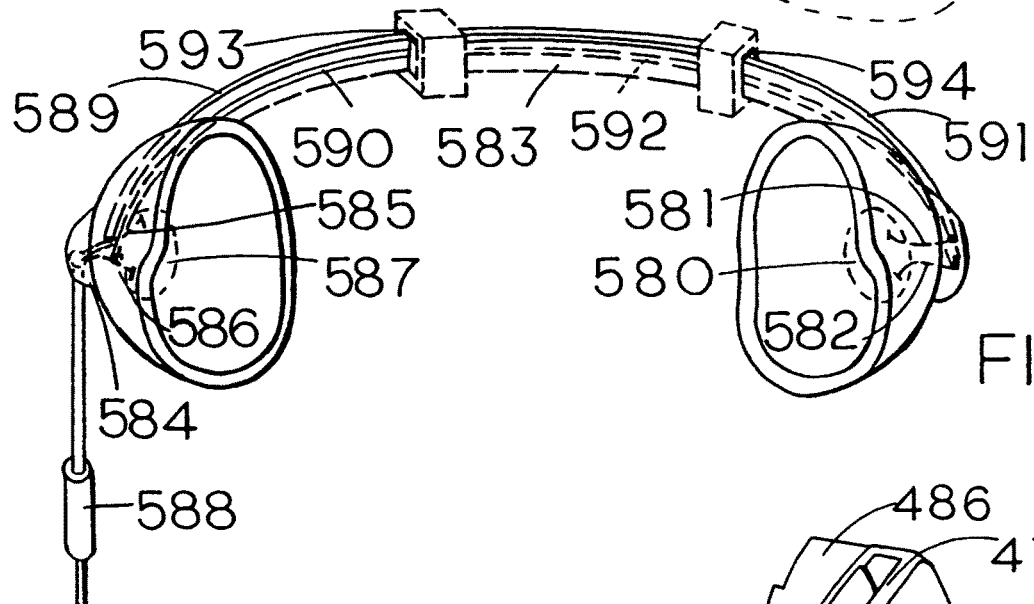
FIG. 9 shows an improved connecting means for headphone sets with sound baffling cups. The improvement combines the two branches of the connecting means, which previously depended from the sound baffling cups into one branch.

As shown in FIG. 9 according to one of its aspects the invention comprises an enclosure shaped like a hollow sheet extending in both the x direction and the z direction of the xz plane, the upper (188) and lower (190) surfaces of said sheet having a curvature (192) given by their divergence from the xz plane, such that said curvature may be defined as a function of the y co-ordinate of the xyz co-ordinate system.

Figure 10:
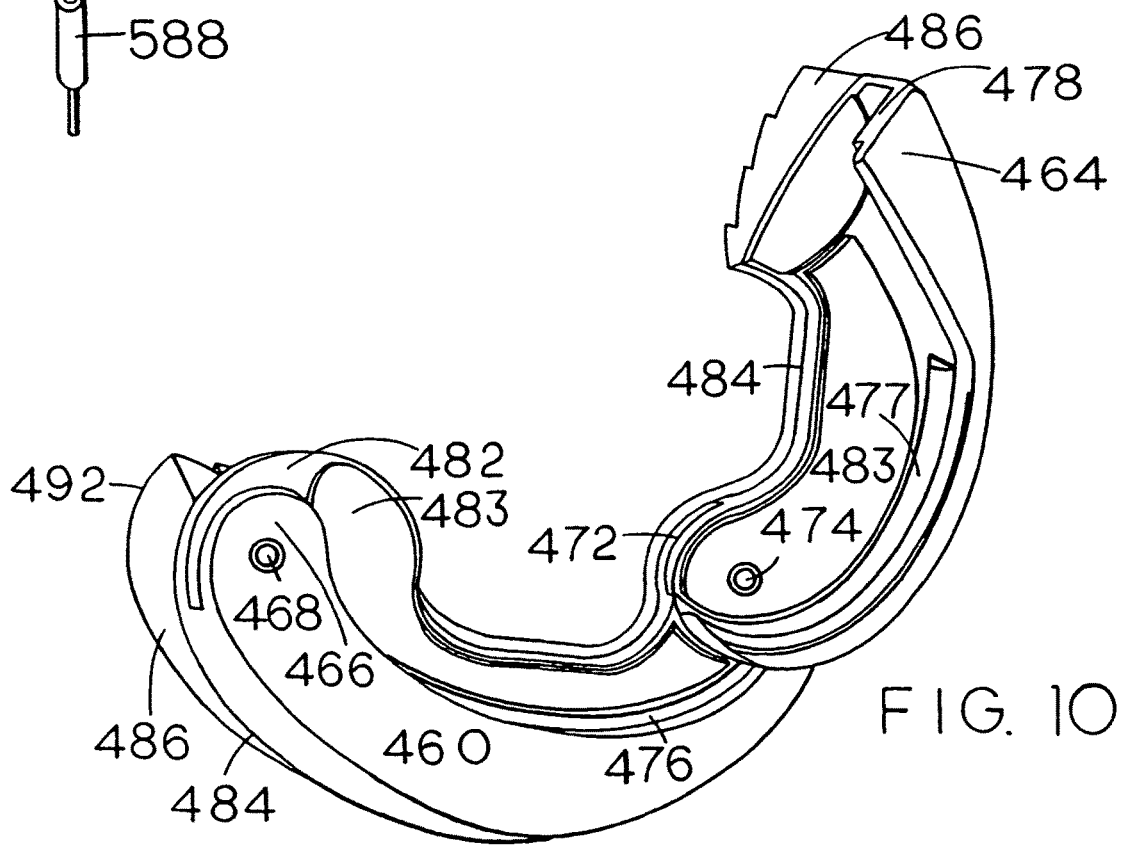
FIG. 10 is a separate view of the jointed clip. It shows the jointed clip in an opened position so as to give a better view of the grooves and tongues etc.

And as shown in FIG. 10 (A, B, C, D, E) according to another of its aspects the invention comprises an enclosure shaped like a hollow sheet extending in both the x direction and the z direction of the xz plane, the upper and lower surfaces of said sheet being substantially equidistant from each other and having a curvature given by a mathematical relationship defined in the xy plane, said relationship selected from the group consisting of a sinusoid curve, a sine curve (196), an inverse sine curve, a hyperbolic sine curve (198), a cosine curve, an inverse cosine curve, a hyperbolic cosine curve (208), a tangent curve (200), an inverse tangent curve, a hyperbolic tangent curve (202), a secant curve, an inverse secant curve, a hyperbolic secant curve (210), a cosecant curve (204), an inverse cosecant curve, a hyperbolic cosecant curve (206), a cotangent curve, an inverse cotangent curve, a hyperbolic cotangent curve (212), a logarithmic curve (214), a parabola (216), a semicubical parabola (218), a cubical parabola (220), a serpentine curve (248), a trajectory curve, a hyperbola (222), a rectangular hyperbola, an equilateral hyperbola, an ellipse (224), a circle, an evolute of an ellipse (226), an involute of a circle (228), an equiangular spiral (230), a hyperbolic spiral, a parabolic spiral, a spiral of Archimedes, a companion to the cycloid, a cycloid (232), a witch of Agnesi (250), a hypocycloid, a deltoid (236), an astroid, a nephroid, an epicycloid (234), a cochleoid (246), a stropheoid, a conchoid of Nicomedes, a folium of Descartes (244), a bifoleum (240), a lemniscate of Bemouilli, an n-leaved rose (242), an oval of Cassini, a limacon of Pascal (238), a cardioid, a cissoid of Diocles, a lituus, a tractrix (FIG. 13, 290), a power function curve, an exponential curve, a probability curve (FIG. 13, 292), a gamma function curve (252), a quadratic of Hippias (254). Each of these curves may be applied to the sheet, thereby comprising one of the embodiments of the invention. As shown in FIG. 10 (A, B, C, D, E), although the overall effect is three dimensional, when viewed along the length of the z-axis, the sheet describes the selected curve in the xy plane.

The sine curve (196) has the equation y=sin x. When the co-ordinate system is not applied the sine and cosine curves are indistinguishable. The same can be said for the secant and cosecant (204) functions. Tangent (200) and co-tangent functions differ to a greater degree. For sin h (198) we have; sin hx=$(e^x-e^{-x})/2$. Logarithmic (214) curves have the equation; y=$\log_a x$. A parabola (216), semicubical parabola (218), and a cubical parabola (220) have the equations, y=$x^2$, y=$x^{2/3}$, and y=$x^3$ respectively. The equation for the hyperbola (222) is also well known as $x^2/a^2 - y^2/b^2 = 1$. The equation for the ellipse (224) is also well known as $x^2/a^2 + y^2/b^2 = 1$, and where r=a=b, gives the equation of the circle as $x^2+y^2=r^2$. The evolute of the ellipse (226) is more complicated. The co-ordinates for the locus of points on the involute of a circle (228) are given by x=a cos @+a@ sin @ and y=a sin @-a@cos @. An equiangular spiral (230) is shown in the drawings, having the equation log r=a@. The witch of Agnesi (250) has an equation of y=$a^3/(x^2+a^2)$. The locus of the cycloid (232) with the cusp at the origin is given by x=a(1-sin @) and y=a(1-cos @). The deltoid (236) is a hypocycloid of three cusps whereas the astroid is a hypocycloid of four cusps. The general co-ordinates for the locus of an epicycloid (234) are given by x=(a+b)cos @-b cos ((a+b)@/b), and y=(a+b)sin @-b sin((a+b)@/b). A stropheoid, a conchoid of Nicomedes, and a folium of Descartes (244) are all curves having a very similar shape. The roses (242) may have the equations r=a cos n@ or $r^2$=a cos n@. The limacon of Pascal (238) and the cardioid are also similarly shaped having equations r=b+a cos @ and $(x^2+y^2-ax)^2=a^2(x^2+y^2)$, respectively. The gamma function (252) and the Quadratic of Hippias (254) are two unique multiple curve functions.

When these equations are used to determine a curvature for the enclosure the resultant appearance of the enclosure is a curved sheet that effectively follows a straight line in the z direction. However, it may sometimes be desirable to have a curvature in the z direction as well, thereby combining two curvatures. Essentially this involves combining the y co-ordinate of the above described curves defined in the xy plane with the y co-ordinate of a further curve selected from the same set of above described curves, but further defined in the yz plane. The combining of the two y co-ordinates may involve any method of generating a consistent combination.

Figure 11:
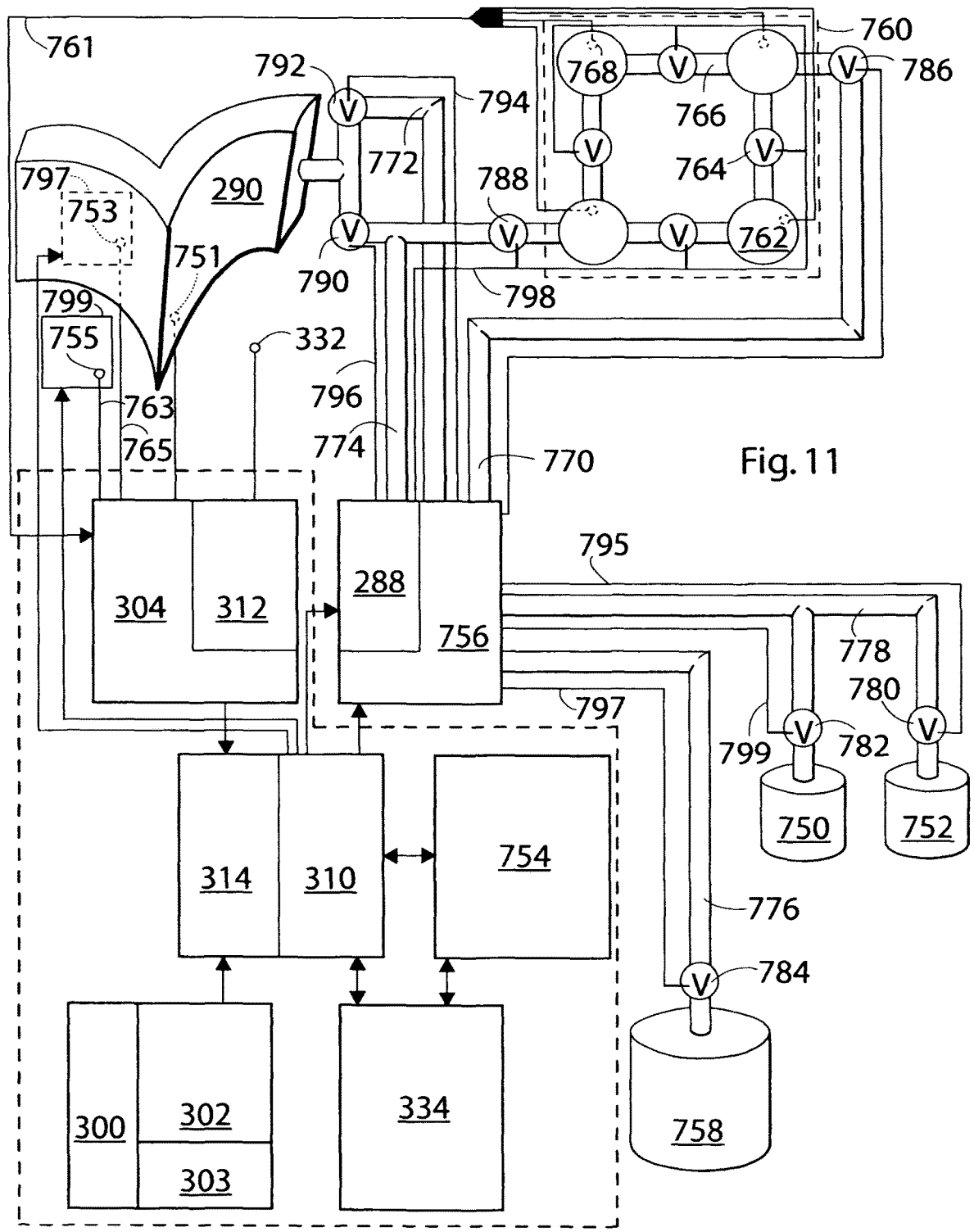
FIG. 11 shows the drawing of the preferred embodiment of the instant application. It illustrates how a large scale arrangement of enclosures may be combined to comprise aft a sound baffling device and how this sound baffling device may be used in conjunction with a controlling means having a controlling program, a microprocessor, and a neural net. Also it shows a pressure varying means, which contains a means for admitting and removing and is capable of admitting and removing fluids having different densities and acoustic impedances to and from the enclosure. This is further facilitated through the application of a vacuum capacitor. The sound-baffling device shown in this drawing should be capable of dynamically controlling the ambient sound.
Figure 12:
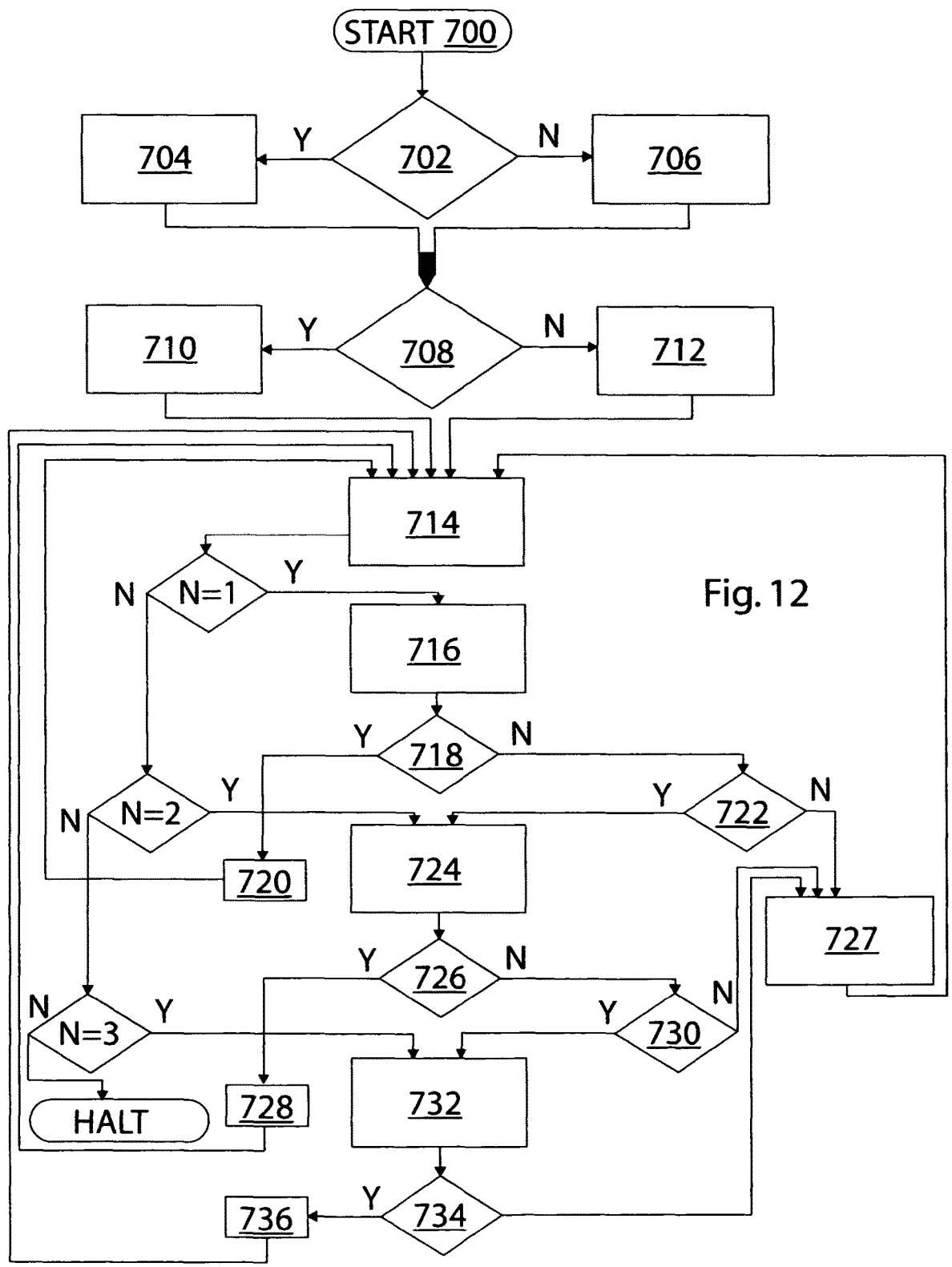
FIG. 12 shows one basic flowchart that comprises the description of a logic flow that may be used to organize the means for correlating, the pressure varying means (which includes the means for admitting and removing), a computer, and a neural net, to function in a logical and operational manner.

The enclosures shown in FIG. 11 exemplify this. The first (262) shows a parabola combined with a serpentine curve. The method of combination used here is addition. The second enclosure (264) is derived from the combination of two four leaved roses. The equation defining the roses in the xy-plane is the same as the equation defining the roses in the yz-plane, with the exception that the latter equation has z substituted for x in the former equation. The method of combination is by taking the average of the two y co-ordinates. A further enclosure (266) exhibits a rather convoluted shape. It is derived from the intersection of two tunnel like enclosures fashioned after the curvature of the Nephroid as defined in the xy-plane and the curvature of the astroid as defined in the yz-plane. The method of combination is by subtraction. Lastly we have the enclosure (272) produced by combining an involute of a circle with a folium of Descartes by means of division.

It should be noted that a perfect vacuum should not really attenuate sound, if one holds the word to mean decreasing the amplitude of the volume of the sound volume (This is usually achieved by absorption in a suitable medium). Rather the invention should to a substantial extent operate to increase the reflection of sound from the vacuum enclosure boundary.

Therefore, when enclosures of a preferred shape and having a preferred state of rarefaction within them are used to baffle sound a novel acoustic phenomenon results. The reflection from the incident surface is increased or decreased depending on the state of rarefaction. The lower the rarefaction the more sound is transmitted through the enclosure and the less is reflected. The greater the rarefaction the more is reflected and the less is transmitted. The baffles as shown therefore allow a portion of the incident sound wave to be divided between the paths of reflection and transmission. This unique splitting effect is what constitutes the characteristic novelty of these embodiments.

The key point here, is that while a sufficiently thin similarly shaped baffle made of the same material as the enclosure shell will cause a similar splitting of the incident wave, by adjusting the degree of rarefaction within the enclosure a much wider range of splittings may be obtained from the same material having the same curvature. And the curvature of the enclosure is a co-operating element in this combination. In a first instance this can be exemplified by considering the phenomena of the critical angle of reflection where the highest amount of the incident sound wave is reflected. At the critical angle, increasing the rarefaction of the enclosure should have less effect on the amount reflected as opposed to what one might expect at an angle that normally has a high percentage of transmission for the incident wave. The preparation of a preferred state of rarefaction within the enclosure therefore should not only change the overall percentage of what is transmitted versus what is reflected, it should also change the overall acoustic angular response characteristics of the enclosure in comparison to what one might expect from simply the uncombined shell material.

Since, as a rule the percentage reflected falls off to either side of the critical angle, it follows that a curvature will, by changing the angle of incidence for different loci of the curve, change the percentage reflected for these loci. When combined with the change in the overall acoustic angular response characteristics created by rarefaction this should allow for a range of unique, novel and unexpected results, much wider than previously possible by using the shell material on its own.

In summary, for a sufficiently thin shell material capable of sound transmission, increasing the rarefaction of the enclosure should result in a larger average reflected component than one would obtain by simply using a shell thickness of the shell material on its own. And the overall acoustic angular response characteristics of the enclosure should also be different from what the shell material would present on its own. When combined with a preferred shape, the shape and the rarefaction may co-operate to produce a range of novel results. And, taking this one step further, one could consider shell effects by taking into account the splitting of the incident longitudinal wave into a transverse and longitudinal wave upon entry into the solid structure of the shell. In short, the curvature is a co-operating element in the structure of the device.

It may therefore be preferable that the invention also has the capability to vary the amount and quality of the sound or thermal baffling provided. The key idea here is that because the presence of the vacuum within the enclosure should make the device essentially opaque to sound transmission, when matter is admitted to the enclosure sound transmission through the enclosure is enabled. And heat transmission should also vary to some extent, increasing as the pressure of the vacuum increases and decreasing as the pressure of the vacuum decreases. The amount of the sound or heat transmission should then be proportional to the amount of matter that is admitted. And the converse procedure applies as well. This is illustrated in one part of FIG. 13 according to which the invention further comprises a means for admitting and removing matter (288) connected to said enclosures (290, 292) by means of valves (294, 296), so that by admitting and removing matter to and from said enclosures the sound baffling characteristics of said sound baffling device are varied by said admitting and said removing.

The means for admitting and removing may use some type of vacuum pump to remove the matter from the enclosures. The vacuum pump may be motor driven or operated manually in some applications. After the matter has been removed from the enclosures, it can be readmitted by using the external pressure as a driving force. All that is required is a two-way valve. Such a valve could be used, in either manual or automatic operation, for either the admitting or removing of matter from the enclosures.

Accordingly, this embodiment exhibits the ability to baffle sound in a dynamic fashion. While this may have been done previously by rotating or moving the enclosures, the invention shows how the admitting and removing of matter to and from an enclosure may be used to baffle sound dynamically. In general admitting matter to the enclosure should decrease the sound baffling characteristics of the enclosure and removing matter from the enclosure should increase the sound baffling characteristics of the enclosure. It may therefore be preferable that said admitting increases the transmission of sound through the enclosures and said removing decreases the transmission of sound through the enclosures.

Most applications involving dynamic sound baffling will probably require more than one enclosure to effectively adjust the ambient sound. This follows from the fact that for many applications, such as the adjustment of temperature or acoustics in a theatre or lecture halls, the ambient thermal or acoustic environment is frequently changing. For example, the entry and exit of people to and from a lecture hall should change the values and characteristics of the ambient sound and temperature. A dynamic adjustment of the sound baffling characteristics of the sound-baffling device is therefore required to maintain the acoustic characteristics close to optimum.

In general the invention may be characterized as having three basic objects; the controlling of sound, the controlling of heat, and the controlling or creation of spatial configurations represented in the finished enclosures or contiguous aggregates of enclosures. A controlling means may therefore be used to control a general class of variable elements that effect the execution of the above named objects. A variable element may be defined as any element or sub combination of the invention that can be controlled to effectively vary the acoustic, thermal or geometric characteristics of the invention.

In operation the controlling means will at minimum have a plurality of default parametric values and characteristics combined with a plurality of default tolerances to guide it, and this may include both thermal and acoustic variables. The nature of the acoustic or thermal environment is then assessed by a means for measuring. The assessment results in the creation of a plurality of measured values and characteristics, and these may include both thermal and acoustic variables. After the means for correlating examines the correlation between these two pluralities the variable elements of the physical space are adjusted to improve the correlation. (In the case of volume transduction this could involve increasing or decreasing the amount of transduction. Or for frequency modulating bars residing in an tension and/or compression node this may mean increasing or decreasing the node separation to affirm or negate the effect of the bars.)

The operation of the controlling means is predictably in step with the plurality of default parametric values and characteristics. But the controlling means will also allow input parametric values and characteristics to be entered into its electronic memory. Should a different adjustment of the ambient sound be desired, a new plurality of input parametric values and characteristics can be entered by the user. If these are present, the controlling means will use the corresponding input parametric values and characteristics instead of the default parametric values and characteristics to do its calculation. This allows the operation of the controlling means to be adjusted to suit different user preferences (for different acoustic or thermal environments).

As previously discussed, the dynamic adjustment of a sound-baffling device is best handled by the controlling means. Accordingly, an embodiment of the invention which is designed to handle complex applications is illustrated in the greater part of FIG. 13, according to which the invention further comprises a controlling means (298), said controlling means having an input means (300) for entering and storing parametric values and characteristics (302), and;

said controlling means further having a means for measuring (304) the values and characteristics of the ambient sound, said means for measuring having sensor inputs (306, 307) placed throughout the extent of the physical space (308) which is governed by said sound baffling device, and;

said controlling means further having a means for correlating (310) said measured values and characteristics (312) of the ambient sound to said stored parametric values, and;

said means for correlating using the correlation (314) between said measured values and characteristics of the ambient sound and said stored parametric values as a benchmark for adjusting said means for admitting and removing of matter, such that matter is admitted and removed from said enclosures as indicated by said benchmark, so that the measured values and characteristics of the ambient sound throughout the physical space which is governed by said sound baffling device enter a convergence towards said stored parametric values, and;

after a requisite interval of time an optimum correlation between said stored parametric values and said measured values of the ambient sound is attained.

Alternatively, for the present filing a more concise description of this aspect of the invention may be as follows; The controlling means as now shown in the preferred embodiment of FIG. 11, further having an input means for entering and storing a plurality of input parametric values and characteristics, and;

said plurality of input parametric values and characteristics replacing said plurality of stored parametric values and characteristics in operation, so that said means for correlating uses the correlation between said plurality of measured values and characteristics and said plurality of input parametric values and characteristics as a benchmark for adjusting said variable elements of the physical space to improve the correlation, so that said plurality of measured values and characteristics enter said convergence towards said plurality of input parametric values and characteristics, whereby said optimum correlation between said plurality of input parametric values and characteristics and said plurality of measured values and characteristics is attained.

The underlying objective of the preferred embodiment is to allow the user of the sound-baffling device to choose the values and characteristics of the ambient sound to a degree closely corresponding to the users preferred values and characteristics for the ambient sound. The user may accomplish this by entering the preferred values and characteristics as the parametric values and characteristics of the ambient sound (302) into the input means (300), whereby they become input parametric values and characteristics. These values and characteristics may be any parameter that has been used or may be used to characterize the sound. However, the input means of some preferred embodiment may not accept the universal historical set of potential parametric values and characteristics. In such a case the parametric values and characteristics of the ambient sound accepted by the input means will be a subset of the universal parametric set of values and characteristics of sound.

Values and characteristics that may in general be accepted as parameters by the input means are, loudness, reverberation, and timbre. Further values and characteristics that may be settable are, pitch, attack, and decay. After the settable values have been entered they are compared to the measured values and characteristics (312) gathered through the means for measuring (304) which has sensor inputs (306, 307) that measure the parametric values and characteristics of the ambient sound throughout the physical space (308) governed by the sound baffling device. And the means for measuring will also have sensor inputs (761, 763, 765) for retrieving a pressure reading from inside the enclosures or chambers and for measuring the state of a node or force generating means. The comparison itself is carried out by the means for correlating (310) which should adjust the sound baffling device through the means for admitting and removing and/or the pressure varying means if it finds that the difference between the measured parametric values and characteristics and the selected parametric values and characteristics is sufficiently large as to require adjustment. The adjustment should then create parametric values and characteristics for the ambient sound that correspond more closely to the selected parametric values and characteristics of the ambient sound stored in the input means.

For more complicated scenarios a computer may be added to the controlling means. A computer is especially valuable when different types of performances should succeed each other in a theatrical environment, or if different types of thermal venues are desired at different times of day. For example a speaker may precede a musical performer or it is desired that the nighttime temperature should be cooler than the daytime temperature. In such a case more than one plurality of input parametric values and characteristics may be entered. The microprocessor will then read the input parametric values and characteristics when indicated and prompt the means for correlating to carry out the requisite adjustments. In general a controlling means also having a microprocessor is more adaptable to different performance scenarios and thermal adaptations. Knowledgeable product support staff should be able to add subroutines to suit ongoing requirements and difficulties.

Also, in complex acoustic or thermal environments having many shaped enclosures, the large number of variable elements and effects presented make the registers and memory banks of a computer a tremendous convenience. Pluralities of input parametric values and characteristics can be stored as presets and/or in other appropriate file formats. Later they can be recalled by loading or during program operation, thereby making the tuning of large thermal or acoustic systems feasible. The knowledge of how to program these problems is readily available in the computing science and acoustic arts; acoustic ray tracing and acoustic pyramid tracing programs are commercially available. And they are even available as freeware.

Therefore, according to another of its aspects the invention comprises the controlling means as shown in the preferred embodiment of FIG. 11, further having a microprocessor governed by a controlling program, said controlling program enabling a computer simulation of the physical space governed by said controlling means, said model devised to operate in accordance with the principles of science, and;

said controlling program capable of calculating a plurality of predicted values and characteristics which should result from adjusting said variable elements, and;

said controlling program further using the correlation between said plurality of predicted values and characteristics and said plurality of stored parametric values and characteristics to create a second benchmark, and;

said controlling program using said second benchmark to calculate instructions for said means for correlating, and;

said means for correlating using said instructions to adjust said variable elements of the physical space, so that said plurality of measured values and characteristics enter a convergence towards said plurality of input parametric values and characteristics, whereby an optimum correlation between said plurality of stored parametric values and characteristics and said plurality of measured values and characteristics is attained.

The technology used to implement the controlling means (298) may be based around a microprocessor governed by a controlling program designed specifically for this task. While optional, the controlling program and microprocessor effectively should augment the means for correlating while the other means may be implemented by dedicated hardware. The input means may simply be some kind of data entry console as exemplified by a PC terminal and keyboard. Or it may be a set of switches in conjunction with LED readouts or dials, as may be deemed most appropriate for a particular design. The means for measuring should have sensors for testing the ambient sound, the most obvious of which would of course be microphones (332, 333) placed strategically throughout the physical space which is governed by the sound baffling device. Also the means for measuring should have pressure or rarefaction sensors (751, 768) within the enclosures or various chambers etc., and transducers (753, 755) for sensing the state of a node or force generating means. The information from these sensors may then be converted into a digital representation useable by the means for correlating in carrying out the comparison of the values and characteristics of the ambient sound. And this digital representation should also be useable by the controlling program and the microprocessor (334).

The controlling program should contain a thermal or acoustic model of the physical space under consideration. This model is derived from, and constructed in accordance with the principles of thermal or acoustic science and includes the effects of the placement and shape of the enclosures (290, 292) on the values and characteristics of the ambient sound or temperature. And this model is also capable of estimating the effects of various amounts of matter present within the enclosures on the ambient sound. By using this model and the input parametric values and characteristics as a basis for the initiation of calculations, the controlling program should be able to estimate the appropriate level of matter that should be present within each of the enclosures. Subsequent to the calculation of this estimate, the controlling program and the microprocessor should then generate the necessary set of instructions for the means for admitting and removing and/or the pressure varying means.

Alternatively, a neural net (754) may be used instead of or in conjunction with a microprocessor. The neural net could be computer based but it may be preferable to have it hardwired. One advantage of a neural net is that it may be more compact and have a faster response time than a microprocessor. The knowledge of how to construct a neural net is readily available in the computing science arts. A hard wired neural net can be constructed by using a programmable read only memory chips (PROM) or an erasable programmable read only memory (EPROM) in combination with a broad array of devices and systems such as Programmable Logic Controllers (PLC), Programmable Logic Devices (PLD), Programmable Array Logic (PAL), Field Programmable Gate Arrays (FPGA), Application Specific Integrated Circuits (ASIC), System-on-Chip (SOC), and Complex PLD (CPLD) that can be utilized for digital logic implementation and control.

Also Field Programmable Gate Arrays (FPGAs) can be employed to standardize functionality formerly performed by a CPU, and to create custom capabilities (e.g. science domain specific massively parallel data compression). Programmable logic software can be tested for functionality, boundary conditions, and operational simulation by adapting existing methods such as Fagan and Gibbs inspection of software at the Design Review level, as well as for Quality Assurance. A (Very Large Scale Integration; VLSI) hardware design language that is particularly suited as a language for describing the structure and behavior of digital electronic hardware designs, such as ASICs and FPGAs as well as conventional digital circuits could then be used to create the hardwired neural net. Or the neural net could simply be software based and could then be operated in conjunction with the microprocessor.

Therefore, according to another of its aspects the invention comprises the controlling means as shown in the preferred embodiment of FIG. 11, further having a neural net enabling an electronic simulation or computer simulation of the physical space governed by said controlling means, said electronic simulation or computer simulation devised to operate in accordance with the principles of science, and;
  said neural net capable of calculating a plurality of alternate predicted values and characteristics which should result from adjusting said variable elements, and;
  said neural net further using the correlation between said plurality of alternate predicted values and characteristics and said plurality of stored parametric values and characteristics to create a third benchmark, and;
  said neural net using said third benchmark to calculate instructions for said means for correlating, and;
  said means for correlating using said instructions to adjust said variable elements of the physical space, so that said plurality of measured values and characteristics enter a convergence towards said plurality of stored parametric values and characteristics,
  whereby an optimum correlation between said plurality of stored parametric values and characteristics and said plurality of measured values and characteristics is attained.

The construction of neural nets is well known in the art. Rudimentarily, there are three main types of nets:
  1. A multilayer net using back propagation
  2. A Hopfield net
  3. A Kohonen net It follows that the combinations of controlling means, microprocessor, and neural net, may be used to control the variable element discussed below. This class of variable elements may, in its basic form, be comprised of the force generating means in all their variations, certain nodal means having an active effect on the attaining of the above named objects, and energy transfer elements, such as transducers, that have a specific and useful technical function. We list the energy transfer elements as follows:
  1. enclosure transduction circuit—changes the sound output emanating from the enclosure wall distal to the sound source; generally resides in a transduction node
  2. frequency modulating bars or disks—this is simply a grouping of bars or disks mounted on a column or strut that the frequency of the sound traveling through it.
  3. valves—these are simply valves that can be used to regulate the homogeneous fluid matter flow from a means for admitting and removing or a pressure varying means to and from the enclosures as required by a controlling means.
  4. tension and/or compression node—these are node having the ability to expand or contract the enclosure
  5. retracting nodes—these are nodes having the ability to retract within or without an enclosure thereby creating a nodal gap so that the transmission of sound or thermal energy across the nodal gap is substantially barred
  6. actuator—usually allows force to be applied linearly and usually relies on an electric (magnetic), hydraulic, or pneumatic force to provide the actuation.
  7. electric motor—this may be used to rotate or translate the enclosure. Or it may be used to tighten or loosen lines or move levers or operate a hydraulic or pneumatic reservoir for hydraulic force generating means or a pneumatic force generating means
  8. force generating means—these means change the geometric, thermal, or acoustic properties of an enclosure
  9. RF transmitter—this can be used to provide measured values and characteristics to the controlling means and can be used to receive information and instructions for active elements in the enclosure from the controlling means It may therefore be preferable that according to one of its aspects the invention further comprises a variable element that is selected from the group consisting of a noise canceling transducer, a transduction circuit, frequency modulating bars, frequency modulating disks, a retracting node, an tension and/or compression node, a valve, an actuator, and an electric motor.

It may therefore be preferable that the enclosures also have an enclosure transduction circuit. The enclosure transduction circuit should have an input signal transducer (800, 801), which should usually be a piezoelectric transducer, although it may also be a contact transducer, a magnetic transducer, or possibly a microphone, as suitable for a specific application. The enclosure transduction circuit should also have at least one output signal transducer (804) which should usually be a matched piezoelectric transducer, but could also be a contact transducer, a magnetic transducer, or possibly a speaker as may be suitable for a specific application. It should be preferable to match the input and output transducer to achieve a matched pair. By 'matched' is meant the optimum companion transducer, one that necessitates the least electronic circuitry and manipulation to achieve the desired result. The transducers should be mounted on or in a supporting strut or column (806) or in the frame (808) of the enclosure, in what should generally be called a transduction node. These transducers should be manufactured to pick up or emit sound, in the audible range, to a reasonable degree of fidelity. The input signal transducer should be mounted in that part of the supporting strut or column or frame, which first receives the incident or direct sound wave (802) traveling through the physical space under consideration. The output signal transducer should then be mounted behind the input signal transducer ('Behind' means that the direct sound wave reaches the input signal transducer first), the exact positioning to be determined by the type of enclosure transduction circuit.

There are five basic enclosure transduction circuits: noise canceling, sound canceling, modulation, modulated noise canceling, and modulated sound canceling. And when structural frames and columns composed of materials having different acoustic impedances are used another five derivative transduction circuits may be formed.

Figure 13:
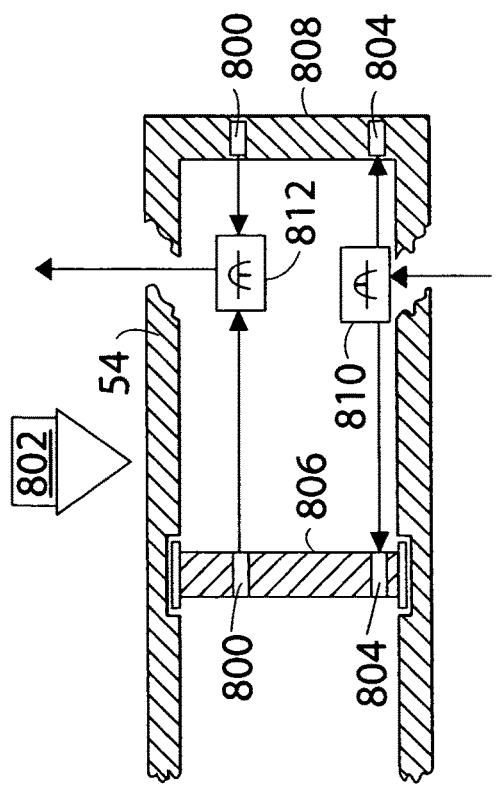
FIG. 13 shows a noise canceling transduction circuit.

A noise canceling circuit may be created, as shown in FIG. 13, by placing the output signal transducer shortly behind the input signal transducer, so that unwanted noise is removed from the input signal (810). Noise canceling circuits have been shown before, but to the applicant's knowledge, they have not been used to cancel noise in a solid. The noise canceling transduction circuit will send the input signal to the microprocessor or the neural net, where the input signal is treated to comprise the output signal (812). As can be seen by examining (810 and 812), the output signal contains a bar of noise that will cancel the bar of noise in the input signal. This results in a substantially noise free waveform for any sound that continues to travel through the frame and/or the supporting strut.

If structural frames and columns composed of materials having different acoustic impedances (Normally, for increasing internal reflection, the characteristic impedance of the material facing the direct sound wave is chosen to be at least or about one tenth the characteristic impedance of the backing material) are used, then the noise canceling circuit will be placed in the facing material before the join to the material of higher acoustic impedance.

Alternatively, the enclosure may comprise a sound canceling circuit. This circuit should normally be added to structural nodes in an enclosure with the intent of preventing substantial sound transmission through the supporting columns or crossbars of the structural nodes, and/or the frame of the enclosure. In this application the music or ambient sound picked up by the input transducer is characterized as noise by the microprocessor or neural net. As a result the output signal is calculated by the microprocessor or neural net to exactly cancel the input signal as created by the direct sound wave. This should result in substantially total sound cancellation in the supporting columns or crossbars of the structural nodes, and/or the frame of the enclosure.

If structural frames and columns composed of materials having different acoustic impedances are used, then the sound canceling circuit will be placed in the facing material before the join to the material of higher acoustic impedance.

For rudimentary acoustical considerations, only four basic variables should require consideration; the listening level which is the volume of sound experienced by an audience member during a performance, the initial time delay gap, which is the delay of the first reflection measured from the time of arrival of the direct sound wave at a listening point, the reverberation time which is defined as the time necessary for a decay of 60 DB of the sound field after the sound source has been turned off, and the inter aural cross correlation which is defined as the maximum value of the normalized cross-correlation function of two impulse responses measured by two microphones placed in a dummy head's auricular lobes. These variables should also be included in the list of default parametric values and characteristics, and be settable by the input means as input parametric values and characteristics. It may therefore be preferable that the enclosure transduction circuit is also used to modulate these variables when desirable and feasible.

To carry out modulation of these and other variables the input transducer should generate an input signal that is then analyzed by the microprocessor and/or neural net. It may usually be preferable to put the input signal through an analog to digital converter. After the input signal has been converted to digital form it may be modified to exhibit preferred characteristics that are then combined with the input signal to generate the output signal. The output signal is then applied to the output transducer. In this way the enclosure may, in addition to reflecting, absorbing, and refracting the sound, also add preferable features such as a change in volume, a change in the initial time delay gap, a change in the inter aural cross correlation, a change in pitch (pitch bend), a change in timbre, a change in harmony, a change in reverberation time, and a change in meter or rhythm (possibly by adding a beat).

In particular the volume may be increased by increasing the volume of the output from the output transducer. The inter aural cross correlation can be affected by varying the output signal from the output transducer between two enclosures on opposite sides or in different parts of the physical space under consideration. The initial time delay gap can be modified by playing an output signal from the enclosure before it would normally be played in that part of the physical space where the enclosure resides; this requires that an earlier version of the signal be sent from the microprocessor and/or neural net combination to the enclosure directly before the direct sound wave actually arrives in the vicinity of the enclosure. This would normally be done by using the input signal from an enclosure that is closer to the sound source, performing the appropriate modifications on this input signal and then sending the produced output signal to the more distant enclosure where it is applied to the output transducer. Similarly, an output may be produced by the enclosure after the sound source is turned off, and thereby affect the reverberation time.

If structural frames and columns composed of materials having different acoustic impedances are used, then the sound modulating circuit will preferably be split, with the input transducer residing in the facing material before the join to the material of higher acoustic impedance, and the output transducer residing after the join in the material of higher acoustic impedance.

The sound modulating circuit can be combined with the sound canceling transduction circuit above to create a modulated sound canceling transduction circuit. This means that the incident sound is substantially cancelled out of the supporting struts and frame of the enclosure so that the sound added by the output transducer, if any, is substantially created by the microprocessor and or neural net. The combined circuit should then be called a modulated sound canceling transduction circuit. The modulating transducer is placed last in line with regards to the direct sound wave; this enables it to add sound generated by the microprocessor and/or neural net after the direct sound in the columns or frame of the enclosure has been substantially eliminated.

If structural frames and columns composed of materials having different acoustic impedances are used, then the modulated noise canceling transduction circuit will preferably be split, with the input transducer residing in the facing material before the join to the material of higher acoustic impedance, along with the output transducer, while the modulating transducer resides after the join in the material of higher acoustic impedance.

This sound modulating circuit can be combined with the noise canceling transduction circuit above. This means that the extraneous noise is substantially cancelled out of the supporting struts and frame of the enclosure. The combined circuit should then be called a modulated noise canceling transduction circuit. The modulating transducer is placed last in line with regards to the direct sound wave; this enables it to add preferred acoustic information generated by the microprocessor or neural net after extraneous noise in the columns or frame of the enclosure has been substantially eliminated.

If structural frames and columns composed of materials having different acoustic are used, then the modulated sound canceling transduction circuit will preferably be split, with the input transducer residing in the facing material before the join to the material of higher acoustic impedance, along with the output transducer, while the modulating transducer resides after the join in the material of higher acoustic impedance. Noise reduction and cancellation has had extensive treatment in the art and may also be extended to using RF tags.

It may therefore be preferable to use radio frequency technology as exemplified by RF tags. This technology may be implemented to provide a more convenient construction of the sensor network required by an ensemble of enclosures connected to a controlling means, as exemplified by the use of transducers in combination with a controlling means above. The use of RF tags is simply substituted for the use of wires connected to sensors.

As shown in U.S. Pat. No. 5,457,447, RF technology or transmitted energy may also be used to supply power to an RF tag that may be used to comprise a sensing circuit as may be preferable in some applications, in particular to provide measured values and characteristics to a means for measuring. And as shown in U.S. Pat. Nos. 6,107,917 and 6,061,614, RF technology is also capable of using RF tags to receive instructions from the controlling means and in turn is equally capable of returning requisite information to the means for measuring. These prior art of these patents can therefore be used in the RF tags of the present invention and the disclosures of said patents are accordingly incorporated herein in their entirety by reference.

Therefore it may be preferable that the enclosures also comprise RF tags powered by line current or, alternatively coupled to an RF powered power source capable of providing the power needs of the RF tags. And it may further be preferable that the RF tags receive and execute instructions from the controlling means and send measured values and characteristics to the means for measuring as required in the effective operation of the invention.

Although the enclosure could also be considered a variable element, since it is usually the recipient of an action (e.g. A change in the level of rarefaction created through the actions of a means for admitting and removing) it is generally not considered so. The actual element that carries out the action is considered to be the variable element, since this is the element that will receive instructions from the means for correlating. And for the enclosure the primary element that usually carries out actions on the enclosure is the force generating means (799). These fall into three main categories, force generating means that change the geometrical properties of the enclosure by transforming a flexible enclosure into a different shape, force generating means that change the acoustic properties of the enclosure, and force generating means that change the thermal properties of the enclosure. Of course changing the shape of the enclosure may change the acoustic properties and thermal properties as well. In this regard, the most elementary transformations of the acoustic properties and the thermal properties of course depend on simply changing the energy conductivity of the enclosure with regards to the relevant energy, sound for the acoustic properties and heat for the thermal properties. This can be done by, instead of using a pressure varying means or a means for admitting and removing, simply changing the amount of contact between the enclosure walls or between nodes in the enclosure walls.

According to another of its aspects the invention is embodied as an enclosure comprising a force generating means, so that the geometrical properties of said enclosure, or the acoustic properties of said enclosure, or the thermal properties of said enclosure, can be varied by said force generating means. And the enclosure may also contain a homogeneous fluid for attenuating sound or heat, and further comprise a pressure varying means.

The homogeneous fluid for attenuating sound or heat will of course be effective for preventing both heat and sound transmission through the enclosure. As has been discussed elsewhere, the effect of varying the homogeneous fluid for attenuating sound or heat in the enclosure should be to change the impedance of the enclosure for both heat and sound. A sound absorbing material applied to the rear wall of the enclosure would therefore add sound absorbing characteristics when the impedance of the enclosure is minimum. That is to say, when the enclosure is placed against a wall with the sound absorbing material facing the wall and the impedance is high, the sound will be largely reflected from the enclosure. But when the impedance is low the sound will travel through the enclosure and be absorbed by the sound absorbing material.

Therefore according to one of its aspects the invention comprises; an sound absorbing material contacted to a wall of said enclosure, so that when the impedance of said enclosure is minimized, the sound absorbing characteristics of said enclosure are substantially increased.

Alternatively, the sound absorbing material could also be placed into the interior of the enclosure, as long as the sound absorbing material is prevented from contacting the enclosure walls directly when the impedance of the enclosure is high. Or the sound absorbing material could be placed between two enclosures that can be controlled independently. When both enclosures exhibit a high acoustic impedance the sound absorbing material has little or no effect on the ambient sound. When one enclosure exhibits a high acoustic impedance and the other enclosure does not, the side of the embodiment where the enclosure has a low acoustic impedance experiences significant sound absorption. And for a setting having an intermediate impedance some sound will be reflected while other sound will be absorbed. By varying the impedance the user of the invention will be able to choose between levels of absorption and reflection with this embodiment. This embodiment is therefore preferably used when the enclosure is hanging freely in the physical space under consideration, since it allows the sound to be absorbed or reflected from either side, as may be preferable.

Therefore according to another of its aspects the invention comprises; a sound absorbing material contacted on a first side to a wall of a first enclosure, said sound absorbing material contacted on a second side to a wall of a second enclosure, so that when the impedance of said first enclosure is minimized, said sound absorbing material substantially absorbs the sound traveling through said first enclosure, and when the impedance of said first enclosure is maximized, said first enclosure substantially reflects all of the sound in the direct wave, and;

when the impedance of said second enclosure is minimized, said sound absorbing material substantially absorbs the sound traveling through said second enclosure, and when the impedance of said second enclosure is maximized, said second enclosure substantially reflects all of the sound in the direct wave;

whereby sound can be variably reflected or absorbed. Similarly, a single enclosure having flexible walls could be wrapped around a length of sound baffling material. Although this enclosure would not have variability on two sides, it would have the same variability on both sides.

It may also be advantageous to maintain surface tension across these walls to retain optimum reflective properties when a distending or contracting force is applied. This may be done by adding a resilient border to the perimeter of the enclosure. A resilient border may be made from stainless steel spring wire or a flexible plastic moulding, or hydraulic or pheumatic tubing under pressure. But the footprint of the border should be minimized to avoid interference with the ambient sound.

It may therefore be preferable that according to one of its aspects the invention further comprises; an enclosure having at least one flexible wall, said enclosure further comprising a resilient border for maintaining an optimum surface tension across said at least one flexible walls, so that said at least one flexible wall presents a smooth reflective surface to the incident sound.

When the enclosure has flexible walls, the border may also be comprised of a pneumatic force generating means in combination with a spring force generating means. The spring force generating means is used to retract the enclosure when not in use and the pneumatic force generating means is uses to extend the enclosure for use. In some embodiments the pneumatic force generating means may also be used to fashion a resilient border.

In general for an enclosure to be effective it is necessary incorporate a force generating means into the enclosure. This is because in use, when the enclosure is evacuated, large pressures should be counterbalanced to maintain the structural integrity of the enclosure. Alternatively, when the enclosure is pressurized, large internal pressures should be counterbalanced to maintain structural integrity. While this may be done by building a sufficiently sturdy enclosure with strong supporting struts, braces, and crossbars, in practice it is preferable to produce enclosures that are of light construction and minimize the amount of material used to construct the enclosure walls.

The reason for this is simply that the maximum benefit of the active medium in the enclosure is obtained when the impact of the enclosure walls and frame on the ambient sound and the direct sound wave is minimized. Since the absorption of sound energy or thermal energy is proportional to the thickness of the walls, the thinner the walls, the less sound energy or thermal energy will be stored or absorbed in the walls. (Of course sound energy is converted into thermal energy on absorption.) And thermal energy will be stored and potentially later released when the ambient temperature drops below the temperature of the walls. Therefore it is desirable to minimize the wall thickness as much as possible while still ensuring that the enclosure retains its hermetic properties.

The walls therefore should be thin but the option of having them structurally fixed or flexible remains. Of course a wall that is sufficiently thin will tend to be flexible and will twist or buckle under the application of pressures. If the wall is intended to be fixed then supporting struts applied at appropriate intervals will remedy the problem. These supporting struts could be internal or external but because of the tendency for external structures to interfere with the transmission of sound it may be preferable to have the supporting struts internal. For purely thermal applications it may on occasion be preferable to have the supporting struts for the enclosure applied externally.

Supporting struts may be considered to be the first of a large number of force generating means that can be applied to the enclosure either singly or in combination. The actual force generating means to be applied will vary depending on the type of enclosure, whether it is an enclosure having flexible walls, or whether it is an enclosure having fixed walls. The majority of force generating means may be applied to enclosures having flexible walls and may in general comprise the use of tension and/or compression nodes, while force generating means applied to fixed wall enclosures may in general comprise the use of retracting nodes. And simple rotation or translation of the enclosure may also be carried out by a force generating means.

The actual force generating means may be applied internally or externally. But it should generally be preferable to apply the force generating means internally to the enclosure to minimize interference with the direct sound wave. The one exception is of course the line force generating means, which is in general applied externally.

In creating the enclosures it is important that the stress that may be placed on the components be taken under consideration. Stress can cause shear failure and must be considered in selecting and sizing materials for any construction that requires the handling of large forces. And depending on the degree of evacuation or internal overpressure, the enclosures may indeed have to handle large forces.

In fact, just one square foot of a sound baffle will have over a ton of pressure on it under full evacuation. The way of dealing with this may of course be by simply dividing the pressure or force over a large number of supporting struts. For a square foot of a sound baffle this might be done by using 144 supporting struts that would then deal with a pressure of 14.7 lb. P.S.I. each, under full evacuation. At one half atmospheric the pressure would be less, or about 7.35 lb. P.S.I. In any event it would be preferable to use fewer supporting struts, if possible.

A few simple stress hints might be appropriate here, although more comprehensive information can be found in (R. J. Roark and W. C. Young, Formulas for Stress and Strain, 5th ed., New York, McGraw-Hill, 1975). To begin with, the actual strut would normally not have a one square inch cross section; a rectangular strut cross section is just base times height (b×h) or width times length, and a circular strut cross section is given by $\pi d^2/4$. The compressive stress is then given by $o=F/A$, where F is the pressure or force on the strut.

Therefore a one eight inch diameter strut carrying one square inch of the enclosure surface at 14.7 P.S.I, would have about 14.7/0.01127=1198 P.S.I. of pressure exerted on it. The procedure in selecting the size of the strut must then comprise the taking of a value at about or below the experimentally determined maximum stress and shear specifications of the material under consideration for use as a strut or column, and then dividing the maximum force to be borne by that value. For aluminum a rough figure of about 20000 lb. is known, and using the formulas we obtain 14.7/20000=0.000735. Plugging this into $d^2=4(0.000735)/\pi=0.0009358$ we obtain 0.031 inches for the diameter of this strut made of aluminum. Since this is quite small one would likely prefer to have an aluminum strut carry more than one square inch of the enclosure surface.

A one-quarter inch strut might be preferable. Therefore we divide 0.25/0.031=8.0645 or roughly a carrying capacity of eight square inches of the enclosure surface. Checking we obtain 14.7(8)/20000=0.00588, and $d^2=4(0.00588)/\pi=0.07389$, giving 0.27 inches for the diameter of this strut made of aluminum when carrying eight square inches of the enclosure surface under full evacuation. This is somewhat different from the 0.25 inches that we aimed for because it was found convenient to use rounded values for the numbers in the calculations. Therefore rounding error should account for the difference. In any event the numbers agree closely enough to exemplify how to approximate an accurate size for the strut or column.

When the enclosure is put into overpressure so that the internal pressure is greater than atmospheric tensile stress should result. For struts or columns this is calculated in the same way as compressive stress but with the opposite sign. And it may be preferable that the overpressure is no more than about two atmospheres.

Also, especially for rigid or semi-rigid enclosures having fixed walls it is important to avoid the creation of moments. Therefore, in these embodiments, it is important that the struts and the frame of the enclosure are built to be perpendicular to the enclosure surface. Any deviation from the ninety-degree angle between the frame or columns and the surfaces of the enclosure will cause a moment to be created, and the greater the angle the bigger the moment. The effect of the moment is to create a twisting force about the neutral axis of the frame or the strut; this could cause the enclosure to collapse. Therefore care should be taken to construct the frame at right angles to the walls and to construct the struts at right angles to the walls. And the same principle applies to all the force generating means; the strut merely being the most elementary.

There may also be the problem of direct shear. The experimental values for direct shear will, in general, be different from those for tensile or compressive stress. But the basic formulas may be as shown above. Stress is a complicated phenomenon, but fortunately it has been well studied, and for complicated calculations the literature must be consulted. Direct shear may occur in the enclosures where the walls are buttressed by the columns or frame. In this case the area will be the cross sectional area of the wall under consideration and we can multiply the length of the wall by the thickness of the wall to obtain the cross section. So for a one foot long, three eighths inch thick section of wall we would obtain a cross section of about 0.03125 of a square foot. If the relevant wall surface carries twenty four square inches up to the next supporting members (struts) then we would have 176.4/0.03=5880, or 6000 pounds per square foot (rounded) or about one quarter of the maximum safe limit for aluminum (We're only counting one half of the twenty four square inches because the other half is carried by the next supporting members.

And there may also be the problem of bending stresses. This would arise for enclosures having fixed walls, and would be caused by the compression or tension that may be experienced by an enclosure wall section between two supporting struts. The center of the wall section should tend to bend in or out thereby subjecting itself to bending stress.

For flexible walls and enclosures more complicated calculations may be necessary. However in all cases the cross-section required for the instant member can be calculated by looking up the maximum value of the selected stress resistance for the material desired and then dividing the force carried by the instant member by said maximum value. This should give the minimum cross-section required for the instant member to avoid failure. In practice it is of course preferable to not use the minimum cross-section, but rather a cross-section somewhat larger than that.

A basic list of force generating means is as follows:
1. An electric force generating means; this type of means creates a repulsion or attraction, which may be the result of an electrostatic force or a magnetic force, generated by electromagnets or electrostatic plates to push or pull the flexible walls apart, and thereby creates a vacuum within the enclosure. An advantage of the electric force generating means should be that the elements creating the repulsion or attraction are not in contact with one another after repulsion or attraction takes place and therefore should not be able to conduct sound or temperature directly. Alternatively, when located within or without an enclosure having fixed walls it may be used to operate a retracting node.
2. A hydraulic force generating means; this type of means uses miniature hydraulic jacks or tubes for creating hydraulic force to push the flexible walls of an expanding enclosure apart, and thereby creates a vacuum within the enclosure. Alternatively, when located in an enclosure with fixed walls it may be used to operate a retracting node. When located externally it can also be used to pull the enclosure walls apart by using hydraulic actuators etc.
3. A pneumatic force generating means; this type of means uses miniature pneumatic jacks or tubes for creating pneumatic force to push the flexible walls of an enclosure apart, and thereby creates a vacuum within the enclosure. Alternatively, when located in an enclosure with fixed walls it may be used to operate a retracting node. When located externally it can also be used to pull the enclosure walls apart by using pneumatic actuators etc.
4. A lines force generating means; this type of means uses lines to pull the flexible walls apart, and thereby creates a vacuum within the enclosure. It is also used to control and preserve the orientation of an enclosure and can be used inside an enclosure to exert inward tension on the enclosure walls.
5. A spring force generating means; this type of means uses a spring to push the flexible walls apart, and to support fixed walls. Thereby it may create and maintain a vacuum within the enclosure. When located in an enclosure with fixed walls it may be used to operate a retracting node. Externally, it can also be used to pull the enclosure walls apart.
6. A lever force generating means; this type of means uses levers to pull the flexible walls apart, and thereby creates a vacuum within the enclosure. It generally should be used externally to the enclosure, although a system of interacting levers can also be used internally.
7. A supporting strut or column force generating means this type of means uses a strut or column to brace the enclosure walls. The strut usually should have a preferred acoustic construction comprising a boundary reflective layer to reduce direct sound transmission through the strut. However, struts can also be used externally as bracing to hold the enclosure walls apart. For more sophisticated results it may be preferable to combine two or more force generating means to achieve a composite result.

Therefore, according to another of its aspects the invention should comprise a force generating means selected from the group consisting of an electric force generating means, a hydraulic force generating means, a pneumatic force generating means, a line force generating means, a spring force generating means, a lever force generating means, and a strut force generating means.

In particular the electric force generating means may use an electrostatic repulsive force or a magnetic repulsive force, generated by electromagnets or electrostatic plates to push or pull the flexible walls apart, and thereby creates a vacuum within the enclosure. But it may also take the form of a solenoid, an electric actuator, or an electric motor. An electric force generating means is usually used in an expanding enclosure having tension and/or compression nodes in combination with flexible plastic, rubber, or aluminum sheeting to comprise the surface or walls of the enclosure, although any other flexible sheeting capable of being formed to comprise a hermetic enclosure may be used as well. The electric force generating means may be used to counteract the internal pressure applied to the enclosure when the homogeneous fluid within the enclosure is at greater than atmospheric pressure due to the action of the pressure varying means. An advantage of the electric force generating means should be that the elements creating the repulsive force should not be in contact with one another after repulsion takes place and therefore should not be able to conduct sound or temperature directly. Conversely, when the electric force generating means is used to create an attraction, the attraction may not be strong enough to create contact between the enclosure walls so that transmission through the enclosure is not increased by said attraction. In this case the attraction would normally just be sufficient to balance the internal pressure. And the electric force generating means should usually be used just to counteract the external pressure applied to the enclosure when the homogeneous fluid within the enclosure is rarified.

In general, an internal electric node will preferably be comprised of a solenoid or an electric actuator. These may be anchored to a nodal base, which is made from a resilient material anchored to the inside of the enclosure wall. When power is applied the resultant electric force generating means may push the enclosure walls apart, thereby creating the vacuum. Alternatively, when located inside or outside an enclosure with fixed walls the electric force generating means may be used to operate a retracting node and apply whatever stabilizing force is necessary to maintain the stability of the enclosure. And when the electric force generating means is used externally, it generally pulls flexible walls apart, although when the power polarity is reversed it can also be used to push or pull flexible walls together.

The hydraulic force generating means may be comprised of a plurality of conduits, tubes, or hydraulic lines for the hydraulic liquid. The hydraulic force can then be applied by placing the hydraulic liquid under pressure. The hydraulic force generating means may be used to create a distending or contracting force on the enclosure wall by means of internal or external hydraulic lines, or by external hydraulic jacks, or by miniature internal hydraulic jacks, or hydraulic actuators, or hydraulic lines, or hydraulic plates. so that the flexible enclosure walls could be moved apart, thereby creating said vacuum. A hydraulic force generating means is usually used with an enclosure having flexible walls and tension and/or compression nodes in combination with flexible plastic, rubber, or aluminum sheeting to comprise the surface or walls of the enclosure, although any other flexible sheeting capable of being formed to comprise a hermetic enclosure may be used as well. Varying the distending or contracting force should vary the degree of distension. The hydraulic force generating means may simply comprise conduits, tubes, or hydraulic lines running along the edges or the surface of the enclosure; these conduits, tubes, or hydraulic lines can then be used to defined the edges and thickness of the enclosure. The conduits, tubes, or hydraulic lines could run along inside or outside the enclosure walls. When inside the enclosure walls the conduits, tubes, or hydraulic lines should have minimal diffractive and refractive effect on the ambient sound. Conversely, when outside the enclosure, the conduits, tubes, or hydraulic lines should have noticeable diffractive and refractive effects on the ambient sound. And, when located inside or outside an enclosure with fixed walls the hydraulic force generating means could be used to operate a retracting node.

The pneumatic force generating means may be comprised of a plurality of conduits, tubes, or pneumatic lines for the pneumatic gas. The pneumatic force can then be applied by placing the pneumatic gas under pressure. The pneumatic force generating means may be used to create a distending or contracting force on the enclosure walls by means of internal or external lines, or by external pneumatic jacks, or by miniature internal pneumatic jacks, or pneumatic actuators, or pneumatic lines, or pneumatic plates. so that the flexible enclosure walls could be moved apart, thereby creating said vacuum. A pneumatic force generating means is usually used with an enclosure having flexible walls and/or compression nodes in combination with flexible plastic, rubber, or aluminum sheeting to comprise the surface or walls of the enclosure, although any other flexible sheeting capable of being formed to comprise a hermetic enclosure may be used as well. Varying the distending or contracting force should vary the degree of distension. The pneumatic force generating means may simply comprise conduits, tubes, or pneumatic lines running along the edges or surface of the enclosure; these conduits, tubes, or pneumatic lines can then be used to defined the edges and thickness of the enclosure. The conduits, tubes, or pneumatic lines could run along inside or outside the enclosure walls. When inside the enclosure walls the conduits, tubes, or pneumatic lines should have minimal diffractive and refractive effect on the ambient sound. Conversely, when outside the enclosure, the conduits, tubes, or pneumatic lines should have noticeable diffractive and refractive effects on the ambient sound. Therefore, the pneumatic force generating means as well as the hydraulic means may be used to define surface features or a supplementary surface layer on the enclosure, said surface features comprised of a secondary enclosure for defining surface convolutions that may be applied to the primary enclosure for diffractive, refractive, absorptive and reflective effects, in more complex embodiments. And, when located inside or outside an enclosure with fixed walls the pneumatic force generating means could be used to operate a retracting node.

The line force generating means would normally be used externally to an enclosure having flexible walls. The lines are attached to line nodes which may be glued and or laminated to the surface of the enclosure. This would be done in a fashion similar to what has previously been shown in the camping or sailing arts. To create the vacuum within the enclosure the lines are pulled using a motor or an actuator, or manually, thus expanding the flexible walls of the enclosure. A line force generating means is usually used outside an enclosure having flexible walls and tension and/or compression nodes in combination with flexible plastic, rubber, or aluminum sheeting to comprise the surface or walls of the enclosure, although any other flexible sheeting capable of being formed to comprise a hermetic enclosure may be used as well, The line force generating means would normally be used (although this may not be necessary in all embodiments) to generate a vertex for a flexible enclosure, thus lending stability to a complicated construction. And it may also be used to simply position the enclosure in the physical space under consideration.

The spring force generating means would normally be used internally with an enclosure having fixed walls. It would be used in a node to maintain the tension of support for a nodal plate, or to retract a nodal plate when the opposing force generating means is reduced in power or turned off (The opposing force generating means may be defined here as a force generating means that exerts a force opposite to, and lying in a range varying from a greater or lesser force than, the force exerted by the spring force generating means. However, the spring force generating means can also be used to support the fixed walls of an enclosure so that the hermetic properties of the enclosure are retained and to maintain a nodal means, where the nodal means is comprised of a plurality of nodes having springs. The nodes are distributed within or without an enclosure and attached between or without the enclosure walls thereby maintaining said vacuum within the enclosure. A spring force generating means is usually used in a fixed enclosure having retracting nodes in combination with stiff plastic, aluminum, or glass sheeting to comprise the surface or walls of the enclosure, although any other stiff sheeting capable of being formed to comprise a hermetic enclosure may be used as well, More generally it would be used in conjunction with a repulsive force generating means, a hydraulic force generating means, and a pneumatic force generating means, to retract a nodal plate when these force generating means are turned off.

A leverforce generating means is generally used externally with an enclosure having flexible walls. Usually the lever would be attached to ribs forming part of or embedded in the enclosure, or nodes which are glued or laminated to, or on, the enclosure surface. The lever can then be moved to pull on the ribs or nodes, thereby expanding the enclosure and creating said vacuum within the enclosure. A lever force generating means is usually used outside a flexible expanding enclosure having tension and/or compression nodes in combination with flexible plastic, rubber, or aluminum sheeting that comprises the surface or walls of the enclosure, although any other flexible sheeting capable of being formed to comprise a hermetic enclosure may be used as well.

A strut force generating means may also be used, especially with fixed enclosures. But it would generally have acoustic properties. Usually it would be comprised of a first section having a high absorption coefficient for sound and a second section that is highly reflective of sound by virtue of having an acoustic impedance greater than about ten times the acoustic impedance of the first section. Additionally the first and second sections may be combined to join at an angle of about 90 to 30 degrees, or preferably 75 to 45 degrees, or most preferably at about 60 degrees from the enclosure surface. This should maximize the amount of reflection at the first and second section boundary.

Additionally, for fixed enclosures using sectioned struts, the frame of the enclosure should be layered as well with the same materials and angle of joining as was used for the struts. This prevents sound from being transmitted around the frame. A strut force generating means is usually used in a fixed enclosure in combination with stiff plastic, aluminum, or glass sheeting to comprise the surface or walls of the enclosure, although any other stiff sheeting capable of being formed to comprise a hermetic enclosure may be used as well. In addition a fixed enclosure having a strut force generating means may also have an enclosure transduction circuit as described above.

Therefore, according to another of its aspects the invention should comprise a force generating means selected from the group consisting of a electric force generating means, a hydraulic force generating means, a pneumatic force generating means, a line force generating means, a spring force generating means, a lever force generating means, a strut force generating means, and;

wherein the electric force generating means is creates a distending or contracting force between a first wall and a second wall, said electric force generating means selected from the group consisting of charged plates, an electromagnetic node, a solenoid, an electric actuator, and an electric motor, so that varying the electric power applied to said charged plates, electromagnetic node, solenoid, electric actuator, and electric motor, causes the distending or contracting force to vary the degree of distension or contraction between a first wall and a second wall, whereby the volume of said space containing said variable density fluid between said first wall and said second wall may be varied, and;

wherein the hydraulic force generating means creates a distending or contracting force between a first wall and a second wall, said hydraulic force generating means selected from the group consisting of a hydraulic conduit, a hydraulic tube, a hydraulic pipe, a hydraulic actuator, and a hydraulic jack, so that varying the hydraulic pressure applied to said hydraulic conduit, hydraulic tube, hydraulic pipe, hydraulic actuator, and hydraulic jack, causes the distending or contracting force to vary the degree of distension or contraction between said first wall and said second wall, whereby the volume of said space containing said variable density fluid between said first wall and said second wall may be varied, and;

wherein the pneumatic force generating means creates a distending or contracting force between a first wall and a second wall, said pneumatic force generating means selected from the group consisting of a pneumatic conduit, a pneumatic tube, a pneumatic pipe, a pneumatic actuator, and a pneumatic jack, so that varying the pneumatic pressure applied to said pneumatic conduit, pneumatic tube, pneumatic pipe, pneumatic actuator, and pneumatic jack, causes the distending or contracting force to vary the degree of distension or contraction between said first wall and said second wall, whereby the volume of said space containing said variable density fluid between said first wall and said second wall may be varied, and;

wherein the line force generating means creates a distending or contracting force between a first wall and a second wall, said line force generating means comprising a plurality of lines, said plurality of lines connected to attachment plates on said first wall and said second wall, or on said frame, so that varying the pulling force exerted by said plurality of lines causes the distending or contracting force to vary the degree of distension or contraction between said first wall and said second wall, whereby the volume of said space containing said variable density fluid between said first wall and said second wall may be varied, and;

wherein the spring force generating means creates a distending or contracting force between a first wall and a second wall, said spring force generating means comprising a plurality of springs, so that said plurality of springs can absorb said distending or contracting force to vary the degree of distension or contraction between said first wall and said second wall, so that varying the restoring force exerted by said plurality of springs causes the distending or contracting force to reduce the degree of distension or contraction between said first wall and said second wall, whereby the volume of said space containing said variable density fluid between said first wall and said second wall may be maintained, and;

wherein the lever force generating means creates a distending or contracting force between a first wall and a second wall, said lever force generating means comprising a plurality of levers,
so that said lever force generating means causes said plurality of levers to vary the degree of distension or contraction between said first wall and said second wall,
so that varying the force exerted by said levers force generating means causes the distending force to vary the degree of distension or contraction between said first wall and said second wall,
whereby the volume of said space containing said variable density fluid between said first wall and said second wall may be varied.

An electric force generating means may be used with fixed walls and flexible walls. With fixed walls it is usually resident in a node and may be used to retract or advance a supporting strut. With flexible walls it may be located in nodes to cause the enclosure walls to separate thereby creating said vacuum.

A node may be said to be a restricted loci on the enclosure, having any combination of three properties; a structural element, a variable element, and a sensing element. In practice, a force generating means may preferably be applied at a node of the enclosure. Supporting struts are really representative of the most primitive form of force generating means; that is to say support of a purely static nature. For better results it is preferable that a dynamic force generating means be used. For enclosures having fixed walls it may therefore be preferable that they also have retracting nodes. A retracting node is usually comprised of a force generating means dynamically functioning as a retractable supporting strut. Usually a distal end of the force generating means comprises a nodal pad that normally rests evenly against a nodal plate attached to the enclosure wall, but that is pulled away from the enclosure under retraction.

Clearly, for an enclosure having fixed walls, if the walls were supported entirely by retracting nodes and all nodes retracted simultaneously, structural failure might result. Therefore the enclosure may be constructed to comprise more retracting nodes than would be necessary to maintain structural stability, The excess retracting nodes may then be retracted without causing structural failure. The advantage conferred by this embodiment is that the sound transmission may be increased or decreased across different areas of the enclosure thereby allowing the sound baffling characteristics of the enclosure to be modulated.

Some simple arrangement which may comprise a retracting node are retracting springs (a spring force generating means) which would retract the nodal pads, but are prevented from doing so because a pneumatic force generating means, or a hydraulic force generating means, or an electric force generating means, or any other force generating means maintain the retracting node in the extended position. In practice it would usually be preferable to use a pneumatic force generating means, because usually a line from the pressure varying means will be attached to the enclosure and will be able to provide the requisite air supply and pressure to the pneumatic force generating means. It should be noted that when a large number of nodes as discussed here are being used, they effectively function as a nodal means.

It may also be advantageous to add a nodal means for use with an electric force generating means to the enclosure. This involves the creation of nodes at useful locations within the enclosure, along the surface of the enclosure or around the perimeter of the enclosure. Alternatively, one could say that nodes may be located in the interior of the enclosure usually in tandem with, or in lieu of, a structural support, along faces of the enclosure, along edges of the enclosure, and along vertices of the enclosure. In one sense, then, a node is merely a location within or on the structure of the enclosure, although it usually also functions as a location for a structural element, or a variable element, or a sensing element. And the walls of the enclosure may be reinforced to allow the placement of these elements. Alternatively the nodes may be loci for attaching force generating means to the enclosure.

In general a force generating means should be applied at a node although this may not always be the case, The node should generally be given the name of the force generating means, a strut force generating means being applied at a strut node, a hydraulic force generating means being applied at a hydraulic node etc.

The question remains whether the node is internal or external, Internal nodes reside inside the enclosure while external nodes may be attached to a crib surrounding the enclosure or they may be directly attached to a wall or a structural component (e.g. a pillar) of the physical space under consideration, or just to the enclosure surface.

Lastly, the nodes may be of two general types, retracting nodes and tension and/or compression nodes. The retracting nodes are used with fixed walls that are substantially able to withstand the internal or external pressure on their own. For an enclosure containing retracting nodes a substantial number of the nodes will not be necessary to maintain structural integrity at any one time. Consequently, by changing the configuration of the nodes that are in the retracting vs. supporting states the transmission of sound or heat can be preferably shifted from one part of the enclosure to another.

It may therefore be preferable that according to another one of its aspects the invention comprises; an enclosure further comprising a node, said node limited to a loci on said enclosure, said node further comprising at least one of a structural element, a variable element, and a sensing element.

The nodes may roughly be divided into retracting and tension and/or compression nodes and may often be evenly distributed within the enclosure or across the enclosure surface. And, since the nodes generally are loci for variable elements, it is possible to use the controlling means to control or activate them independently or as subsets of the total number of nodes in the enclosure. This could allow the transmission of sound and/or thermal energy to be varied across a surface of the enclosure. Those areas of the surface where the node permitted the transmission of sound and/or thermal energy would be transmitting sound and/or thermal energy, whereas areas where the node did not allow the transmission of sound and/or thermal energy would be barred from transmitting sound and/or thermal energy.

It may be preferable to control a nodal means through the output from a PROM nodal chip or a standard chip that is capable of serving as a nodal chip and handling the specific electronic problem to suit.

The nodal chip essentially controls the activation of the nodes to preferred state and will have one output for each of the nodes in the enclosure. Therefore the nodal chip can switch any permutation of nodes into the preferred state (e.g. retracted or extended), thereby allowing the corresponding nodes to be controlled.

On the input side the nodal chip will have the ability to receive a signal from the controlling means and to convert that signal into a digital representation presented on the nodal chip output leads, as comprising either triggering voltages for the active elements or comprising neutral voltages that are insufficient to trigger the active elements (e.g. switch on an electric motor). Therefore, the output leads will be configured as preferable for a particular application. For an electric motor, on lead would signal the on/off condition. But other leads might indicate how far to turn (for a stepper motor). Therefore a single chip may not always suffice and an electronic nodal circuit may have to be constructed so that the appropriate number of output leads is made available to control the nodes, as required.

Tension and/or compression nodes are used in combination with flexible walls. Flexible walls will be put under compression if the external pressure is great than the internal pressure. Flexible walls will be put under distension if the internal pressure is greater than the external pressure. When a flexile wall of an enclosure is in a state of compression the internal tension and/or compression nodes will be in a state of compression while the external tension and/or compression nodes will be in a state of tension. When a flexible wall enclosure is in a state of tension, the internal tension and/or compression nodes will be in a state of tension and the external tension and/or compression nodes will be in a state of compression.

The tension and/or compression nodes may therefore be able to adjust to the internal pressure of an enclosure having flexible walls. In, combination with a pressure varying means they need to change the amount and direction of the force applied by the force generation means as may be required to compensate for any change in the internal pressure of the flexible enclosure.

It may therefore be preferable that according to one of its aspects the invention further comprises; an enclosure further comprising a nodal means having a plurality of retracting node variable elements or a plurality of tension and/or compression node variable elements, said nodal means further comprising a controlling means, so that said controlling means selectively enables the transmission of sound or heat through a subset of said plurality of retracting node variable elements or said plurality of tension and/or compression node variable elements, whereby the transmission of sound or heat may be varied over a region of said enclosure.

And it may further be preferable that according to one of its aspects the invention embodies a nodal means in combination with a controlling means, so that said controlling means controls the nodes of said nodal means, and the geometrical properties of said enclosure, or the acoustic properties of said enclosure, or the thermal properties of said enclosure are optimized.

And it may further be preferable that according to one of its aspects the invention further comprises an enclosure having fixed walls in combination with a plurality of retracting nodes or an enclosure having flexible walls in combination with a plurality of tension and/or compression nodes.

In conjunction with the enclosure having a force generating means and a nodal means it may also be preferable to have a pressure varying means. The pressure varying means contains a means for admitting and removing, and, in addition also has a compressor for increasing the pressures above atmospheric. This means that the pressure varying means can increase the pressures above the ambient pressure and decrease the pressures below ambient pressure. This may be useful in certain acoustic applications. There are certain refractive effects that become more pronounced when the enclosures are at a greater pressure. For example, an acoustic lens may use a higher pressure than atmospheric to obtain a refractive focus for sound.

It may therefore be preferable that according to another of its aspects the invention further comprises; a pressure varying means (756) connected to said enclosure, so that by admitting and removing matter to and from said enclosure the sound and thermal baffling characteristics of said enclosure are varied by said pressure varying means. But the pressure varying means also contains additional elements and functions beyond those shown by the means for admitting and removing.

The means for admitting and removing is contained within the pressure varying means (756) and should have a sealed piping network (335, 336, 338, 340, 342) to enable the admitting and removing of matter to and from the enclosures. The piping network may have a separate valve (294, 296) for each pipe leading from the means for admitting and removing to each enclosure. The means for admitting and removing should also have controlling lines (344, 346, 348, 350, 352) for setting the valves as well as a vacuum pump connected to the pipes by means of the valves. Upon receiving the appropriate instructions the valve leading to an enclosure where matter is to be admitted and removed is opened or closed to a degree determined by the instructions. Then matter is removed through the action of the vacuum pump if required. Or matter may be admitted by means of the external pressure, if that is what is required. The external pressure may force air into the enclosures directly through an intake valve contained in the means for admitting and removing. This intake valve may also function as an exhaust valve for the vacuum pump. The means for admitting and removing may therefore also contain an apparatus for enabling either the vacuum pump or the external pressure to act on the piping network by means of this intake or exhaust valve. Alternatively, the matter may be retained within the means for admitting and removing. This implies that a storage chamber for storing matter is contained within the means for admitting and removing. The storage chamber (758) is capable of storing all the matter that is present within the enclosures, the piping network, the vacuum chamber, and the vacuum pump. Matter may therefore be removed from the enclosures and stored in the storage chamber, which may be a vacuum capacitor, by the means for admitting and removing. Or some of the same matter may be admitted to the enclosures by the means for admitting and removing. The implementation of either admitting or removing is carried out on the basis of information received from the means for measuring.

The pressure varying means also has a piping network (770, 772, 774, 776, 778) to enable the pressurizing or decompression and evacuation of the enclosures. And the piping network may also have at least one separate valve (751, 782, 784, 786), associated with each pipe and/or enclosure (788, 790, 792). Also the pressure varying means will have controlling lines for setting the valves as well as a compressor for increasing the pressure above atmospheric.

The pressure varying means may also have matter density reservoirs (750), which may have the same physical construction as a vacuum capacitor, and that contain homogeneous fluid matter of varying density for admittance to the enclosure as may be preferable. The densities will be different from the density of the atmosphere and function to change the refractive index of sound at the enclosure wall and the homogeneous fluid matter boundary. This should have novel results with regards to the focusing of sound, or the refraction and reflection of sound in general.

It may therefore be preferable that according to one of its aspects the invention further comprises; a pressure varying means having a plurality of matter density reservoirs, said matter density reservoirs comprising homogeneous fluid matter having different densities, so that the density of matter within said enclosure may be varied from the density of the atmosphere by said pressure varying means.

When a matter density reservoir is used in operation, the homogeneous fluid matter may be kept separate from the atmosphere to substantially preserve its purity. This is accomplished by reserving a conduit path through the piping network for the use of the homogeneous fluid matter. Alternatively the homogeneous fluid matter may be mixed with the atmosphere to achieve a preferred mixture having a different density. This mixture is then stored in a mixing chamber, which may be part of a vacuum capacitor. Or two or more homogeneous fluid matters may be mixed together to comprise a preferred mixture having a different density within a mixing chamber. The preferred mixture having a different density may then be admitted to the enclosure from the mixing chamber. Obviously, fluids known to be hazardous to human health must not be used in an environment where humans are active.

Therefore according to another of its aspects the invention further comprises; a mixing chamber (752), for mixing said homogeneous fluid matter having different densities, so that the density of matter within said enclosure may be varied by said pressure varying means.

If the measured values and characteristics of the ambient sound do not have a sufficiently close correspondence to the input parametric values and characteristics of the ambient sound then matter is either admitted or removed to increase this correspondence. Then, after the admitting or removing of matter has been carried out by the means for admitting and removing, new measurements of the values and characteristics of the ambient sound in the physical space controlled by said sound baffling device are taken. These new measured values and characteristics of the ambient sound are then correlated by the means for correlating to the stored parametric values and characteristics of the ambient sound and, if the new correspondence lies within a parametrically set degree of accuracy, the procedure of adjusting the sound baffling characteristics of the sound baffling device is halted.

Alternatively, if the new measured values and characteristics of the ambient sound do not have a sufficiently close correspondence to the stored parametric values and characteristics of the ambient sound, the procedure is repeated. The controlling means therefore has a feedback mechanism implemented by the means for correlating which carries out adjustments based on the measured values and characteristics of the ambient sound until the stored parametric values and characteristics of the ambient sound and the measured values and characteristics of the ambient sound agree within an input parametric level of accuracy set by the input means. When such agreement is reached the means for correlating enters a sampling loop that checks periodically to ensure that the agreement of the measured values and characteristics with the stored parametric values and characteristics of the ambient sound continues. Should the agreement be lost the adjustment of the sound baffling characteristics of the sound baffling device should resume.

The controlling program may carry out the actual correlation and determination of values. Basically three sets of variables may be used as well as one set of constants or operating principles. The first set of variables is just the set of input parametric values and characteristics (302) of the ambient sound input by the operator or user of the sound-baffling device. The second set of variables, which may also be input by the user, simply lists the input tolerances (303) required for each of the values and characteristics of the ambient sound before the convergence procedure carried out by the controlling means may be terminated. The last set of variables lists the actual new measured values and characteristics (312) of the ambient sound as of the last reading of the sensors.

The means for correlating will have default settings for the first and second set of variables, namely the default parametric values and characteristics and the default tolerances (754,756). This may ensure that, if the controlling means is engaged and no input parametric values and characteristics of the ambient sound or input tolerances are entered through the input means, the sound baffling device will still function in a useful way. When a controlling program is used, the set of constants and operating principles contained within the controlling program should act on the data received by the sensors with reference to the default parametric values and characteristics of the means for correlating, or the input parametric values and characteristics of the input means.

These constants and operating principles are essentially drawn from the science and technology of acoustics and the science and technology of thermal control. The spatial configuration of the sound-baffling device is evaluated scientifically and the relevant data is entered into the controlling program as a list of constants. Specifically the data comprises a description of the physical space to be controlled, the number of enclosures used, and the shape, disposition and size of the enclosures as well as the formulation of interaction among these entities.

The operating principles are drawn from the science and technology of acoustics and the science and technology of thermal control, and are stored in the controlling program. They are comprised of the equations of acoustics and thermal science as well as algorithms using these equations to calculate and predict an acoustic or thermal result. In the application of these equations and algorithms, the constants drawn from the specific case data are substituted by the controlling program for the appropriate variables in the equations and algorithms. The equations and algorithms may then be used to create predicted parametric values and characteristics of the ambient sound in the controlled physical space under consideration for a given state of the sound-baffling device.

The controlling program then compares the predicted parametric values and characteristics of the ambient sound with the input parametric values and characteristics of the ambient sound read into the program from the input means. By means of the equations and algorithms the controlling program then estimates the change in the state of the sound-baffling device required to create the parametric values and characteristics of the ambient sound within the physical space under consideration governed by the sound-baffling device. Having estimated the necessary change, the controlling program then sends a requisite list of instructions through the means for correlating to the means for admitting and removing which, by admitting or removing matter in the required amounts to and from the various enclosures changes the state of the sound baffling device.

The controlling program then checks the measured values and characteristics of the ambient sound to see if they now lie within the allowed stored parametric tolerance. If the measured values and characteristics of the ambient sound lie within the stored parametric tolerance, the controlling program next enters a sampling loop. In the loop it samples the measured values and characteristics of the ambient sound and the input parametric values and characteristics of the ambient sound at a preset parametric rate. If a difference in the measured values and characteristics of the ambient sound falling outside the stored parametric tolerance is found by sampling, then a new set of instructions is sent to the means for admitting and removing and/or the pressure varying means, so that this difference may be reduced to fall within the stored parametric tolerance. In this fashion the controlling means converges automatically to establish an optimum correlation to the preferred set of parametric values and characteristics of the ambient sound in the physical space governed by the sound-baffling device. But the optimum correlation may not be a total correlation. If after a preset number of trials, one or more of the preferred set of parametric values and characteristics still falls outside the stored parametric tolerance, the convergence procedure may, at least temporarily, be aborted with respect to the offending stored parametric values and characteristics. This may be done by simply removing the parametric values and characteristics in question for a determined number of iterations from the total list of values and characteristics, which must be considered by the controlling means.

For embodiments that function without the optional controlling program and microprocessor, some tasks normally handled by these elements may be assumed by the operator. And the controlling means may also have additional on board hardware for dealing with some of these tasks. This may involve the use of additional circuitry and/or the use of programmable logic devices.

To speed up the removal of matter from the enclosures, it may be found useful to maintain an appropriately sized vacuum chamber in an evacuated state. As shown in a still further part of FIG. 13, the vacuum chamber is also connected to the enclosures through the valves and the piping network. When the valves between the enclosures and the vacuum chamber are opened, the matter rushes from the enclosures into the vacuum chamber, thereby causing the enclosures to be evacuated at a high speed. This allows the matter within the enclosures to be adjusted more rapidly. It may therefore be preferable that the invention further comprises a large vacuum chamber (316) connected by chamber valves (318, 320) to said sound baffling device, said vacuum chamber maintained in a state of vacuum by means of a removal valve (322) and pipe (335) connecting said vacuum chamber to said means for admitting and removing, so that when said controlling means causes said chamber valves to open, pressurized matter present within said enclosures flows rapidly into said vacuum chamber, so that the speed with which the matter within said enclosures is removed is optimized.

However, for those embodiments of the invention where the enclosures do not permit the admitting and removing of matter, the creation of the vacuum inside the enclosures may be most easily done in a vacuum chamber. This process of manufacture may be carried out by means of robotics. Or it could be performed by appropriately equipped men. Accordingly, it is preferable that the step in the process of manufacture which creates said enclosure is carried out within a vacuum chamber, so that the vacuum within said vacuum chamber is incorporated into said enclosure.

A more concise and specific aspect of the operation of the preferred embodiment is shown in the program logic depicted by the flowchart of FIG. 39. The flowchart begins with START (700), which is merely representative of switching the device on. Start also assumes that only a means for correlating is being used so that there is just one calculating means; therefore N the count of calculating means is set to one, N=1. Next (702), the logic checks to see if input parametric values and characteristics have been entered into the input means; if yes (704) the stored values and characteristics are set equal to the input parametric values and characteristics, if no (706) the stored parametric values and characteristics are set equal to the default parameters and characteristics. Next (708) the logic checks to see if input tolerances have been entered. If yes (710)) the stored tolerances are set equal to the input tolerances and, if no (712)) the stored tolerances are set equal to the default tolerances.

Next (714) the measured values and characteristics are taken in measurement from the physical space under consideration. And after checking to see that N=1 the logic determines a benchmark (716) by comparing the measured values and characteristics to the stored parametric values and characteristics. The benchmark in a general sense comprises the difference between the stored values and characteristics and the measured values and characteristics. The benchmark would also comprise a value indication of the amount of adjustment which the pressure varying means should make in combination with the force generating means as well as adjustments to variable elements etc.; so that the benchmark may comprise an adjustment value indication for the force generating means and the pressure varying means, including and adjustment value indication for the means for correlating which would handle the adjustment of variable elements. The logic next (718) checks to see if the benchmark falls within the range of values given by the stored tolerances. If yes (720) the logic waits for an interval predetermined by the requisite stored parametric tolerance and then gets a new measurement (714) of the measured values and characteristics from the physical space under consideration, re-calculates the benchmark (716) and checks (718) to see if the benchmark still falls within the range of values given by the stored tolerances.

When the benchmark falls outside the range of values given by the stored parametric tolerances the logic checks (722) to see if the controlling means also comprises a microprocessor. If yes (724), a second benchmark is calculated by the microprocessor using comparison. The logic next (726) checks to see if the second benchmark falls within the range of values given by the stored parametric tolerances. If yes (728), N is set equal to 2, and the logic waits for the requisite interval and then gets a new measurement (714) of the measured values and characteristics from the physical space under consideration, and, if N=2, is sent immediately to re-calculate the second benchmark (724) and check (726) to see if the second benchmark still falls within the range of values given by the stored parametric tolerances. If yes, after waiting for the requisite interval the cycle is repeated; if no (730), the logic checks to see if the controlling means also comprises a neural net. If yes (732), a third benchmark is calculated by the neural net using comparison. The logic next (734) checks to see if the third benchmark falls within the range of values given by the stored tolerances. If yes (736), N is set equal to 3, and the logic waits for the requisite interval and then gets a new measurement (714) of the measured values and characteristics from the physical space under consideration, and if N=3, is sent immediately to re-calculate the third benchmark (732), and check (734) to see if the third benchmark still falls within the range of values given by the stored parametric tolerances. If yes, the cycle is repeated; if no (734), the force generating means and/or the pressure varying means (726) is adjusted to change the state of the physical space under consideration.

If new information is input into the input means during the operation of this program, the program will be halted, and then resume at START as soon as the input operation is completed, Also an error condition might arise and cause N to have a value other than one, two, or three. This would also cause the program to halt. It should be noted that this is merely one way in which the calculating means or nodes could be organized, Alternatively they could be organized to operate concurrently.

An enclosure having flexible walls may also comprise a force generating means in combination with a pressure varying means. The pressure varying means is used to pressurize and depressurize the enclosure and the force generating means is used to balance this expansion or contraction. Or the pressure varying means is used to remove matter from the enclosure thereby causing the enclosure to contract and a force generating means is used to anchor the exterior of the enclosure to prevent collapse at preferred loci on the enclosure surface.

It may therefore be preferable that according to one of its aspects the invention further comprises;
an enclosure, wherein said enclosure has a surface comprised of a flexible wall, and;
the shape of said surface is determined by said pressure varying means operating in combination with said force generating means.

A preferred shape for the surface of the enclosure would be a circular shape having a substantially convex or concave side. An enclosure shaped in this fashion should function as an acoustic lens. If both sides of the enclosure were convex and the speed of sound inside the lens were greater than the speed of sound outside the lens then the direct sound wave would diverge from the acoustic lens after passing through the acoustic lens. If both sides of the enclosure were concave then the direct sound wave would be focused, and converge to a focal point. Alternatively, if the speed of sound inside the lens were less than the speed of sound outside the lens then for said convex and concave acoustic lens constructions the direct sound wave would be focused and diverging from the acoustic lens, respectively.

Therefore according to another of its aspects the invention further comprises; an enclosure having a surface comprising an annular shape having a substantially convex or concave side, so that said enclosure functions as an acoustic lens.

Carrying this notion one step further, one can create an enclosure covered with a plurality of surface enclosures, whose shape and size roughly corresponds to the surface features of the enclosure (e.g. For a cube you would have six surface enclosures). The transmission of energy through each of the surface enclosure may then be controlled by the pressure varying means operating in combination with a force generating means, so that a predetermined amount of energy may be transmitted through said enclosure.

Therefore according to another of its aspects the invention has an enclosure further comprising a plurality of surface enclosures, said surface enclosures comprising a substantially contiguous covering of the surface of said enclosure, said surface enclosures further comprising said pressure varying means and said force generating means, so that the transmission of sound through said surface enclosures may be varied by said pressure varying means operating in combination with said force generating means, so that said enclosure is effective to achieve a predetermined distribution of sound.

And it may be preferable to place a sound generating means inside the enclosure. The surface enclosures then control the transmission of sound out of the enclosure. If all the surface enclosures are made non-transmitting for sound, then the transmission of sound from the sound generating means within the enclosure should substantially be stopped. Alternatively, is some of the surface enclosure are capable of the transmission of sound then the transmission of sound will take place through those surface enclosure thereby enabling the selective directional transmission of sound.

It may therefore be preferable that according to one of its aspects the invention further comprises;
an enclosure containing a sound generating means, said sound generating means contained within said surface of said surface enclosure, and;
wherein said plurality of surface enclosure enable directional control over the transmission of sound from said sound generating means,
so that said sound generating means is effective to operate as a directional sound source.

Or, it may be preferable that according to one of its aspects the invention further comprises; an enclosure further comprising a sound generating means, said sound generating means contained within said enclosure, and;
Said enclosure further having a plurality of surface enclosures, so that said plurality of surface enclosures enable directional control over the transmission of sound from said sound generating means,
whereby said enclosure is effective to operate as a directional and variable sound source.

EXAMPLES

Example 1 (Pneumatic Force Generating Means—Flexible Wall)

Using a mold for preparing a rubber or plastic product, hermetically form an annular pneumatic tube made of rubber or plastic or other moldable hermetic material, said annular pneumatic tube molded in one piece with a rear wall and; said annular pneumatic tube further having a central groove and a first set of mutually parallel pneumatic cross-linking tubes attached to the annular pneumatic tube between the rear wall and the central groove and further having a second set of mutually parallel pneumatic cross-linking tubes attached to the annular pneumatic tube between the front wall and the central groove and running perpendicularly to said first set of parallel pneumatic cross-linking tubes.

The annular pneumatic tube may be made of rubber or plastic or any other moldable hermetic material, and may also have openings for accepting the placement of an external and internal valve located in the outside layer and the inside layer of the annular pneumatic tube, respectively. This is only necessary when the connection of a pressure varying means to the tube is contemplated and embodiments that do not use a pressure varying means would not need these openings.

After releasing the annular pneumatic tube from the mold and testing the hermetic properties of the tube, attach an internal frame by fitting the internal frame into the central groove. The internal frame will have tube frame holders for attaching to the central groove and nodal plates for attaching to the sets of parallel pneumatic cross-linking tubes. Next add attachment plates to the outside wall of the annular pneumatic tube, if required. The internal frame and the attachment plates may be made of metal or any other material capable of being attached to the annular pneumatic tube so that the handling of forces upwards of one hundred pounds is enabled.

Next attach a hermetic pipe valve to the outside layer and optionally attach a hermetic pipe insert valve to the inside layer of the annular pneumatic tube so that these valves are suitable for connection to a pressure varying means and a means for admitting and removing. The hermetic pipe valve is connected to the pressure varying means and in particular to the high-pressure output, which is used to increase the pressure in the annular pneumatic, tube to above atmospheric. The hermetic pipe insert valve may be connected by the pipe insert to the pressure varying means to enable both the increasing of the pressure in the enclosure to above atmospheric or the reduction of the pressure in the enclosure to below atmospheric.

The pipe insert is a smaller pipe optionally contained in the pipe and may be connected to the hermetic pipe insert valve in the annular pneumatic tube so that a pressure varying means may act on the interior of the enclosure.

Next, increase the pressure in the pneumatic tube so that the tube achieves substantially its maximum rated expansion and acts like the open frame of an enclosure having the shape of a hollow sheet. Apply and hermetically seal a front wall to the open side of the annular pneumatic tube.

A pressure sensor may also be added to the interior of the enclosure prior to adding the front wall. The sensor could be operated by a wire running through the pipe insert or the pipe and into the enclosure. But it may be preferable to have the sensor operate by using RF technology to transmit and receive the requisite information as necessary.

The operation of this embodiment is governed by the pneumatic force generating means. Starting with atmospheric pressure in the enclosure; when the enclosure is blown up to expand to ten times its size the atmospheric pressure inside the enclosure will be one tenth atmospheric, assuming the hermetic properties are not compromised. The basic operating principle is that over pressure at the surface of the enclosure can be balanced by increasing the pressure in the pneumatic tubes.

(Of course the pneumatic tube need not be made in one piece. In fact the pneumatic tube having a central groove and the parallel pneumatic cross-linking tubes can be made separately and then put together. Both the rear wall and the front wall can be produced separately and then attached to the annular pneumatic tube having a central groove.)

The attachment plates will have eyes or other attaching means for, most usually attaching to a line force generating means. The line force generating means will then be able to position the enclosure in the physical space or it may exert forces to effect changes in the shape of the enclosure. These forces should be kept sufficiently small so that the hermetic properties of the enclosure are not compromised.

Example 1A (Example 1 with a Spring Force Generating Means Added)

Create an enclosure as defined in example 1, but add a spring force generating means as follows. Firstly, along the inside of the rear and front wall create nodal plates occupying geometrically regular positions in the open portions of the grid created by the first and second set of pneumatic cross-linking tubes. Next, before adding the front wall, attach the rear part of the springs to the nodal plates located in the rear wall. Lastly, when attaching the front wall attach the front part of the springs to the nodal plates in the front wall prior to hermetically attaching the front wall to the annular pneumatic tube.

The springs are tensioned to exert substantially no force on the enclosure when the interior is at less than atmospheric. But when the pressure varying means is used to increase the pressure in the enclosure above atmospheric the springs exert a contracting force on the enclosure walls, thereby preventing excessive expansion of the enclosure.

It may also be preferable that the spring is contained in two cylindrical halves. One half cylinder will fit inside the other and the ends of both half cylinders are closed off. The spring is connected to the end plates in the ends of both half cylinders. And when assembled the spring should create a slight tension holding the halves together.

Should the enclosure wall move apart during operation the tension will become more pronounced and the spring nodal means will exert a contracting force to bring the enclosure walls closer together.

Example 2 (Hydraulic Force Generating Means—Flexible Wall)

Using a mold for preparing a rubber or plastic product, hermetically form an annular hydraulic tube made of rubber or plastic or other moldable hermetic material, said annular hydraulic tube molded in one piece with a rear wall and; said annular hydraulic tube further having a central groove and a first set of mutually parallel hydraulic cross-linking tubes attached to the annular hydraulic tube between the rear wall and the central groove and further having a second set of mutually parallel hydraulic cross-linking tubes attached to the annular hydraulic tube between the front wall and the central groove and running perpendicularly to said first set of parallel hydraulic cross-linking tubes.

The annular hydraulic tube may be made of rubber or plastic or other moldable hermetic material, and may also have openings for accepting the placement of an external and internal valve located in the outside layer and the inside layer of the annular hydraulic tube, respectively. This is only necessary when the connection of a pressure varying means to the tube is contemplated and embodiments that do not use a pressure varying means would not have these openings.

After releasing the annular hydraulic tube from the mold and testing the hermetic properties of the tube, attach an internal frame by fitting the internal frame into the central groove. The internal frame will have tube frame holders for attaching to the central groove and nodal plates for attaching to the sets of parallel hydraulic cross-linking tubes. Next add attachment plates to the outside wall of the annular hydraulic tube, if required. The internal frame and the attachment plates may be made of metal or any other material capable of being attached to the annular hydraulic tube so that the handling of forces upwards of one hundred pounds is enabled.

Next attach a hydraulic pipe valve to the outside layer and connect it to a hydraulic reservoir. And attach a hermetic pipe insert valve to the inside layer of the annular hydraulic tube so that this valve is suitable for connection to a pressure varying means and a means for admitting and removing. The hydraulic pipe valve is connected to the hydraulic reservoir and when the hydraulic pressure is increased the resulting hydraulic force can counteract the exterior pressure, which increases as the degree of evacuation in the enclosure rises.

The hermetic pipe insert valve may be connected by the pipe insert to the pressure varying means to enable both the increasing of the pressure in the enclosure to above atmospheric or the reduction of the pressure in the enclosure to below atmospheric. The pipe insert is a smaller pipe contained in the pipe and is connected to the hermetic pipe insert valve in the annular hydraulic tube so that a pressure varying means may act on the interior of the enclosure.

Next, increase the pressure in the hydraulic tube so that the tube achieves substantially its maximum rated expansion and acts like the open frame of an enclosure having the shape of a hollow sheet. Apply and hermetically seal a front wall to the open side of the annular hydraulic tube.

A pressure sensor may also be added to the interior of the enclosure prior to adding the front wall. The sensor could be operated by a wire running through the pipe insert or the pipe and into the enclosure. But it may be preferable to have the sensor operate by using RF technology to transmit and receive the requisite information as necessary.

The operation of this embodiment is governed by the hydraulic force generating means. Starting with atmospheric pressure in the enclosure; when the enclosure is increased in size the atmospheric pressure inside the enclosure will be reduced, assuming the hermetic properties are not compromised. The basic operating principle is that over pressure at the surface of the enclosure can be balanced by increasing the pressure in the hydraulic tubes.

(Of course the hydraulic tube need not be made in one piece. In fact the hydraulic tube having a central groove and the parallel hydraulic cross-linking tubes can be made separately and then put together. Both the tear wall and the front wall can be produced separately and then attached to the hydraulic tube having a central groove.)

The attachment plates will have eyes or other attaching means for, most usually attaching to a line force generating means. The line force generating means will then be able to position the enclosure in the physical space or it may exert forces to effect changes in the shape of the enclosure. These forces should be kept sufficiently small so that the hermetic properties of the enclosure are not compromised.

Example 2A (Example 2 Connected to an Electric Force Generating Means—Flexible Wall)

Create an enclosure as defined in example 2, but add an electric force generating means as follows. Firstly, along the inside of the rear and front wall create nodal plates occupying geometrically regular positions in the open portions of the grid created by the first and second set of mutually parallel hydraulic cross-linking tubes. Next, before adding the front wall, attach small solenoids to the nodal plates located in the rear wall. Lastly, when attaching the front wall attach the solenoid plunger to the nodal plates in the front wall prior to hermetically attaching the front wall to the annular hydraulic tube.

The solenoids are tensioned to exert substantially no force on the enclosure when the interior is at less than atmospheric. But when the pressure varying means is used to increase the pressure in the enclosure above atmospheric the solenoids spring into action and exert a contracting force on the enclosure walls, thereby preventing excessive expansion of the enclosure.

It may also be preferable that the solenoid is contained in two cylindrical halves. One half cylinder will fit inside the other and the ends of both half cylinders are closed off. The solenoid is connected to the end plate of the cylinder that is attached to a nodal plate located in the rear wall. The solenoid plunger in the expanded position is connected to the end plate of the cylinder attached to a nodal plate located in the front wall. When a distending force is applied to the enclosure walls (e.g. by the pressure varying means) a pressure switch in the solenoid may activate the solenoid so that the solenoid will exert a contracting force to bring the enclosure walls closer together.

Example 2B (Hydraulic Force Generating Means—Fixed Wall)

Prepare a frame having three to five millimeters thickness. Hermetically attach a back plate or wall to this frame, preferably made from a material having at least one tenth the acoustic impedance of the frame material. The attachment may be made by means of an attachment frame that fits over the back plate and hermetically seals it against the frame. The attachment frame may be made of either the frame material or the back plate material. And the frame and the attachment frame may be made of metal or any other material capable of the handling of forces upwards of one hundred pounds.

The frame should also have openings for accepting the placement of a pneumatic and a hydraulic valve. Add the hydraulic valve to allow the admission of hydraulic fluid from a hydraulic reservoir and add the pneumatic valve to allow the enclosure to be connected to a pressure varying means.

Next attach a hydraulic line to the hydraulic valve and connect it to the hydraulic reservoir. And attach a pneumatic line to the pneumatic valve and establish a connection to a pressure varying means and a means for admitting and removing. The pneumatic line is connected to the pressure varying means to enable the pressure in the enclosure to be varied from atmospheric.

Next, attach a hydraulic tube to the back plate by gluing, so that the tube describes a geometrically uniform pattern over the entire back plate. More than one tube could be used to comprise the geometrically uniform pattern, but it may be convenient to use only one tube. The geometrically uniform pattern could be a repetitive pattern of sinusoidal or serpentine curves, or any other geometrically uniform pattern. And after the hydraulic tube has been attached to the back plate the front plate is fitted over the hydraulic tube and hermetically attached to the frame. The attachment may be made by means of an attachment frame that fits over the front plate and hermetically seals it against the frame. The attachment frame may be made of either the frame material or the front plate material. And the frame and the attachment frame may be made of metal or any other material capable of the handling of forces upwards of one hundred pounds.

A pressure sensor may also be added to the interior of the enclosure prior to adding the front wall. The sensor could be operated by a wire running through the pneumatic line into the enclosure. But it may be preferable to have the sensor operate by using RF technology to transmit and receive the requisite information as necessary. The operation of this embodiment is governed by the hydraulic force generating means. Starting with atmospheric pressure in the enclosure; when the atmospheric pressure inside the enclosure is reduced by the pressure varying means, assuming the hermetic properties are not compromised, the hydraulic pressure can be increased thereby counteracting the effects of the external pressure. The basic operating principle is that over pressure at the surface of the enclosure can be balanced by increasing the pressure in the hydraulic tubes.

Example 2C (Example 2B Further Comprising a Line Force Generating Means)

In finishing the enclosure of Example 2C, prior to attaching the front and back plates finely machine line grooves into the outside faces of the front and back plate. Also finely machine the line grooves into the enclosure frame and the attachment frame so that the line grooves of the frame, attachment frame and front and back plates will line up to comprise a continuous groove on assembly.

After assembly attach a bridge to the frame of the enclosure. The bridge should have a ratchet (driven by an electric motor for automatic operation) and should also have eyes for holding the lines. The lines are then laid out across the front and back wall in the line grooves and connected tightly to the eyes in the bridge.

A pressure sensor may also be added to the interior of the enclosure prior to adding the front wall. The sensor could be operated by a wire running through the pneumatic line into the enclosure. But it may be preferable to have the sensor operate by using RF technology to transmit and receive the requisite information as necessary. The lines may then be automatically tightened according to information provided by the pressure sensor. This would normally occur when a pressure sufficiently above atmospheric is created by the pressure varying means within the enclosure.

Example 3 (Strut Force Generating Means—Fixed Wall)

Prepare a frame having three to five millimeters thickness. Hermetically attach a back plate or wall to this frame, preferably made from a material having one tenth the acoustic impedance of the frame material. The attachment may be made by means of an attachment frame that fits over the back plate and hermetically seals it against the frame. The attachment frame may be made of either the frame material or the back plate material. And the frame and the attachment frame may be made of metal or any other material capable of the handling of forces upwards of one hundred pounds.

The frame should have an opening for accepting the hermetic placement of an external valve. This valve will have a conduit to the interior of the enclosure and on the external side enable connection to a pressure varying means including the means for admitting and removing.

Attach struts in a geometrically uniform pattern to the back plate (A geometrically uniform pattern may involve placing the struts in a connected triangular configuration, in a connected square configuration, in a connected pentagonal configuration, etc.). The distance between the struts and the number of struts must be calculated by taking in to account the maximum possible force on the back or front plate and dividing that by the bearing capacity of a strut and also taking into account the bearing and flexure properties of the front or back plate and frame etc. In general one strut per square inch should be sufficient for most materials which might comprise the struts.

Furthermore, the struts (which would in this embodiment be about three millimeters long, and no longer than five millimeters) are preferably made from a back and front material, the front material having one tenth the acoustic impedance of the back material. This creates a natural sound reflectance so that sound transmitted through the front plate into the front material of a strut will substantially be reflected by the back material of the strut, thereby minimizing sound transmission through the strut and enclosure. If the frame is preferably constructed using the same technological principles as are used for the struts, a minimizing of sound transmission through the frame will also occur. However, it is usually preferable to select the front attachment frame to have about one tenth the acoustic impedance of the frame so that the increased reflectance occurs at the boundary between the attachment frame and frame. This allows the frame to be made of one material. The back and front plates may be manufactured with nodal plates into or onto which the struts can conveniently be fitted. And after the struts have been attached to the back plate the front plate is fitted over the struts and hermetically attached to the frame. The attachment may be made by means of an attachment frame that fits over the front plate and hermetically seals it against the frame. The attachment frame may be made of either the frame material or the front plate material. And the frame and the attachment frame may be made of metal or any other material capable of the handling of forces upwards of one hundred pounds.

The enclosure is finished after the attachment of the front plate but may also have a holder for attaching the frame to a servo mechanism driven by an electric motor. The servomechanism would generally be a pole or arm for holding the enclosure in the physical space, but it would also be capable of rotation and angular movement under the action of the electric motor.

The enclosure need not be square but it should always follow the conformation of a hollow sheet. By changing the degree of evacuation with the pressure varying means and the positioning of the enclosure with the servomechanism, dynamic sound baffling can be implemented. And the struts and the frame or attachment frame may also comprise enclosure transduction nodes for actively modifying and controlling the sound passing through the struts and the frame.

Example 4 (Spring Force Generating Means—Fixed Walls)

Prepare a frame having three to five millimeters thickness or any other thickness that may be preferable. Hermetically attach a back plate or wall to this frame, preferably made from a material having one tenth the acoustic impedance of the frame material. The attachment may be made by means of an attachment frame that fits over the back plate and hermetically seals it against the frame. The attachment frame may be made of either the frame material or the back plate material. And the frame and the attachment frame may be made of metal or any other material capable of the handling of forces upwards of one hundred pounds.

The frame should have an opening for accepting the hermetic placement of an external valve. This valve will have a conduit to the interior of the enclosure and on the external side enable connection to a pressure varying means including the means for admitting and removing.

Attach springs in a geometrically uniform pattern to the back plate (A geometrically uniform pattern may involve placing the springs in a connected triangular configuration, in a connected square configuration, in a connected pentagonal configuration, etc.). The distance between the springs and the number of springs required, could be calculated by taking into account the maximum possible force on the back or front plate and dividing that by the bearing capacity of a spring and also taking into account the bearing and flexure properties of the front or back plate etc. In general one spring per square inch should be sufficient for most materials which might comprise the springs.

Furthermore, the springs (which would in this embodiment be about three millimeters long, and no longer than five millimeters) are preferably made from the same material as the frame. This takes advantage of a natural sound reflectance so that less sound should be transmitted through the front plate into a spring, thereby reducing sound transmission through the spring.

The back and front plates may be manufactured with back and front nodal plates into or onto which the springs can conveniently be fitted. And after the springs have been attached to the back plate the front plate is fitted over the springs and hermetically attached to the frame. The attachment may be made by means of an attachment frame that fits over the front plate and hermetically seals it against the frame. The attachment frame may be made of either the frame material or the front plate material. And the frame and the attachment frame may be made of metal or any other material capable of the handling of forces upwards of one hundred pounds.

The springs may also be used in combination with a solenoid to create a retracting node. The solenoid fits inside the spring and has a solenoid plate that is pressed by the spring to fit evenly against the front nodal plate during operation. The other end of the solenoid is attached to the rear nodal plate. When the solenoid is activated force is exerted pulling the solenoid plate back against the spring and compressing the spring, thereby creating a space between the spring and the front nodal plate. The entire assembly then functions as a retracting node.

Lastly the solenoid and the spring may be fastened to the back and front nodal plates. In this embodiment, when the solenoid retracts it exerts a contracting force on the enclosure. This embodiment can therefore be used to counteract pressure greater than atmospheric that may be created by the pressure varying means.

Example 5 (Line Force Generating
Means—Flexible Walls)

Using a mold for preparing a rubber or plastic product, hermetically form an annular basin made of rubber or plastic or other moldable hermetic material, said annular basin molded in one piece with a rear wall. After releasing the annular basin from the mold and testing the hermetic properties of the basin, add attachment plates to the outside wall of the annular basin, as required. The attachment plates may be made of metal or any other material capable of being attached to the annular basin, so that the handling of forces upwards of one hundred pounds is enabled.

Next attach a hermetic pipe valve to the surface of the annular basin so that this valve is suitable for connection to a pressure varying means and a means for admitting and removing. The hermetic pipe valve is connected to the pressure varying means and in particular to the high pressure output which is used to increase the pressure in the annular basin to above atmospheric or the reduction of the pressure in the enclosure to below atmospheric.

The front and back wall of the enclosure may have attachment plates already attached to them. If not, after the front wall is attached, attach attachment plates to both the front and back wall, said attachment plates further comprising lines attached to said attachment plates. When the enclosure is evacuated the lines can be put under tension to counteract the external pressure when present. The annular basin should also have attachment plates comprising lines that can be tightened to counteract the external pressure, when present. The attachment plates will have eyes or other attaching elements for making attachments to the line force generating means. The line force generating means will then be able to preferably position the enclosure in the physical space or it may exert forces to effect changes in the shape of the enclosure. These forces should be kept sufficiently small so that the hermetic properties of the enclosure are not compromised.

A pressure sensor may also be added to the interior of the enclosure prior to adding the front wall. The sensor could be operated by wiring running through the pipe insert or the pipe and into the enclosure. But it may be preferable to have the sensor operate by using RF technology to transmit and receive the requisite information as necessary.

The operation of this embodiment is governed by the line force generating means. Starting with atmospheric pressure in the enclosure; when the enclosure is held under tension by the lines in the physical space under consideration the pressure varying means may be used to reduce the internal pressure within the enclosure. The basic operating principle is that the external pressure acting on the enclosure is then counteracted by the force exerted through the lines of the line force generating means.

The tension on the lines may be increased or decreased by means of pulleys attached to electric motors. Or the lines may be attached to solenoids that increase the tension by retracting the lines. Manual operation using a winch or its equivalent is optional.

Example 5A (Example 5 Further Having an
Electric Force Generating Means for Resisting
Internal Pressure—Flexible Walls)

Construct and enclosure according to the procedure of example 5, ensuring that the annular basin is moulded suitably for the attachment of a pressure varying means. Release the annular basin from the mold and test the hermetic properties of the annular basin, when possible, Before attaching the front wall to the annular basin, to the back wall attach small electromagnets that are organized into a rectangular grid which may be made of squares, each side of said squares comprised of one of said small electromagnets. And after the same fashion, attach small electromagnets that are organized into a rectangular grid, which may made of squares, to the front wall. The distance between the electromagnets and the number of electromagnets must be calculated by taking in to account the maximum possible pressure on the back and front wall, including the pressure on the frame, and dividing that by the bearing capacity of the electromagnetic node, which is equivalent to one intersection of the grid. The bearing and flexure properties of the front or back wall etc. should also be taken into account. To get a rough idea of the number of nodes required, the total expected pressure can then be divided by the bearing capacity of the electromagnetic node. In general one grid square of electromagnets per square inch may be a sufficient approximation for most conditions.

The back and front walls may be manufactured with attachments into or onto which the electromagnets can conveniently be fitted. The attachments could be slots or holders designed to accept and hold the electromagnets in position. And after the electromagnets have been attached to the back wall and the front wall, the front wall is hermetically attached to the open side of the annular basin. Next add attachment plates to the outside wall of the annular basin, as required. The attachment plates may be made of metal or any other material capable of being attached to the annular basin so that the handling of forces upwards of one hundred pounds is enabled.

The electromagnetic grids of the front wall may be simplified to use only permanent magnets. In operation, an attractive polarity is needed when the pressure varying means is used to increase the pressure inside the enclosure above atmospheric, while a repulsive polarity is required when the pressure within the enclosure is reduced below atmospheric. However, since the line force generating means of Example 5 is capable of handling compression of the enclosure, it is only necessary for the electromagnets to operate in the attractive mode. In all instances the controlling means would, by using sensor info, ensure that the pressures created in the enclosure, or outside the enclosure, do not exceed the rating of the force generating means (in this case the line force generating means or the electric force generating means).

The electric nodes will have a repulsive polarity when the electromagnets are selected to have opposite polarities for each rectilinear grid on the front or back plates. Normally the electromagnets are supplied with a current that creates a pattern of all south poles at one intersection of the rectilinear grid and all north poles at another intersection of the rectilinear grid. Each north pole intersection of the grid will then be surrounded by south pole intersections and vice versa. To create attraction the back grid will then have its north poles diametrically opposite the front grids south poles and vice versa. To create repulsion the opposite is true, the back grid will have its north poles diametrically opposite the front grids north poles and vice versa. The amount of attraction or repulsion can then be controlled by changing the electric current flow through the electromagnets.

The operation of this embodiment is governed by the line force generating means in combination with the electric force generating means. Starting with atmospheric pressure in the enclosure; when the enclosure is held under tension by the lines in the physical space under consideration the pressure varying means may be used to reduce the internal pressure within the enclosure. The basic operating principle is that the external pressure acting on the enclosure is then counteracted by the force exerted through the lines of the line force generating means. Alternatively if the internal pressure is increased the electric force generating means can be used to counteract this increase.

The enclosure is finished after the attachment of the front wall but may also have holder for attaching the frame to a servo mechanism driven by an electric motor. The servo-mechanism would generally be a pole or arm for holding the enclosure in the physical space, but it would also be capable of rotation and angular movement under the action of the electric motor.

Example 6 (A Lever Force Generating Means—Flexible Walls, External Nodes)

Using a mold for preparing a rubber or plastic product, hermetically form an annular basin made of rubber or plastic or other moldable hermetic material, said annular basin molded in one piece with a rear wall and; said annular basin further having an external central groove.

The annular basin may be made of rubber or plastic or any other moldable hermetic material, and may also have an opening for accepting the placement of an external valve located on the surface of the annular basin. This is only necessary when the connection of a pressure varying means to the basin is contemplated and embodiments that do not use a pressure varying means would not have this opening.

After releasing the annular basin from the mold and testing the hermetic properties of the tube, attach an external frame by fitting the external frame into the external central groove. The external frame and the nodal attachment plates may be made of metal or any other material capable of being attached to the annular basin so that the handling of forces upwards of one hundred pounds is enabled. Next, apply and hermetically seal a front wall to the open side of the annular tube. Alternatively, the annular basin could be molded in one piece with a rear and a front wall.

The external frame will have two connected gears axially mounted on each side of the external frame. Each gear should have two pivots attached to two levers connected to either the front or the back grid. The levers ride on opposing fulcrums projecting from the external frame. The distal end of each lever is attached to either the front or the back grid and the interstices of the respective grids are attached to nodal plates on the front and back plates of the enclosure, respectively. The gears should be close enough to mesh so that when a gear is turned its counterpart gear turns also and vice versa.

The front and back grids will be attached to nodal attachment plates on the front and back wall of the enclosure. This attachment may be by lines or external struts or any other convenient mechanism. When the gears are turned to extend the levers, the distance between the grids is increased, thereby causing the enclosure walls to move apart and creating a vacuum within the enclosure. And a third gear is attached by a synchronizing shaft to its opposite number so that the two connected gears axially mounted on each side of the external frame may be synchronized. Therefore the gears on both sides of the frame should rotate at the same rate and for the same distance. The third gear will co-ordinate the rotating force that may be applied by an active element such as an electric motor. The electric motor may be connected to the third gear and the synchronizing shaft, or it could be connected to one of the other gears.

If the embodiment requires it, next attach a hermetic pipe valve to the outside layer of the annular basin so that these valves are suitable for connection to a pressure varying means and a means for admitting and removing. The hermetic pipe valve is connected to the pressure varying means and to the high pressure output which is used to increase the pressure in the annular basin to above atmospheric, or to reduce the pressure in the enclosure to below atmospheric.

A pressure sensor may also be added to the interior of the enclosure prior to adding the front wall. The sensor could be operated by a wire running through the pipe insert or the pipe and into the enclosure. But it may be preferable to have the sensor operate by using RF technology to transmit and receive the requisite information as necessary.

Example 7 (Electric Force Generating Means—Fixed Walls, Expanding Nodes)

Prepare a frame having three to five millimeters thickness or any other thickness as may be preferable. Hermetically attach a back plate or wall to this frame, preferably made from a material having one tenth the acoustic impedance of the frame material. The attachment may be made by means of an attachment frame that fits over the back plate and hermetically seals it against the frame. The attachment frame may be made of either the frame material or the back plate material. And the frame and the attachment frame may be made of metal or any other material capable of the handling of forces upwards of one hundred pounds. The frame will have an opening for accepting the hermetic placement of an external valve. This valve will have a conduit to the interior of the enclosure and on the external side enable connection to a pressure varying means including the means for admitting and removing.

To the back plate attach small electromagnets organized into a rectilinear grid, which may made of squares, each side of said squares comprised of one of said small electromagnet. And after the same fashion, attach small electromagnets organized into a rectilinear grid made of squares, to the front plate. The distance between the electromagnets and the number of electromagnets must be calculated by taking in to account the maximum possible expected force on the back or front plate and dividing that by the bearing capacity of an electromagnetic node, and also taking into account the bearing and flexure properties of the front or back plate etc. In general one rectangular element of the grid is made up of four electromagnets comprising the four sides of the rectangular element, and may generally be called and electric node. One electric node per square inch should be a sufficient approximation for most conditions.

The back and front plates may be manufactured with nodal plates into or onto which the electromagnets can conveniently be fitted. And after the electromagnets have been attached to the back plate and the front plate, the front plate is hermetically attached to the frame. The attachment may be made by means of an attachment frame that fits over the back plate and hermetically seals it against the frame. The attachment frame may be made of either the frame material or the front plate material. And the frame and the attachment frame may be made of metal or any other material capable of the handling of forces upwards of one hundred pounds. The electromagnetic grids of the front plate may be selected to have an attractive polarity or a repulsive polarity. A repulsive polarity is selected when the enclosure is under evacuation, while an attractive polarity is selected when the pressure varying means is used to increase the pressure inside the enclosure above atmospheric.

The electric nodes will have a repulsive polarity when the electromagnets are selected to have opposite polarities for each rectilinear grid on the front or back plates. Normally the electromagnets are supplied with a current that creates a pattern of all south poles at one intersection of the rectilinear grid and all north poles at another intersection of the rectilinear grid. Each north pole intersection of the grid will then be surrounded by south pole intersections and vice versa. To create attraction the back grid will then have its north poles diametrically opposite the front grids south poles and vice versa. To create repulsion the opposite is true, the back grid will have its north poles diametrically opposite the front grids north poles and vice versa. The amount of attraction or repulsion can then be controlled by changing the electric current flow through the electromagnets.

The enclosure is finished after the attachment of the front plate but may also have holder for attaching the frame to a servo mechanism driven by an electric motor. The servo-mechanism would generally be a pole or arm for holding the enclosure in the physical space, but it would also be capable of rotation and angular movement under the action of the electric motor.

The enclosure need not be square but it should always follow the conformation of a hollow sheet. By changing the degree of evacuation with the pressure varying means and the positioning of the enclosure with the servomechanism, dynamic sound baffling can be implemented.

Example 8 (Line Force Generating Means for Constructing an Acoustic Lens; Internal and External Nodes, Flexible Walls)

Using a mold for preparing a rubber or plastic product, hermetically form a tube having the shape of an elliptic paraboloid when placed under internal pressure.

The tube made of rubber or plastic or any other moldable hermetic material, may also have openings for accepting the placement of an external valve located in the outside layer of the tube. And the pipe may also be used to carry an electric conductor into the tube.

After releasing the pneumatic tube from the mold and testing the hermetic properties of the tube, add attachment plates to the outside and inside of the tube wall, as required. The attachment plates may be made of metal or any other material capable of being attached to the tube so that the handling of forces upwards of one hundred pounds is enabled.

Next attach a hermetic pipe valve to the outside layer of the tube so that this valve is suitable for connection to a pressure varying means and a means for admitting and removing. The hermetic pipe valve is connected to the pressure varying means by a pipe and in particular can make a connection to the high pressure output of the pressure varying means which could be used to increase the pressure in the tube to above atmospheric, and create the convex effect of the elliptic paraboloid shape for the tube.

Next attach attachment plates to both sides of the elliptic paraboloid tube, the attachment plates further comprising lines attached to the attachment plates. The attachment plates will have eyes or other attaching means to which the lines of the line force generating means may be attached. The line force generating means will then be able to position the enclosure in the physical space or it may exert forces to effect changes in the shape of the enclosure by adjusting and tensioning the lines. These forces should be kept sufficiently small so that the hermetic properties of the enclosure are not compromised.

The internal lines having a connection to the attachment plates inside the tube are further connect to a central line node, having electric motors and/or solenoids, or other means, for tightening the interior lines as may be required. When the tension on the lines from the central node is increased, corresponding lines attached to the exterior attachment plates may have their tension reduced, to allow that section of to tube to be pulled in. This adjustment can be continued until the elliptic paraboloid shape is converted to the shape of a convex lens.

When the enclosure is evacuated the exterior lines can be put under tension to counteract the external pressure when present. This may be accomplished by running the lines over pulleys slaved to electric motors that are used to exert tension on the lines. And solenoids may be attached to the lines so that when they are actuated the lines are tightened so that the convex or concave shape of the acoustic lens is made evident, as may be preferable.

A pressure sensor may also be added to the interior of the enclosure prior to adding the front wall. The sensor could be operated by a wire running through the pipe insert or the pipe and into the enclosure. But it may be preferable to have the sensor operate by using RF technology to transmit and receive the requisite information as necessary.

The operation of this embodiment is governed by the line force generating means. Starting with atmospheric pressure in the enclosure; when the enclosure is held under tension by the lines in the physical space under consideration the pressure varying means may be used to reduce the internal pressure within the enclosure. The basic operating principle is that the external pressure acting on the enclosure is then compensated for by the force exerted through external lines by the line force generating means. Alternatively, the pressure varying means may be used to increase the internal pressure within the enclosure. The basic operating principle is that the internal pressure then acting on the enclosure is then compensated for by the force exerted through the central node and the internal lines by the line force generating means.

The tension on the lines may be increased or decreased by means of pulleys attached to electric motors. Or the lines may be attached to solenoids that increase the tension by retracting, possibly in combination with levers or a lever force generating means.

Example 9 (Line Force Generating Means Combined with a Pneumatic Force Generating Means and a Spring Force Generating Means to Create a Tetrahedron (Polyhedron); Internal and External Nodes, Fixed Walls)

Prepare a frame having three to five millimeters thickness, or any other thickness as may be preferable. Hermetically attach a back plate or wall to this frame, preferably made from a material having one tenth the acoustic impedance of the frame material. The attachment may be made by means of an attachment frame that fits over the back plate and hermetically seals it against the frame. The attachment frame may be made of either the frame material or the back plate material. And the frame and the attachment frame may be made of metal or any other material capable of the handling of forces upwards of one hundred pounds.

The frame will have an opening for accepting the hermetic placement of an external valve. This valve will have a conduit to the interior of the enclosure and on the external side enable connection to a pressure varying means including the means for admitting and removing.

The frame will furthermore have a triangular shape suitable for comprising one side of a tetrahedron and central grid notches for accommodating an internal grid by fitting the internal grid into the internal grid notches. The internal grid will have grid holders for attaching to the central grid notches and nodal holders for holding on to the sets of parallel cross-linking springs. The first set of parallel cross-linking springs is attached to the nodal holders of the internal grid and to the rear of the internal grid. Then the internal grid is further attached by nodal holders to a second set of mutually parallel cross-linking springs attached to the front of the internal grid. The first and second set of parallel cross-linking springs run perpendicularly to each other.

And after the cross-linking springs have been attached to the internal grid, the front plate is hermetically attached to the frame. The attachment may be made by means of an attachment frame that fits over the back plate and hermetically seals it against the frame. The attachment frame may be made of either the frame material or the front plate material.

Next add attachment plates to the outside wall of the frame, if required. In particular the vertices on the triangles should have attachment plates so that a line force generating means can be applied to them. The internal grid and the attachment plates may be made of metal or any other material capable of being attached to the frame so that the handling of forces upwards of one hundred pounds is enabled Next, create three more triangular enclosures as shown above, so that they can be joined together to comprise the tetrahedral polyhedron or tetrahedron, Create a pneumatic tube that can be joined to the vertices of the tetrahedron. The pneumatic tube should be divided into sections of a length corresponding to the length of the sides of the tetrahedron. The pneumatic tube could have a connection to the pressure varying means or it could be filled independently through a regular high-pressure valve. The pneumatic tube is sealed to the edges of the tetrahedron and provides stability and resilience to the geometry of the tetrahedron.

The attachment plates will have eyes or other attaching means for connecting to the lines of the line force generating means. The line force generating means will then be able to position the enclosure in the physical space under consideration. The forces should be kept sufficiently small so that the hermetic properties of the enclosure are not compromised. In any event, at least four lines should be attached to the tetrahedron, each vertex having at least one line attached to it.

A pressure sensor may also be added to the interior of the enclosure prior to adding the front wall. The sensor could be operated by a wire running through the pipe insert or the pipe and into the enclosure. But it may be preferable to have the sensor operate by using RF technology to transmit and receive the requisite information as necessary.

The operation of this embodiment is governed by the pressure varying means in combination with the line force generating means and the spring force generating means. Starting with atmospheric pressure in the enclosure; when the enclosures are held under tension in the tetrahedral configuration by the lines in the physical space under consideration the pressure varying means may be used to reduce the internal pressure within the enclosure. The basic operating principle is that the external pressure acting on the enclosure is then compensated for by the force exerted through the springs be the spring force generating means.

The tension on the lines may be increased or decreased by means of pulleys attached to electric motors. Or the lines may be attached to solenoids that increase the tension by retracting.

Example 10 (Electric Force Generating Means Having a Positive Static Voltage Output Pole—Flexible Walls)

An electric force generating means may be used to maintain the enclosure walls against internal or external pressures. Construct the enclosure from a light hermetic material that preferably is capable of forming a flexible wall. Apply a conductive coating to the inside of the enclosures. This may be done by using a conductive spray or paint, or it could be done by laminating exposed conductive foil (aluminum foil) to the inside of the enclosure wall. And this may be put to use in two embodiments.

The first embodiment would have the conductive coating applied continuously over the entire interior surface of the enclosure. The second embodiment would have the conductive coating applied separately to the front and back wall of the enclosure, so that there is no conduction between the conductive coatings of the front and back wall. The conductive coatings will also have contact plates connected to wires. The wires in turn are connected to the negative charge reservoir or the switch by a pole wire.

After the enclosure walls (Both walls should have the same size and dimensions; they should be geometrically congruent) have been prepared they are placed on a flat work bed and aligned to overlap exactly. Then a press for eliminating air voids between the enclosure walls should apply pressure to all of the enclosure walls excepting the border, rim, or frame area of the wall. After the pressure has eliminated the air voids from between the enclosure walls, the frame area of the enclosure walls is hermetically sealed and laminated together, leaving only the pole wire extruding from the enclosure. After the pole wire is encased in a suitable sealing plug. the loci in the enclosure where the pole wire exits the enclosure is also carefully hermetically sealed with the sealing plug being inserted and sealed into the enclosure. The press is then removed and the power supply is added to the enclosure and the pole wire is connected to the static voltage output pole of the power supply.

The power supply may be contained in a casing attached to the enclosure and have a manual control for controlling the rate at which charge is being transferred to the charge plates. (When complex embodiments having many enclosures are created the power supply may be a stand-alone unit and the power should then be carried to the enclosures by a plurality of pole wires.) And the enclosure may also have a number of RF transmitter feedback circuits for signaling the separation between the enclosure walls. The power supply will then have a control for setting the preferred distance of separation between the two walls of the enclosure. And the RF feedback circuit could signal the power supply to change the rate at which charge is being transferred, as may be preferable. Therefore, when using a Van de Graaff generator the control would simply signal the drive motor to speed up or slow down, as required. When using a Tesla coil, a variable primary may be used to vary the output power as dictated by the control. And inserting a variable resistance into the charging circuit may preferably be used to regulate the amount of charge added by the Tesla coil. Also a lower voltage coil may be used instead.

A source of electric charge is required; this may be obtained by using a van de Graaff generator, a Marx bank, or a Tesla coil etc., which for convenience throughout this text may be referred to as a high voltage power supply. The high voltage power supply is attached by wiring to a negative charge reservoir and a positive charge reservoir, and can be used to supply either reservoir with the appropriate charge as indicated by the reservoir name. The charge reservoir may also have insulation applied to it, to prevent charge leakage from the reservoir to the atmosphere. And the output of the power supply should have a static voltage output pole for making connection with the pole wire.

The first embodiment is usually connected to the negative charge reservoir, although it could also be connected to the positive charge reservoir. In any event the charge on the conductive coating of this embodiment will always be uniformly negative, or positive.

The second embodiment may have the same charge on both conductive coatings, but also has a switch that provides the option of switching to an arrangement where the conductive coatings are charged to opposite polarities. The switch is connected to the bipolar conductive coating by a wire and has a first contact point and a second contact point connected by wires to the negative charge reservoir and the positive charge reservoir, respectively. The other conductive coating is permanently connected to either the negative or the positive charge reservoir.

This implies that the switch can render the electrostatic force acting in the second embodiment either attractive or repulsive depending on whether the polarities are opposite or negative or positive. The preferred distance between the walls of this embodiment is from about 1 millimeter to about 5 millimeters, or more preferably from about 2 mm. to about 4 mm, or most preferably at about 3 mm. At this distance a minor amount of charge should be effective to achieve separation between the walls by creating repulsion between the walls. The regulation of the amount of charge that is added can be carried out in a number of ways. If a van de Graaff generator is used, then regulation can be achieved by simply varying the speed of the motor that drives the generator. Alternatively when a high voltage coil arrangement such as a Tesla coil is used, inserting a variable resistance into the charging circuit can be used to regulate the amount of charge added. And a variable primary may also be used to vary the output power as dictated by the control.

A loop shaped to conform to the perimeter of the enclosure wall may be fashioned from resilient wire or plastic, or any other suitable material. The loop may be added or attached to the perimeter of the enclosure to keep the enclosure fully stretched and taut and to keep folds from appearing on the enclosure surface. To complete the frame of the enclosure, the loop would then preferably be connected to the power supply casing.

This embodiment, should therefore function well when dealing with enclosures of light construction.

Example 11 (Electric Force Generating Means Having a Positive Static Voltage Output Pole and a Plurality of Charge Plates—Flexible Walls)

An electric force generating means may be used to maintain the enclosure walls against internal or external pressures. Construct the enclosure from a light hermetic material that preferably is capable of forming a flexible wall. Apply a grid of conductive plates to what will become the inside surface of the flexible enclosure wall. This may be done by using a conductive spray or paint in combination with a masking stencil to ensure that areas of the inside surface will remain non-conductive, or it could be done by laminating conductive foil plates (aluminum foil could be used) to the inside surface of the flexible enclosure wall. Next, a wiring grid is laid out on the inside surface of the flexible enclosure wall, so that each of the conductive plates is connected to a separate wire or conductive lead of the wiring grid. The conductive plates should have just enough separation to allow the wiring grid to be laid out without incurring the danger of a short circuit. A thin plastic insulating sheet of minimum thickness may also be applied over the conductive plates and the wiring grid after they have been laid on. And it may be preferable to use diodes in the connection of each of the conductive plates to the wiring grid; this should enable the conductive leads to be connected to feeder wires which in turn could be connected to a pole wire that connects to the static voltage output pole of the power supply. The diodes are placed so as to only allow charge transfer from the output pole to the charge plates. Current flow from the charge plates to the output or to other charge plates is blocked by the diodes. This should greatly simplify the construction of the wiring grid.

For a single enclosure, the power supply would generally be located in a casing that is attached to the enclosure. (When complex embodiments having many enclosures are created the power supply may be a stand-alone unit and the power should then be carried to the enclosures by a plurality of pole wires.) If the enclosure is meant to be hung from a ceiling or other support, the power supply casing may reside at the top of the enclosure. If the enclosure were made to rest on the floor, the power supply casing would generally reside at the bottom of the enclosure. And the power supply is simply a source of electric charge as may be provided by a Van de Graaff generator, a Tesla coil, although lower voltage coils may suffice, or any other electrostatic charge generating device capable of providing the requisite amount of charge to the charge plates.

After the enclosure walls (Both walls should have the same size and dimensions; they should be geometrically congruent) have been prepared they are placed on a flat work bed and aligned to overlap exactly. Then a press for eliminating air voids between the enclosure walls should apply pressure to all of the enclosure walls excepting the border, rim, or frame area of the wall. After the pressure has eliminated the air voids from between the enclosure walls, the frame area of the enclosure walls is hermetically sealed and laminated together, leaving only the pole wire extruding from the enclosure. After the pole wire is encased in a suitable sealing plug, the loci in the enclosure where the pole wire exits the enclosure is also carefully hermetically sealed with the sealing plug being inserted and sealed into the enclosure. The press is then removed and the power supply is added to the enclosure and the pole wire is connected to the static voltage output pole of the power supply.

The power supply may have a manual control for controlling the rate at which charge is being transferred to the charge plates. And the enclosure may also have a number of RF transmitter feedback circuits for signaling the separation between the enclosure walls. The power supply will then have a control for setting the preferred distance of separation between the two walls of the enclosure. And the RF feedback circuit will signal the power supply to change the rate at which charge is being transferred, as may be preferable. In either case, when using a Van de Graaff generator the control would simply signal the drive motor to speed up or slow down, as required. When using a Tesla coil, a variable primary may be used to vary the output power as dictated by the control. Also, inserting a variable resistance into the charging circuit can be used to regulate the amount of charge added by the Tesla coil. Also a lower voltage coil may be used instead. The dome of the van de Graaff generator or the torus of the Tesla coil may also have insulation applied to it, to prevent charge leakage into the atmosphere. And the output of the power supply should have a static voltage output pole for making connection with the pole wire.

The preferred distance between the walls of this embodiment is from about 1 millimeter to about 5 millimeters, or more preferably from about 2 mm. to about 4 mm, or most preferably at about 3 mm. At this distance a minor amount of charge should be effective to achieve separation between the walls by creating repulsion between the charge plates. And adding more charge will have the effect of overcoming the external pressure that is created by the atmosphere.

And a loop shaped to conform to the perimeter of the enclosure wall may be fashioned from resilient wire or plastic, or any other suitable material. The loop may be added or attached to the perimeter of the enclosure to keep the enclosure fully stretched and taut and to keep folds from appearing on the enclosure surface. To complete the frame of the enclosure, the loop would then preferably be connected to the power supply casing.

The electric force generating means controls this embodiment. A means for varying is not required since the vacuum is created when the empty or non-existent space between the enclosure walls is expanded.

Example 11a (Example 11 Having a Positive and a Negative Static Voltage Output Pole—Flexible Walls)

This embodiment would have the charge plates of the first wall of the enclosure connected to the positive static voltage output pole and the charge plates of the second wall of the enclosure connected to a switch. The switch in turn is capable of making electrical connection with either the positive or the negative static voltage output pole or the power supply.

The embodiment of Example 11 is usually connected to the positive charge reservoir, although it could also be connected to the negative charge reservoir. In any event the charge on the conductive coating of this embodiment will always be uniformly negative, or positive.

Example 11a may have the same charge on the conductive plates of both enclosure walls, but it also has a switch that provides the option of switching to an arrangement where the conductive plates on the first enclosure wall are charged to the opposite polarity or the conductive plates on the second enclosure wall. The switch is connected to the conductive plates on the second enclosure wall by the wiring grid, and has a first contact point and a second contact point connected by wires to the negative charge reservoir and the positive charge reservoir, respectively. The conductive plates of the first enclosure wall are permanently connected to either the negative or the positive static voltage output pole. And the wiring grid of this embodiment is split into two parts, the first part of the wiring grid making electric connection to the first enclosure wall and the second part of the wiring grid making electric connection to the second enclosure wall.

This implies that the switch can render the electrostatic force acting in this embodiment either attractive or repulsive depending on whether the polarities are opposite or negative or positive. And the positive and negative static voltage output poles of the power supply can be charged by using two Van de Graaff generators, one with a negative static voltage dome, and the other with a positive static voltage dome. Alternatively two Tesla coils could be used instead, although lower voltage coils may suffice.

Example 11b (Example 10, 11, or 11a, Further Having a Pressure Varying Means—Flexible Walls)

Example 10, 11, or 11a, could further have a pressure varying means added to them.

In this embodiment a hermetic pipe valve may be attached to the enclosure so that this valve is suitable for connection to a pressure varying means and a means for admitting and removing. The hermetic pipe valve is connected to the pressure varying means by a hermetic pipe or tube and in particular can make a connection to the high-pressure output of the pressure varying means that could be used to increase the pressure in the enclosure to above atmospheric. Or the means for admitting and removing could lower the pressure to below atmospheric.

Using a pressure varying means allows the enclosure to have variable sound and temperature transmission, whereas the embodiments of Example 10, 11, or 11a, were only capable of switching between total sound baffling and total sound transmission. This embodiment may therefore be used when more flexibility in the handling of sound is desired.

If a pressure varying means is used in combination with Example 11, or the first embodiment of Example 10, only the means for admitting and removing should be allowed to operate, since Example 11, or the first embodiment of Example 10, are only capable of creating repulsion. If the full scope of the pressure varying means is to be applied Example 11a must be used because it can switch from the repulsive state to the attractive state. The charge plates will have to enter the attractive state to overcome the internal pressure that could be created by the means for varying.

Example 11c (Example 11 or 11a or 11b Further Having a Nodal Means—Flexible Walls)

It may be preferable to add a nodal means for controlling the charge plates. A nodal means can be constructed by using SCRs instead of diodes. The SCRs will be triggered by an output from a PROM nodal chip or a standard chip that is capable of serving as a nodal chip and handling the specific electronic problem to suit.

The nodal chip essentially controls the activation of the SCRs to the conductive state and will have one output for each of the SCRs in the enclosure. Therefore the nodal chip can switch any permutation of SCRs into the conductive state, thereby allowing the corresponding charge plates to be charged.

On the input side the nodal chip will have the ability to receive a signal from the controlling means and to convert that signal into a digital representation presented on the nodal chip output leads, as comprising either activating voltages for the SCRs or comprising neutral voltages that are insufficient to activate the SCRs. Therefore for eight charge plates in the enclosure, eight output leads would be required. For sixteen charge plates, sixteen output leads would be required. And if the number of charge plates rises further, a single chip may not suffice and an electronic nodal circuit may have to be constructed so that the appropriate number of output leads is made available to control the SCR's.

A vacuum may also be used to improve the sound baffling characteristics of ear protectors and headphone sets. As is well known the ear protectors are used to protect the ears from excessive ambient noise. And a prevalent problem with headphone sets is the interference of ambient noise with the audibility and perceived rendition of the rendered sound. This may be alleviated by introducing an vacuum for baffling the ambient noise. However there are some other sound baffling improvements that may be made to ear protectors and headphone sets as well.

Figure 14:
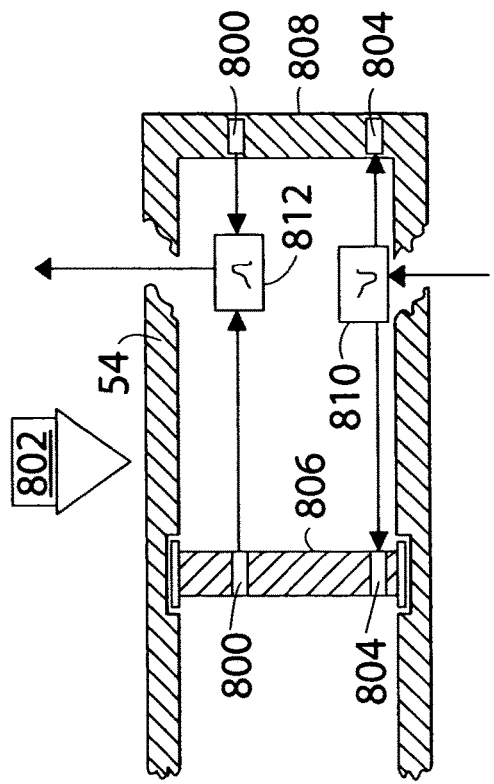
FIG. 14 shows a sound canceling transduction circuit.
Figure 15:
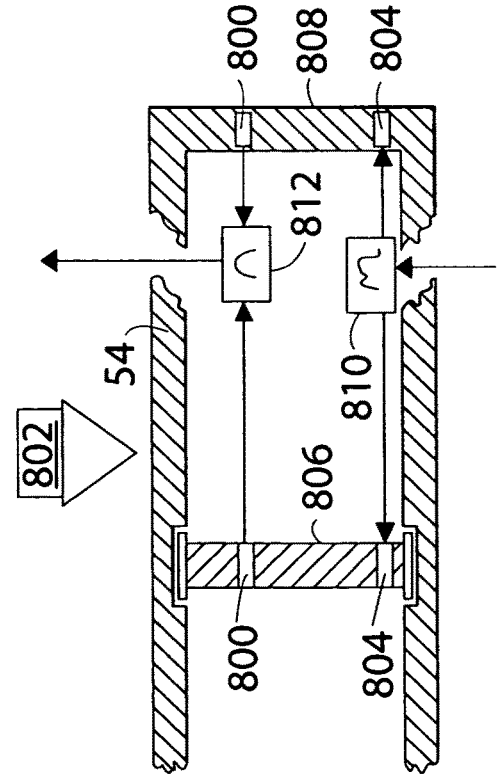
FIG. 15 shows a modulation transduction circuit.
Figure 16:
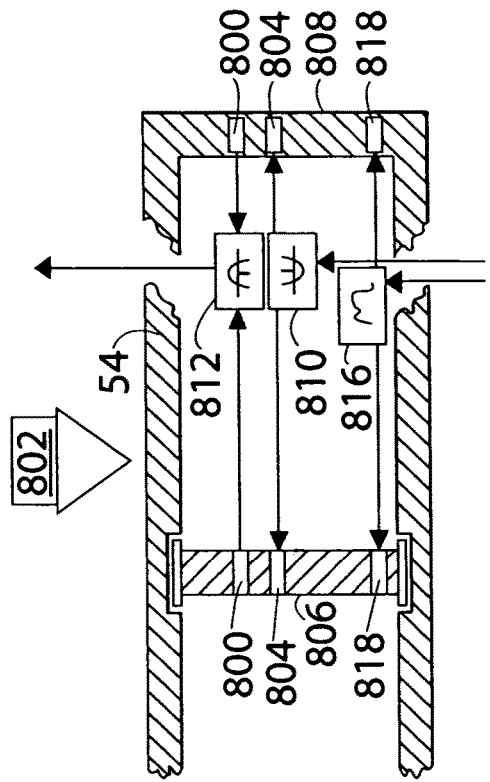
FIG. 16 shows a modulated noise canceling transduction circuit.
Figure 17:
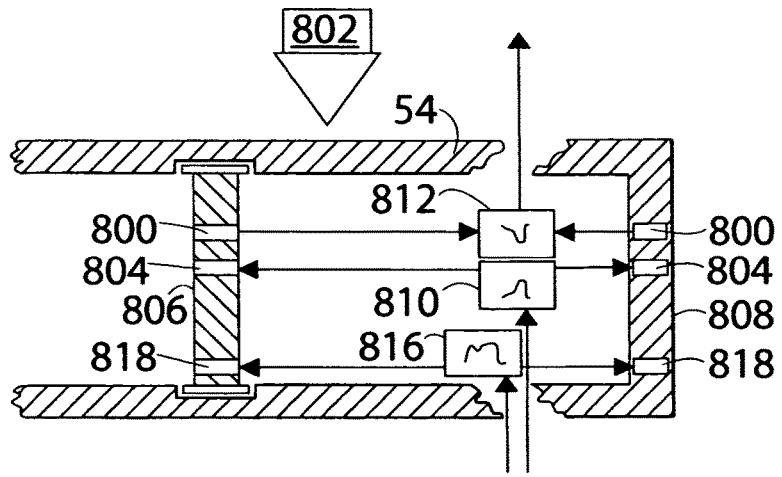
FIG. 17 shows a modulated sound canceling transduction circuit.
Figure 18:
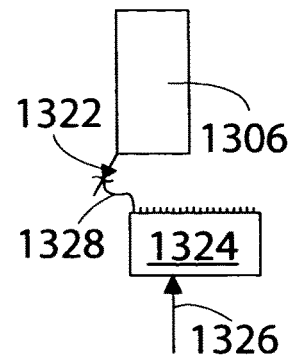
FIG. 18 shows a nodal chip assembly; the nodal chip is used to demultiplex a signal from the controlling means to select nodes for actuation.
Figure 19:
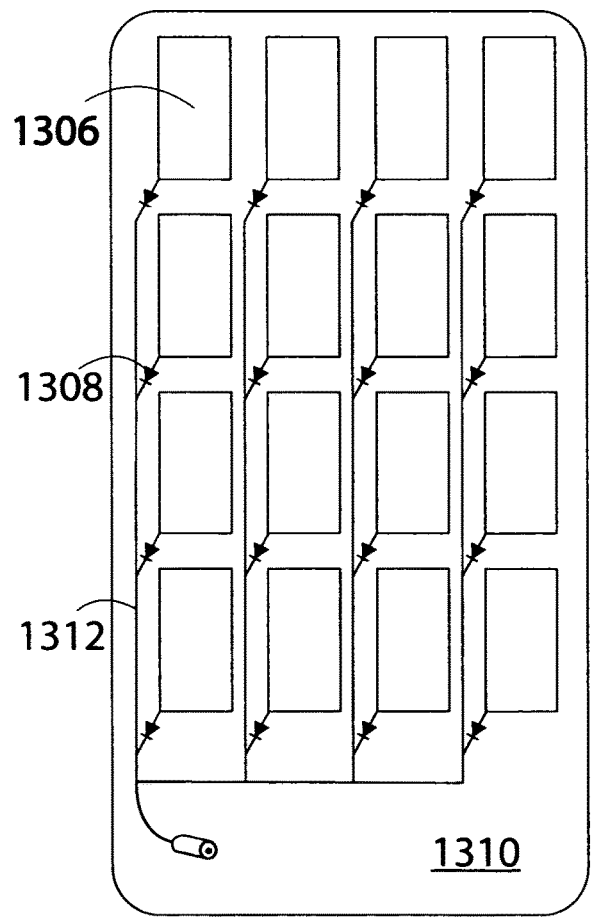
FIG. 19 shows a flexible enclosure wall having a matrix of conductive plates affixed thereto.
Figure 20:
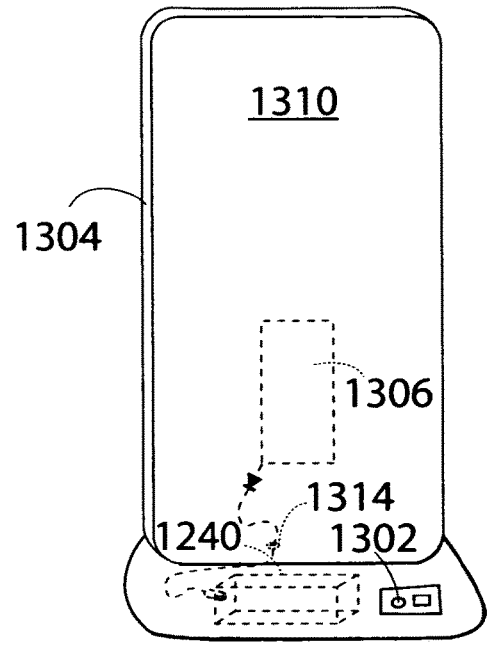
FIG. 20 depicts a flexibly walled enclosure supported by a power supply casing or stand.
Figure 21:
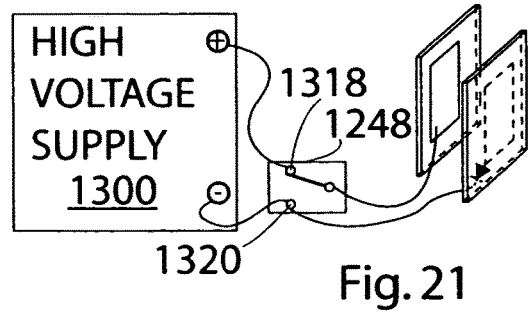
FIG. 21 depicts a charged plate assembly connected to a switch and a high voltage power supply.

Accordingly, a more specific aspect of the invention is shown in FIGS. 14 and 15 which depicts the invention in combination with a set of ear protectors having two sound baffling cups (354, 356) for fully enclosing the ears between said sound baffling cups and the head and neck during operation, and a fitting means (358) for placing said sound baffling cups against the ears, the improvement comprising;

A cushioned lip contour (360, 362) for complimenting the shape of the head and neck during operation, said cushioned lip contour applied to the lips (364, 366) of said sound baffling cups such that said cushioned lip contour curves the lips of said sound baffling cups laterally (368) away from the head where it touches the jaw bone and the side arch of the skull, and said cushioned lip contour curves the lips of said sound baffling cups medially (370) towards the head and neck where it touches the human body surface beneath the jaw bone and behind the lower external ear, so that the comfort, fit, and sound baffling qualities of said sound baffling cups are substantially improved by said cushioned lip contour, thereby reducing the ambient noise reaching the ears during operation.

Some previously available devices did not have contours. As shown in FIG. 15, since the head and neck have numerous contours, a contoured device provides a better fit and comfort. Also the exclusion and baffling of sound is to some extent dependent on the ability of the sound baffling cups to seal against the head and neck, because this prevents the sound from entering through gaps where the lips of the sound baffling cups are joined against the head and neck. A cushioned lip contour aids in achieving a proper seal, especially under conditions of stress, where the head and neck are bent or when the sound baffling cups are jarred by external contact.

If we consider the lips of previously available sound baffling cups to lie in a sagittal plane parallel to the side of the head during operation, then the cushioned lip contour diverges from this plane by curving laterally (368) away from the head and neck directly above the jawbone (372). Beneath the jawbone and the lower external ear (374) the contour diverges from this plane by curving medially (370) towards the head and neck. This compensates for the hollow of the human body surface found just beneath where the head and neck and jawbone join. Then, behind the external ear, the contour moves back towards and into this plane, lying substantially in this plane above the external ear.

It may be preferable to wear sound baffling cups having a lip contour in combination with a headband. The sound baffling cups may come with or without internal speakers. One such combination uses a reversible headband clip attached to the exterior surface of the sound baffling cups so that the headband clip may be extended upward to hook over the headband, or the headband clip may be reversed to extend downward to allow the headband to be fitted between the headband clip and the outside of the sound baffling cups.

When the headband clip is extended upward the sound baffling cups may also have a neck straps attached to a strap attachment. The neck straps are used to fit the sound baffling cups against the ears. When the headband clip is extended downward the sound baffling cups can be used with a regular headband fitted through the headband clip, although the headband has to be worn at a steep angle to allow the sound baffling cups to fit properly against the ears.

And the sound baffling cups may have two fixed headband clips attached to their exterior. The first fixed headband clip is attached at the center of the dorsal face of the sound baffling cups. The second fixed headband clip is slightly lower than the first and offset to the anterior of the sound baffling cups. The sound baffling cups can be used with a regular headband fitted through the fixed headband clips, although the headband has to be worn at a steep angle to allow the sound baffling cups to fit properly against the ears.

The sound baffling cups may also come with a surrogate headband attached. The surrogate headband will come in two parts, the first part attached to the anterior of the sound baffling cups and the second part attached to the posterior of the sound baffling cups. When a surrogate headband is attached, the sound baffling cups should not have a lip contour; instead they should have an annular opening resident in one plane.

This embodiment may be worn in the regular headband style or it may be worn with the band looping around the top of the head and underneath the chin. Because the cups must shift position when worn in one style or the other, the lip contour would not be appropriate for this embodiment. However, a lip contour may be used with this embodiment when the intended use is restricted to one of the two styles.

And complementary contours may be custom made by using a mould made from castings of the external ear. It may therefore be preferable that the complementary contour of said fitting means is created by a mould made from castings of a specific external ear, so that the complementary contour of said fitting means is customized to fit said specific external ear. Such a mould may be made from standard casting techniques and can then be used to create complimentary contours for customized head phone sets and ear protectors.

However, to minimize the sound that may travel through gaps between the contour and the external ear during operation, a skin adhering material may be used. It may therefore be preferable that said cushioning material or complementary contour has a binding preference for skin, said binding preference substantially sealing said cushioning material or complementary contour against the external ear, so that the fit and sound baffling characteristics of said device are substantially improved.

As further shown FIGS. 21, 22, 23, and 24, according to another particular the invention is comprised of a jointed flexible curved clip having two parts, the first part (460) shaped to fit the curvature of the anterior half of the lip (462) of said sound baffling cups, the second part (464) shaped to fit the curvature of the posterior half of the lip of said sound baffling cups, and;

the first part of said jointed clip attached by a first hinge (466) to a first pivot (468) mounted in a seat (470) projecting from the inferior part of said sound baffling cups, the second part of said jointed clip attached by a second hinge (472) to a second pivot (474) mounted in the distal end of said first part, and;

the first and second parts of said jointed clip further having a lip groove (476, 477) for accommodating the lip of said sound baffling cups, the distal end of the second part further having a tongue (478) for latching into a tongue groove (480) located on the lateral surface (481) of said seat, such that said jointed clip further provides a firm backing for the external ear when locked in place by said lip groove and by said tongue groove, and;

the lateral surface (482) of said jointed clip having supporting material (483) for sealing said jointed clip against the ear lobe, so that when said jointed clip is pivoted to fit the lip of said sound baffling cups into said lip groove and latch said tongue in said tongue groove during operation, the supporting material of said lateral surface of said jointed clip presses laterally to seal the ear lobe against a surface selected from the group consisting of the complementary contour or the cushioning material, as the case may be, and;

the medial surface (484) of said jointed clip having a wedge shaped layer of bracing material (486) applied to it, the thicker part of said wedge shaped layer attached to the posterior circumference (488) of said second part, the thinner part of said wedge shaped layer comprising a frontal pad (490) for sealing and fitting the anterior part of said device against the head and jawbone, and;

said bracing material further having a lip contour (492) for complementing the shape of the head and neck during operation, such that said lip contour curves the bracing material of said jointed clip laterally away from the head where it touches the jaw bone and the side arch of the skull, and said lip contour curves the bracing material of said jointed clip medially towards the head and neck where it touches the human body surface beneath the jaw bone and the external ear, so that when said sound baffling cups (494) are locked in place by said jointed clip the posterior of said sound baffling cups is moved laterally by said wedge shaped layer of bracing material, thereby pressing and sealing the frontal pad against the head and jaw bone.

This embodiment is one of several that may be used to hold sound baffling cups against the ears. The clip is comprised essentially of two semicircular arcs that have a width greater than the width of the lips of the sound baffling cups. The width must also be sufficient for wedging the ear lobe upward against the cushioning material or the complementary contour as the case may be. The first part of the clip is attached by a first hinge to a first pivot located in a seat projecting from the inferior part of the sound baffling cups. The second part of the clip is attached by a second hinge to a second pivot attached to the distal end of the first part of the clip. Also the clips are designed to provide a firm backing for the ear lobe and the lips of the sound baffling cups when locked in place. They are aided in this by the lip contour and the wedge shape of the bracing material. The resulting shape braces the assembly against the head and neck and also prevents peripheral sound from penetrating through the ear lobe.

To fit the sound baffling cups against the ears, the clips are rotated away from the sound baffling cups to allow the sound baffling cups to be placed against the ears. The first part of the clip is then rotated to fit around the anterior part of the external ear until the lip of the sound baffling cups catches in the lip groove of the clip. Thereafter, the second part of the clip is rotated to fit behind the ear lobe until the lip of the sound baffling cups catches in the lip groove of the second part of the clip and the tongue latches in the tongue groove. When this operation is completed the clip will be pushing the ear lobe laterally into the complementary contour or the cushioning material as the case may be, thereby effectively sealing the external ear against the sound baffling cups.

The sealing of the ears is further aided by the lip contour applied to the medial surface of the wedge shaped layer of bracing material. The second part of the jointed clip occupies a space dimensioned somewhat like a large orange slice, with the thick part of the slice positioned along the posterior circumference of the sound baffling cups. Hence, when locked in place with the lip contoured bracing material wedged against the head and neck, the jointed clip forces the rear of the sound baffling cups and the ear lobe away from the head and neck. This in turn forces the front of the sound baffling cups inward, thereby increasing the sealing effect.

Alternatively the latching means may be comprised of a sliding clip (500), which is attached to the posterior half of the sound baffling cups (501). Essentially the sliding clip performs the same function as, and has a second arc shaped flange (502) dimensioned somewhat like the second part of the jointed clip. The first part of the jointed clip now appears as a first arc shaped flange (504) fused with the anterior half of the sound baffling cups and occupying substantially the same dimension and position as the first part of the jointed clip occupies during operation.

However, the sliding clip also has a lune shaped shell (506) having a curvature corresponding to the shape of the sound baffling cups to which it is attached. This lime shaped shell fits laterally over the posterior part of the sound baffling cups and is attached to the sound baffling cups by a holding means which may be comprised of two strips or bands of elastic material (512, 514) which are held in place by washers or plates (516, 517, 518, 519) that are cemented or fixed into the walls of the sliding clip or sound baffling cups. As shown in the drawings, the holding means allows the elastic material to be attached to both the lateral surface of the sound baffling cups and to the medial surface (520) of the sliding clip.

In operation the sliding clip is pulled back to allow the sound baffling cups to be placed against the external ear so that the first arc shaped flange is wedged in behind the anterior part of the external ear. Then, in the presence of the elastic tension, the sliding clip is guided forward so that the lune shaped shell is positioned proximally to the lateral surface (508) of the sound baffling cups. Simultaneously the second arc shaped flange, which is a part of the sliding clip, slides forward to fit in behind the posterior part of the external ear and substantially seal the second arc shaped flange against the posterior external ear and against the first arc shaped flange.

To further improve its fit the sliding clip also has a lip groove for accommodating the posterior lip of the sound baffling cups. And when the sliding clip is pushed forward to mate with the sound baffling cups, in the region where the first and second arc shaped flanges overlap, the second arc shaped flange fits laterally over the first arc shaped flange. As well, the first and second arc shaped flange have a supporting material (524, 526) for sealing the sliding clip against the ear lobe attached to their lateral surface. And the medial surfaces (528, 530) of the first and second arc shaped flange may also have a wedge shaped layer of bracing material (532) applied to them, so that the thicker part of the wedge shaped layer is attached to the posterior circumference (534) of the sliding clip and the thinner part of the wedge shaped layer comprises a frontal pad (536) attached to the first arc shaped flange, for sealing and fitting the anterior part of the device against the head and jaw bone. As said before, the wedge shaped layer of bracing material may also have a lip contour (538) for complementing the shape of the head and neck during operation. Hence, the posterior part of the device should be moved laterally by the wedge shape of the bracing material during operation, so that the frontal pad is braced against the head and jawbone.

It has been shown by the preceding discussion that the external ear provides a great platform for attaching light devices to the head. And this is best done by using a clip that is capable of encircling the external ear in operation. This may be done by using a jointed clip, a flat sliding clip, a pneumatic clip, and a hydraulic clip.

It may therefore be preferable that according to one of its aspects the invention further comprises; A latching means for proximally attaching elements to the ear, said latching means comprised of a plurality of clips selected from the group consisting of a jointed clip, a flat sliding clip, a pneumatic clip, and a hydraulic clip.

The clips will have eyes or contact facets for allowing useful devices to be attached to the clips so that they reside in functional proximity to the external ear. In particular the clips will be able to allow the attachment of sound baffling cups to the clips. The sound baffling cups may contain speakers for sound emission. And the clips should also allow the attachment of external speakers; in fact it should be possible to attach more than one external speaker.

The clips may be constructed in a number of ways. The first is as shown in the embodiment of a jointed clip. The second is by using a flat sliding clip; the flat sliding clip is like the sliding clip except that the cup and shell have been omitted. If it is desired that sound baffling cups are to operate in conjunction with the flat sliding clip then the sound baffling cups would be attached to the flat sliding clip using the eyes or contact facets. The flat sliding clip may use a holding means comprised of elastic bands as before, but the location of the holding means has shifted so that it is now located in the arc shaped flanges of the flat sliding clip.

Since the lune shaped shell is not an element of the flat sliding clip, the previous disposition of the holding means between the lune shaped shell and the sound baffling cups is no longer possible. And the join between the arc shaped flanges has also changed. The second arc shaped flange now forms a tongue, which extends into a notch in the first arc shaped flange. The actual holding means is then located between the notch and the tongue. This may be an elastic band as before, but it may be preferable that a spring-loaded plunger be used instead.

The notch creates a casing for holding the spring and the plunger. First the plunger and the spring are inserted in the casing, with the spring following around the shaft of the plunger. Then a center-drilled screw is screwed into the casing to retain the spring and the plunger. The shaft of the plunger can then be retracted through the center-drilled screw. The shaft is then attached to a holder in the tongue of the second arc shaped flange by fully retracting the plunger to make the attachment.

Thereafter the plunger will hold the two clips movably together. To attach the flat sliding clip to the ear it is merely necessary to pull the clips apart, fit them over the ears and then allow the retracting force of the plunger and the holding means to pull the clips into a comfortable fit against the ears.

The third is a pneumatic clip using pneumatic pressure. An annular casing having a central opening is fitted over the external ear to make contact with the side of the head. This annular casing contains a reservoir and an expandable annular tube connected to the reservoir and to the gas or mixture of gases in the reservoir. The annular tube is attached along the inner circumference of the annular casing. When the annular casing is placed over and around the ears to fit snugly against the side of the head, and a plunger connected to the reservoir is used to exhaust the reservoir the expandable tube expands to snugly and annularly enclose the external ear, thereby tightly fitting the pneumatic clip to the side of the head.

The fourth is a hydraulic clip using hydraulic pressure. An annular casing having a central opening is fitted over the external ear to make contact with the side of the head. This annular casing contains a reservoir and an expandable annular tube connected to the reservoir and to the hydraulic liquid in the reservoir. The annular tube is annularly attached to the inner circumference of the annular casing. When the annular casing is placed over and around the ears to fit snugly against the side of the head, and a plunger connected to the reservoir is used to exhaust the reservoir, the expandable tube expands to snugly and annularly enclose the external ear, thereby tightly fitting the hydraulic clip to the side of the head. It may also be preferable that the hydraulic fluid of said hydraulic clip is glycerin.

The plunger may be the same for both the pneumatic and the hydraulic clip. The plunger may have a locking means which, after exhausting the reservoir, allows the plunger to fit smoothly into the surface of the annular casing and which prevents it from rising above this surface until it is unlocked. The locking means may be a sliding latch, which is recessed into a latch casing in the plunger frame. The sliding latch may be spring loaded and have an upwardly rounded tip that, upon contact with the annular casing will smoothly ride back on its upwardly rounded tip to allow the plunger to be locked in place when the sliding latch is depressed sufficiently to line up with the latch hole in the annular casing. The top of the latch casing will have a sliding latch groove cut into it, thereby allowing the latch button to be used to retract the sliding latch and unlock and remove the plunger from the reservoir.

Alternatively a plunger disposed to the posterior side of the hydraulic or pneumatic clips may simply have a friction or ratchet type lock, The plunger casing containing the plunger will make strong frictional contact with the plunger so that the frictional force is higher than the force exerted by the fluid on the plunger during normal operation. After being moved into position the plunger will therefore remain in that position until it is moved to a different position. Or the plunger will have a series of small nubs that correspond to indentations in the plunger casing. When the nubs and the indentations are lined up in a certain position they will then remain in that position until the plunger is moved again, manually.

When the plunger is removed from the reservoir fluid may return to the reservoir and easily allow the annular casing to be removed from the ear.

It may therefore be preferable that according to one of its aspects the invention further comprises; a latching means for proximally attaching devices to the ear wherein;

said flat sliding clip is comprised of a first arc shaped flange having a curvature corresponding to the shape of the anterior portion of the external ear and a second arc shaped flange having a curvature corresponding to the shape of the posterior portion of the external ear, so that when said flat sliding clip is attached to the ear by wedging said second arc shaped flange in behind the posterior portion of the external ear, said first arc shaped flange may be movably fitted against the anterior portion of the external ear, so that in operation said second arc shaped flange is fitted into said first arc shaped flange by inserting a tongue protruding from said second arc shaped flange into a notch in said first arc shaped flange, so that said first arc shaped flange and said second arc shaped flange are held together by elastic tension, whereby said flat sliding clip is clasped between the external ear and the side of the head, so that said flat sliding clip comprises a means for proximally attaching devices to the ear, and;

wherein said jointed clip is comprised of a first part shaped to fit the curvature of the anterior half of the external ear, and a second part shaped to fit the curvature of the posterior half of the external ear, and;

wherein said second part of said jointed clip is attached by a hinge to a pivot mounted in the distal end of said first part;

the distal end of the second part further having a tongue for latching into a tongue groove located on the proximal end of said first part, so that when said jointed clip is attached to the external ear by wedging said first part against the anterior portion of the external ear, said second part may be movably fitted through rotation about said hinge in behind the posterior portion of the external ear, so that in operation said second part is fitted laterally over said first part and locked in place by said tongue groove, and;

said jointed clip is clasped between the external ear and the side of the head, so that said jointed clip comprises a means for proximally attaching elements to the ear, and;

wherein said pneumatic clip is comprised of an annular casing having a central opening, said annular casing further comprising a holding groove and a holding case fashioned to follow the circumference of said central opening, and;

said annular casing further comprising an annular expandable pneumatic tube and pneumatic reservoir, said annular expandable pneumatic tube held in said holding groove and said pneumatic reservoir held in said holding case, and;

said annular casing further comprising an adjustable plunger for applying a variable pressure to said pneumatic reservoir, said plunger having a latch for holding said plunger in position during operation, so that when said plunger applies pressure to said pneumatic reservoir during operation the hydraulic fluid in said pneumatic reservoir is expelled from said pneumatic reservoir into said annular expandable pneumatic tube, thereby forcing said annular expandable pneumatic tube to expand and clasp the pneumatic clip to the external ear and the side of the head, and;

when said plunger is retracted, the fluid in said annular expandable pneumatic tube is allowed to return to said pneumatic reservoir, so that by decreasing said variable pressure on said pneumatic reservoir the external ear can be moved through said annular expandable pneumatic tube and said central opening, and by increasing said variable pressure on said pneumatic reservoir, said pneumatic clip can be clasped to the external ear and the side of the head, whereby said pneumatic clip comprises a means for proximally attaching devices to the ear, and;

wherein said hydraulic clip is comprised of an annular casing having a central opening, said annular casing further comprising a holding groove and a holding case fashioned to follow the circumference of said central opening, and;

said annular casing further comprising an annular expandable hydraulic tube and hydraulic reservoir, said annular expandable hydraulic tube held in said holding groove and said hydraulic reservoir held in said holding case, and;

said annular casing further comprising an adjustable plunger for applying a variable pressure to said hydraulic reservoir, said plunger having a latch for holding said plunger in position during operation, so that when said plunger applies pressure to said hydraulic reservoir during operation the hydraulic fluid in said hydraulic reservoir is expelled from said hydraulic reservoir into said annular expandable hydraulic tube, thereby forcing said annular expandable hydraulic tube to expand and clasp the hydraulic clip to the external ear and the side of the head, and;

when said plunger is retracted, the fluid in said annular expandable hydraulic tube is allowed to return to said hydraulic reservoir, so that by decreasing said variable pressure on said hydraulic reservoir the external ear can be moved through said annular expandable hydraulic tube and said central opening, and by increasing said variable pressure on said hydraulic reservoir, said hydraulic clip can be clasped to the external ear and the side of the head whereby said hydraulic clip comprises a means for proximally attaching devices to the ear, and;

the lateral surface of said plurality of clips having a supporting material for cushioning said clips against the ear lobe, so that when said plurality of clips is latched against the ear during operation, the supporting material of said lateral surface of said plurality of clips presses laterally against the external ear, and; the medial surface of said plurality of clips having a wedge shaped layer of bracing material applied to it, the thicker part of said wedge shaped layer attached to the posterior circumference of said second arc shaped flange or said annular casing, the thinner part of said wedge shaped layer comprising a frontal pad for sealing and fitting the anterior circumference of said first arc shaped flange or said annular casing against the head and jawbone, and;

said bracing material further having a cushioned lip contour for complementing the shape of the head and neck during operation, such that said cushioned lip contour curves the bracing material of said latching means laterally away from the head where it touches the jaw bone and the side arch of the skull, and said cushioned lip contour curves the bracing material of said latching means medially towards the head and neck where it touches the human body surface beneath the jaw bone and the external ear, so that when said latching means is locked in place between the external ear and the side of the head the posterior portion of said latching means is moved laterally by said wedge shaped layer of bracing material, thereby pressing and sealing the frontal pad against the head and jawbone, so that said latching means comprises a means for proximally attaching devices to the ear.

As shown in FIG. 8, another particular of the invention is in combination with a head phone set having speakers (562, 563) attached to a fitting means (564) for placing said speakers against the ears and a connecting means (566) for connecting said speakers to a playback unit, the improvement comprising;

A pair of sound baffling cups (568, 570) for fully enclosing the ears between said sound baffling cups and the head and neck during operation, said sound baffling cups inserted between said speakers and said fitting means, said speakers attached to the interior of said sound baffling cups, so that the ambient noise reaching the ears during operation is substantially reduced, thereby improving the audibility and perceived rendition of the sound emanating from said speakers, and;

A cushioned lip contour (572, 574) for complimenting the shape of the head and neck during operation, said cushioned lip contour applied to the lips (576, 578) of said sound baffling cups such that said cushioned lip contour curves the lips of said sound baffling cups laterally away from the head where it touches the jaw bone and the side arch of the skull, and said cushioned lip contour curves the lips of said sound baffling cups medially towards the head and neck where it touches the human body surface beneath the jaw bone and behind the inferior external ear, so that the comfort, fit, and sound baffling qualities of said sound baffling cups are substantially improved by said cushioned lip contour.

As shown in FIG. 9, in another particular of the invention a first part of the connecting means (581, 582) which connects to the far speaker (580) is carried along said fitting means (583) and gathered together to form a bundle (584) with a second part (585, 586) of the connecting means which connects to the near speaker (587), both the first and second part of said connecting means extending from said bundle to connect with the connecting means connection (588), so that when said connecting means connection is connected to the playback unit connector, a single path is followed by said connecting means from the speakers of said head phone set to said playback unit.

Rather than carrying the first part of the connecting means along the fitting means by means of a wiring arrangement, it may be preferable to use the fitting means as an insulating substrate for conductive strips (589, 590, 591, 592), which carry the first part of the connecting means along the fitting means. In FIG. 9, the conductive strips (589, 591) running along the top of the fitting means are electronically connected by contacts (593, 594), which are attached to the restraining bands of the fitting means. The conductive strips (590, 592) running along the side of the fitting means are in continuous contact with each other. These factors ensure that the fitting means may function reliably as a substrate for the conductive strips of the connecting means.

Figure 4:
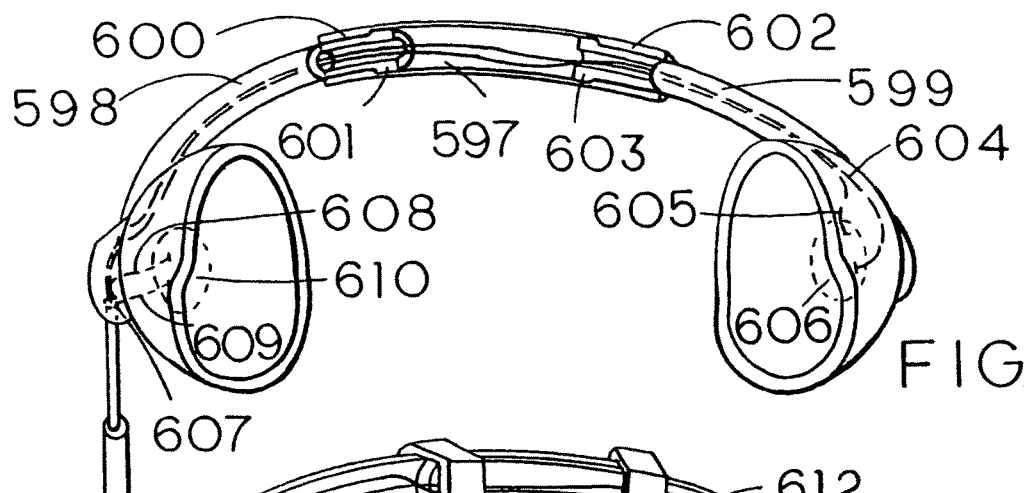
FIG. 4 shows how the single path connecting means may be passed through the tubular tunnel within a hollow tubular fitting means.

Furthermore, as shown in FIG. 4, by using a fitting means comprised of hollow tubular segments, it is possible to pass the connecting means from one speaker to the other through the hollow tubular segments of the fitting means. As illustrated, the middle tube (597) functions as a guide for the first tube (598) and the second tube (599). This eliminates unsightly wiring arrangement and also creates greater compactness of engineering. It is therefore preferable that said fitting means is comprised of elastic hollow tubular segments (597, 598, 599) fashioned to allow a smaller tubular segment (598, 599) to slide fixedly within a larger tubular segment (597), said hollow tubular segments having a restraining means (600, 601, 602, 603) to prevent separation, and;

wherein the length of the arc described by said fitting means is set by sliding said smaller tubular segment to a preferred position within said larger tubular segment, so that the length of the arc may be reduced sufficiently to allow said elastic arc shaped tubes to be worn behind the neck, and;

the first part (604, 605) of the connecting means which connects to the far speaker (606) is carried through said tubes and gathered together to form a bundle (607) with the second part (608, 609) of the connecting means which connects to the near speaker (610), thereby improving the appearance, comfort and utility of said device. This embodiment may also be fashioned from a larger elastic arc shaped tube and a smaller elastic arc shaped tube. And the retraining means of this embodiment is formed by means of the interlocking tube ends (600, 601) and (602, 603). The tight frictional fit of the tubes allows the size of the arc to be adjusted by the frictional feed.

Because the lips of the sound baffling cups form a more stable foundation than the loosely fitting padded speakers or plug-in speakers of some previous head phone sets, it is possible to apply more elastic tension to head phone sets using sound baffling cups. When the elastic tension is increased by a suitable amount, the arc shaped fitting means used in some previous devices may be worn in an arc behind the neck. It is therefore preferable that said fitting means is comprised of two slidably connected elastic arc shaped bands to which the sound baffling cups are attached, and;

wherein the improvement comprises an increase in the tension applied by said arc shaped band to the sound baffling cups, so that when said arc shaped bands are shortened so as to be worn behind the neck, said increase in the tension allows said sound baffling cups to maintain a snug fit against the ears, thereby improving the comfort and utility of said device.

The advantage of placing the fitting means in this fashion is that it is less obtrusive and that headgear may be worn. This embodiment may be improved further by providing arc shaped bands that are grooved. The tubular grooves serve as a guide for the connecting means and allow it to be passed more easily from the far speaker to the near speaker. Therefore as shown in FIG. 5, according to another particular of the invention it is preferable that said elastic arc shaped bands are grooved, and;

a first part (612, 613) of the connecting means which connects to the far speaker (614) is carried through said elastic arc shaped bands (616, 617) and gathered together to form a bundle (618) with a second part (620, 621) of the connecting means which connects to the near speaker (622), both the first and second parts of said connecting means extending from said bundle to connect with the connecting means connection (624), so that when said connecting means connection is connected to the playback unit connector, a single path is followed by said connecting means from the speakers of said head phone set to said playback unit, thereby improving the appearance, comfort and utility of said device.

The connecting means may be the usual wiring arrangement shown in many previous devices. But it may also be comprised of fiber optic cable or it could be fashioned from wire-less or infrared radiation devices. The fiber optic cable confers a better quality to the connecting means, whereas the wire-less or infrared radiation eliminate the wiring arrangement thereby making the connecting means less obtrusive.

What is claimed is:

1. A hermetically sealed enclosure consisting of flexible walls for preserving and containing air or a gas or a mixture of oases, said hermetically sealed enclosure comprising a characteristic novelty and an internal pressure ranging from atmospheric to a high vacuum and further having an electric force generating means comprising conductive plates for regulating a property of said hermetically sealed enclosure, said regulating a property creating a change in said property lasting more than any specified length of time, and: wherein said property is selected from the group consisting of a thermal impedance, and a characteristic acoustic impedance $Z=pc$, where Z is the characteristic acoustic impedance, p is the volumetric mass density of said air or a gas or a mixture of gases, and c is the speed of the sound waves traveling in said air or a gas or a mixture of oases, and: said electric force generating means creates a varying electrostatic repulsive force that acts to vary the separation between said flexible walls, thereby changing the volume of said hermetically sealed enclosure, so that said electric force generating means is effective to use said air or a gas or a mixture of oases to regulate said thermal property impedance, and said characteristic acoustic impedance, or both.

2. The hermetically sealed enclosure of claim 1 comprising a flexible wall, wherein;

said electric force generating means is comprised of at least one conductive coating covering said hermetically sealed enclosure, so that varying an electric charge on said at least one conductive coating creates a varying electrostatic repulsive force that acts to vary the separation between said hermetically sealed enclosure and said flexible wall, thereby changing the volume of said hermetically sealed enclosure, so that said electric force generating means is effective to use said air or a gas or a mixture of gases to regulate said thermal impedance, and said characteristic acoustic impedance, or both.

3. The hermetically sealed enclosure of claim 1, comprising a first flexible wall geometrically congruent to a second flexible wall, said first flexible wall positioned proximally to said second flexible wall so that said first flexible wall overlaps said second flexible wall, and; said electric force generating means comprises a first conductive coating or a first plurality of charged plates covering said first flexible wall, and a second conductive coating or a second plurality of charged plates covering said second flexible wall, said first conductive coating or said first plurality of charged plates electrically Insulated from said second conductive coating or said second plurality of charged plates, and; placing a first electric charge on said first conductive coating or said first plurality of charged plates, and placing a second electric charge on said second conductive coating or said second plurality of charged plates, so that said first electric charge and said second electric charge are of a same electrical polarity, creates an electrostatic repulsive force between said first flexible wall and said second flexible wall, and; varying said first electric charge or said second electric charge causes said electrostatic repulsive force to vary the separation between said first flexible wall and said second flexible wall, thereby, changing to said electric force generating means is effective to use said air or a gas or a mixture of gases to regulate said thermal impedance, and said characteristic acoustic impedance or both, or, placing a third electric charge on said first conductive coating, or said first plurality of charged plates, and placing a fourth electric charge on said second conductive coating or said second plurality of charged plates, so that said third electric charge and said fourth electric charge are of an opposite electrical polarity, creates an electrostatic attractive force between said first flexible wall and said second flexible wall, and; varying said third electric charge or said fourth electric charge causes said electrostatic attractive force to vary the separation between said first flexible wall and said second flexible wall, thereby changing the volume of said hermetically sealed enclosure, so that said electric force generating means is effective to use said air or a gas or a mixture of gases to regulate said thermal impedance, and said characteristic acoustic impedance or both.

4. A hermetically sealed enclosure consisting of flexible walls for preserving and containing air or a gas or a mixture of oases, said hermetically sealed enclosure comprising a characteristic novelty and an internal pressure ranging from atmospheric to a high vacuum and further having an electric force generating means comprising conductive plates, for regulating a characteristic acoustic impedance $Z=pc$, where Z is said characteristic acoustic impedance, o is the volumetric mass density of the medium, and c is the speed of the sound waves traveling in the medium, said regulating said characteristic acoustic impedance creating a change in said characteristic acoustic impedance lasting more than any specified length of time, and: said electric force generating means creating a varying electrostatic repulsive force that acts to vary the separation between said flexible walls, thereby changing the volume of said hermetically sealed enclosure, so that by changing the volume of said hermetically sealed enclosure said electric force generating means is effective to use said air or a gas or a mixture of gases to regulate said characteristic acoustic impedance, and: said hermetically sealed enclosure further comprising a sound absorbing material enclosed within said hermetically sealed enclosure, wherein; said sound absorbing material is prevented from contacting the enclosure walls directly, and; the incident sound transmitted through said hermetically sealed enclosure into said sound absorbing material is inversely proportional to said characteristic acoustic impedance, so that when said characteristic acoustic impedance is decreased the incident sound transmitted through said hermetically sealed enclosure and absorbed by said sound absorbing material is increased, or; when said characteristic acoustic impedance is increased the incident sound transmitted through said hermetically sealed enclosure and absorbed by said sound absorbing material is decreased, so that by varying said characteristic acoustic impedance of said hermetically sealed enclosure, the absorption and reflection of the sound incident on said hermetically sealed enclosure is regulated.

5. A hermetically sealed enclosure consisting of flexible walls for preserving and containing air or a gas or a mixture of gases, said hermetically sealed enclosure comprising a characteristic novelty and having an internal pressure ranging from atmospheric to a high vacuum, and further having comprising a force generating means for regulating a property of said hermetically sealed enclosure, said regulating a property creating a change in said property lasting more than any specified length of time, and; said force generating means selected from the group consisting of an electric force generating means, a hydraulic force generating means, a pneumatic force generating means, a line force generating means, a spring force generating means, a lever force generating means, and a strut force generating means containing a transduction circuit hermetically enclosed within said strut force generating means, and; wherein said property is selected from the group consisting of a geometric property, a thermal impedance, and a characteristic acoustic impedance $Z=\rho c$ where Z is the characteristic impedance, $\rho$ is the volumetric mass density of said air or a gas or a mixture of gases, and c is the speed of the sound waves traveling in said air or a gas or a mixture of gases, so that said force generating means is effective to regulate said geometric property, said thermal impedance, and said characteristic acoustic impedance, and; said hermetically sealed enclosure further comprising a sound absorbing material for directionally regulating the reflection of the incident sound, and sound absorbing material contacted to a surface of said hermetically sealed enclosure, and wherein; the percentage of the incident sound, that is transmitted directly into said surface and absorbed, is substantially constant, and; the incident sound transmitted indirectly through said hermetically sealed enclosure into said sound absorbing material is inversely proportional to said characteristic acoustic impedance, so that when said characteristic acoustic impedance is decreased the incident sound transmitted indirectly through said hermetically sealed enclosure and absorbed by said sound absorbing material is increased, or; when said characteristic acoustic impedance is increased the incident sound transmitted indirectly through said hermetically sealed enclosure and absorbed by said sound absorbing material is decreased, so that by varying said characteristic acoustic impedance of said hermetically sealed enclosure, the absorption and reflection of the sound incident on said hermetically sealed enclosure is directionally regulated.

6. A hermetically sealed enclosure having an internal pressure and comprising a force generating means for regulating a property of said hermetically sealed enclosure, said force generating means selected from the group consisting of an electrostatic force generating means, a hydraulic force generating means, a pneumatic force generating means, a line force generating means, a spring force generating means, a lever force generating means, and a strut force generating means containing a transduction circuit,
    said transduction circuit fully enclosed within said strut force generating means, and;
    wherein said property is selected from the group consisting of a geometric property, a thermal property, and a characteristic acoustic impedance,
    so that said force generating means is effective to regulate said geometric property, said thermal property, and said characteristic acoustic impedance, and;
    a sound absorbing material contacted on a first side to a first wall of a first hermetically sealed enclosure,
    said sound absorbing material contacted on a second side to a second wall of a second hermetically sealed enclosure,
    so that said sound absorbing material is sandwiched between said first hermetically sealed enclosure and said second hermetically sealed enclosure, and;
    the incident sound transmitted through said first hermetically sealed enclosure or said second hermetically sealed enclosure, or both, into said sound absorbing material is inversely proportional to said characteristic acoustic impedance, so that;
    when said characteristic acoustic impedance of said first hermetically sealed enclosure is minimum, said first hermetically sealed enclosure transmits the incident sound into said first side of said sound absorbing material to be absorbed, or;
    when said characteristic acoustic impedance of said first hermetically sealed enclosure is maximum, said first hermetically sealed enclosure reflects the incident sound, thereby reducing the absorption of the incident sound by said first side of said sound absorbing material, and;
    when said characteristic acoustic impedance of said second hermetically sealed enclosure is minimum, said second hermetically sealed enclosure transmits the incident sound into said second side of said sound absorbing material to be absorbed, or;
    when said characteristic acoustic impedance of said second hermetically sealed enclosure is maximum, said second hermetically sealed enclosure reflects the incident sound, thereby reducing the absorption of the incident sound by said second side of said sound absorbing material,
    so that by varying said characteristic acoustic impedance of said first hermetically sealed enclosure or of said second hermetically sealed enclosure, or both, the absorption and reflection of the sound incident on said first hermetically sealed enclosure, or on said second hermetically sealed enclosure, or both, is regulated.

7. A hermetically sealed enclosure having an internal pressure ranging from atmospheric to an ultra high vacuum and comprising a force generating means for regulating a property of said hermetically sealed enclosure,
    said force generating means selected from the group consisting of an electrostatic force generating means, and a strut force generating means containing a transduction circuit,
    said transduction circuit hermetically enclosed within said strut force generating means, and;
    wherein said property is selected from the group consisting of a thermal property, and a characteristic acoustic impedance,
    so that said force generating means is effective to regulate said thermal property, and said characteristic acoustic impedance, said hermetically sealed enclosure further comprising;
    a fixed wall having a first nodal means, said first nodal means comprising a plurality of retracting nodes,
    so that said first nodal means can regulate at least one of a first characteristic acoustic impedance, or a first thermal property, of said fixed wall;
    or,
    a flexible wall having a second nodal means, said second nodal means comprising a plurality of tension nodes, or a plurality of compression nodes, or both, so that said second nodal means can regulate at least one of a geometric property, a second characteristic acoustic impedance, or a second thermal property, of said flexible wall.

8. A hermetically sealed enclosure having an internal pressure and comprising a force generating means for regulating a property of said hermetically sealed enclosure, said force generating means selected from the group consisting of an electrostatic force generating means, a hydraulic force generating means, a pneumatic force generating means; a line force generating means, a spring force generating means, a lever force generating means, and a strut force generating means comprising a transduction circuit, and;
 wherein said property is selected from the group consisting of a geometric property, a thermal property, and an acoustic property,
 so that said force generating means is effective to regulate said geometric property, said thermal property, and said acoustic property, and;
 a vacuum capacitor for sourcing a vacuum, said vacuum capacitor comprised of a plurality of hermetically sealed enclosures containing a plurality of pressure sensors for measuring said vacuum, said plurality of hermetically sealed enclosures connected by a plurality of valves to a piping network for distributing said vacuum, and;
 said plurality of hermetically sealed enclosures having a congruent size and shape, and a geometrically uniform packing, whereby distributing said vacuum is optimized, and;
 said vacuum capacitor having an output pipe for transferring said vacuum at a rate of geometric progression to an external hermetically sealed enclosure,
 so that in operation said vacuum capacitor is connected by said output pipe to said external hermetically sealed enclosure, and said vacuum is transferred to said external hermetically sealed enclosure at a rate of geometric progression.

9. The vacuum capacitor of claim 8 further comprising a pressure varying means for admitting and removing matter to and from said external hermetically sealed enclosure, and to and from said vacuum capacitor, so that the sound baffling characteristics of said external hermetically sealed enclosure can be varied by said admitting and removing of matter, and;
 said sound baffling device further comprising a means for measuring values and characteristics of the ambient sound, and a means for correlating having default parametric values and characteristics, and;
 said means for correlating using the correlation between said values and characteristics of the ambient sound and said default parametric values and characteristics as a benchmark for adjusting said pressure varying means, so that matter is admitted and removed from said external hermetically sealed enclosure as indicated by said benchmark, and;
 said values and characteristics of the ambient sound throughout the physical space which is governed by said sound baffling device enter a convergence towards said default parametric values and characteristics,
 so that after a requisite interval of time an optimum correlation between said default parametric values and characteristics and said measured values and characteristics of the ambient sound is attained.

10. The sound baffling device of claim 9 further comprising an input means for entering and storing input parametric values and characteristics,
 said input means, said means for measuring, and said means for correlating in combination comprising a controlling means, and;
 said controlling means ensuring that any of said input parametric values and characteristics stored through said input means are used to replace the corresponding default parametric values and characteristics of said means for correlating in operation,
 so that said means for correlating uses the correlation between said values and characteristics of the ambient sound and the parametric values and characteristics to create said benchmark defined in claim 9, and matter is admitted and removed from said external hermetically sealed enclosure as indicated by said benchmark,
 so that said values and characteristics of the ambient sound throughout the physical space which is governed by said sound baffling device enter a convergence towards said parametric values and characteristics,
 whereby after a requisite interval of time an optimum correlation between said parametric values and characteristics and said values and characteristics of the ambient sound is attained.

11. The sound baffling device of claim 10 further comprising a microprocessor governed by a controlling program, said controlling program having an acoustic model of the physical space governed by said sound baffling device, said acoustic model devised to operate in accordance with the principles of acoustic science, and;
 said controlling program capable of calculating predicted values and characteristics of the ambient sound which should result from admitting and removing matter to and from said external hermetically sealed enclosure, and;
 said controlling program further using the correlation between said predicted values and characteristics and the parametric values and characteristics to create a further benchmark, and;
 said controlling program using said further benchmark and said benchmark of claim 10 to calculate instructions for said means for correlating, and;
 said means for correlating using said instructions to adjust said pressure varying means, so that matter is admitted and removed from said external hermetically sealed enclosure as indicated by said instructions, and;
 said values and characteristics of the ambient sound throughout the physical space which is governed by said sound baffling device enter a convergence towards said parametric values and characteristics, and;
 after a requisite interval of time an optimum correlation between said parametric values and characteristics and said values and characteristics of the ambient sound is attained.

12. The external hermetically sealed enclosure of claim 9 having a flexible wall, an acoustic impedance, and a thermal impedance, wherein;
 said electrostatic force generating means is comprised of at least one conductive coating covering said external hermetically sealed enclosure;
 so that varying an electric charge on said at least one conductive coating creates a varying electrostatic repulsive force that acts to vary the separation between said external hermetically sealed enclosure and said flexible wall,
 whereby said acoustic impedance, or said thermal impedance, or both, are regulated.

13. The external hermetically sealed enclosure of claim 9 comprised of a first flexible wall geometrically congruent to a second flexible wall, said electrostatic force generating means, said acoustic impedance, and said thermal impedance, wherein;
  said first flexible wall is positioned proximally to said second flexible wall so that said first flexible wall overlaps said second flexible wall, and;
  said electrostatic force generating means having a first conductive coating or a first plurality of charged plates covering said first flexible wall,
  and a second conductive coating or a second plurality of charged plates covering said second flexible wall,
  said first conductive coating or said first plurality of charged plates electrically insulated from said second conductive coating or said second plurality of charged plates, and;
  placing a first electric charge on said first conductive coating or said first plurality of charged plates, and placing a second electric charge on said second conductive coating or said second plurality of charged plates,
  so that said first electric charge and said second electric charge are of a same electrical polarity, creates an electrostatic repulsive force between said first flexible wall and said second flexible wall, and;
  varying said first electric charge or said second electric charge causes said electrostatic repulsive force to vary the separation between said first flexible wall and said second flexible wall, whereby said acoustic impedance, or said thermal impedance, or both, are regulated, or;
  placing a third electric charge on said first conductive coating, or said first plurality of charged plates, and placing a fourth electric charge on said second conductive coating or said second plurality of charged plates,
  so that said third electric charge and said fourth electric charge are of an opposite electrical polarity, creates an electrostatic attractive force between said first flexible wall and said second flexible wall, and;
  varying said third electric charge or said fourth electric charge causes said electrostatic attractive force to vary the separation between said first flexible wall and said second flexible wall, whereby said acoustic impedance, or said thermal impedance, or both, are regulated.

14. The external hermetically sealed enclosure of claim 9 further comprising a sound absorbing material enclosed within said external hermetically sealed enclosure, and wherein;
  said sound absorbing material is prevented from contacting the enclosure walls directly, and;
  the incident sound transmitted through said hermetically sealed enclosure into said sound absorbing material is inversely proportional to said acoustic impedance, so that when said acoustic impedance is decreased the incident sound transmitted through said hermetically sealed enclosure and absorbed by said sound absorbing material is increased, or;
  when said acoustic impedance is increased the incident sound transmitted through said hermetically sealed enclosure and absorbed by said sound absorbing material is decreased,
  so that by varying said acoustic impedance of said external hermetically sealed enclosure, the absorption and reflection of the sound incident on said external hermetically sealed enclosure is regulated.

15. The hermetically sealed external enclosure of claim 9, further comprising a sound absorbing material contacted to a surface of said hermetically sealed enclosure, and wherein;
  the percentage of the incident sound, that is transmitted directly into said surface and absorbed, is constant, and;
  the incident sound transmitted indirectly through said hermetically sealed enclosure into said sound absorbing material is inversely proportional to said acoustic impedance,
  so that when said acoustic impedance is decreased the incident sound transmitted indirectly through said hermetically sealed enclosure and absorbed by said sound absorbing material is increased, or;
  when said acoustic impedance is increased the incident sound transmitted indirectly through said hermetically sealed enclosure and absorbed by said sound absorbing material is decreased, so that by varying said acoustic impedance of said hermetically sealed enclosure, the absorption and reflection of the sound incident on said hermetically sealed enclosure is directionally regulated.

16. A sound absorbing material contacted on a first side to a first wall of a first external hermetically sealed enclosure as defined in claim 9,
  said sound absorbing material contacted on a second side to a second wall of a second external hermetically sealed enclosure as defined in claim 9,
  so that said sound absorbing material is sandwiched between said first external hermetically sealed enclosure and said second external hermetically sealed enclosure, and;
  the incident sound transmitted through said first external hermetically sealed enclosure or said second external hermetically sealed enclosure, or both, into said sound absorbing material is inversely proportional to said acoustic impedance, so that;
  when said acoustic impedance of said first external hermetically sealed enclosure is minimum, said first external hermetically sealed enclosure transmits the incident sound into said first side of said sound absorbing material to be absorbed, or,
  when said acoustic impedance of said first external hermetically sealed enclosure is maximum, said first external hermetically sealed enclosure reflects the incident sound, thereby reducing the absorption of the incident sound by said first side of said sound absorbing material, and;
  when said acoustic impedance of said second hermetically sealed external enclosure is minimum, said second hermetically sealed external enclosure transmits the incident sound into said second side of said sound absorbing material to be absorbed, or;
  when said acoustic impedance of said second external hermetically sealed enclosure is maximum, said second external hermetically sealed enclosure reflects the incident sound, thereby reducing the absorption of the incident sound by said second side of said sound absorbing material,
  so that by varying said acoustic impedance of said first external hermetically sealed enclosure or of said second external hermetically sealed enclosure, or both, the absorption and reflection of the sound incident on said first external hermetically sealed enclosure, or on said second external hermetically sealed enclosure, or both, is regulated.

17. A hermetically sealed enclosure having an internal pressure ranging from atmospheric to an ultra high vacuum and comprising a force generating means for regulating a property of said hermetically sealed enclosure, said force generating means selected from the group consisting of an electrostatic force generating means, and a strut force generating means containing a transduction circuit, said transduction circuit hermetically enclosed within said strut force generating means, and;

wherein said property is selected from the group consisting of a thermal property, and a characteristic acoustic impedance, so that said force generating means is effective to regulate said thermal property, and said characteristic acoustic impedance, and;

The said hermetically sealed enclosure further comprising a latching means for attaching an element proximally to the ear, said latching means selected from the group consisting of a jointed clip comprising a first part shaped to fit the curvature of the anterior half of the external ear, and a second part shaped to fit the curvature of the posterior half of the external ear, and;

wherein said second part of said jointed clip is attached by a hinge to a pivot mounted in the distal end of said first part;

the distal end of the second part further having a tongue for latching into a tongue groove located on the proximal end of said first part, so that when said jointed clip is attached to the external ear by wedging said first part against the anterior portion of the external ear, said second part may be movably fitted through rotation about said hinge in behind the posterior portion of the external ear, so that in operation said second part is fitted laterally over said first part and locked in place by said tongue groove, and;

said jointed clip is clasped between the external ear and the side of the head, so that said jointed clip comprises a means for proximally attaching elements to the ear;

a flat sliding clip comprised of a first arc shaped flange having a curvature corresponding to the shape of the anterior portion of the external ear and a second arc shaped flange having a curvature corresponding to the shape of the posterior portion of the external ear, so that when said flat sliding clip is attached to the ear by wedging said second arc shaped flange in behind the posterior portion of the external ear, said first arc shaped flange may be movably fitted against the anterior portion of the external ear, so that in operation said second arc shaped flange is fitted into said first arc shaped flange by inserting a tongue protruding from said second arc shaped flange into a notch in said first arc shaped flange, so that said first arc shaped flange and said second arc shaped flange are held together by elastic tension, whereby said flat sliding clip is clasped between the external ear and the side of the head, so that said flat sliding clip comprises a means for proximally attaching devices to the ear;

a pneumatic clip comprised of an annular casing having a central opening, said annular casing further comprising a holding groove and a holding case fashioned to follow the circumference of said central opening, and;

said annular casing further comprising an annular expandable pneumatic tube and pneumatic reservoir, said annular expandable pneumatic tube held in said holding groove and said pneumatic reservoir held in said holding case, and;

said annular casing further comprising an adjustable plunger for applying a variable pressure to said pneumatic reservoir, said plunger having a latch for holding said plunger in position during operation, so that when said plunger applies pressure to said pneumatic reservoir during operation the hydraulic fluid in said pneumatic reservoir is expelled from said pneumatic reservoir into said annular expandable pneumatic tube, thereby forcing said annular expandable pneumatic tube to expand and clasp the pneumatic clip to the external ear and the side of the head, and;

when said plunger is retracted, the fluid in said annular expandable pneumatic tube is allowed to return to said pneumatic reservoir, so that by decreasing said variable pressure on said pneumatic reservoir the external ear can be moved through said annular expandable pneumatic tube and said central opening, and by increasing said variable pressure on said pneumatic reservoir, said pneumatic clip can be clasped to the external ear and the side of the head, whereby said pneumatic clip comprises a means for proximally attaching devices to the ear;

and a hydraulic clip comprised of an annular casing having a central opening, said annular casing further comprising a holding groove and a holding case fashioned to follow the circumference of said central opening, and;

said annular casing further comprising an annular expandable hydraulic tube and hydraulic reservoir, said annular expandable hydraulic tube held in said holding groove and said hydraulic reservoir held in said holding case, and;

said annular casing further comprising an adjustable plunger for applying a variable pressure to said hydraulic reservoir, said plunger having a latch for holding said plunger in position during operation, so that when said plunger applies pressure to said hydraulic reservoir during operation the hydraulic fluid in said hydraulic reservoir is expelled from said hydraulic reservoir into said annular expandable hydraulic tube, thereby forcing said annular expandable hydraulic tube to expand and clasp the hydraulic clip to the external ear and the side of the head, and;

when said plunger is retracted, the fluid in said annular expandable hydraulic tube is allowed to return to said hydraulic reservoir, so that by decreasing said variable pressure on said hydraulic reservoir the external ear can be moved through said annular expandable hydraulic tube and said central opening, and by increasing said variable pressure on said hydraulic reservoir, said hydraulic clip can be clasped to the external ear and the side of the head whereby said hydraulic clip comprises a means for proximally attaching devices to the ear, the lateral surface of said latching means having a supporting material for cushioning said clips against the ear lobe, so that when said latching means is latched against the ear during operation, the supporting material of said lateral surface of said latching means presses laterally against the external ear, and;

the medial surface of said latching means having a wedge shaped layer of bracing material applied to it, the thicker part of said wedge shaped layer attached to the posterior circumference of said second part or said second arc shaped flange or said annular casing, the thinner part of said wedge shaped layer comprising a frontal pad for sealing and fitting the anterior circumference of said first part or said first arc shaped flange or said annular casing against the head and jawbone, and;

said bracing material further having a cushioned lip contour for complementing the shape of the head and neck during operation, such that said cushioned lip contour curves the bracing material of said latching means laterally away from the head where it touches the jaw bone and the side arch of the skull, and said cushioned lip contour curves the bracing material of said latching means medially towards the head and neck where it touches the human body surface beneath the jaw bone and the external ear, so that when said latching means is locked in place between the external ear and the side of the head the posterior portion of said latching means is moved laterally by said wedge shaped layer of bracing material, thereby pressing and sealing the frontal pad against the head and jawbone, so that said latching means comprises a means for proximally attaching devices to the ear.

* * * * *